(12) United States Patent
Murillo et al.

(10) Patent No.: US 10,806,442 B2
(45) Date of Patent: **\*Oct. 20, 2020**

(54) AUTOMATICALLY RELOADING SUTURE PASSER DEVICES THAT PREVENT ENTANGLEMENT

(71) Applicant: CETERIX ORTHOPAEDICS, INC., Fremont, CA (US)

(72) Inventors: Michael Murillo, Menlo Park, CA (US); Mark Y. Hirotsuka, San Jose, CA (US); Michael J. Hendricksen, Redwood City, CA (US); Stephen J. Peter, San Francisco, CA (US); Christopher P. Bender, Oakland, CA (US)

(73) Assignee: Ceterix Orthopaedics, Inc., Fremont, CA (US)

( * ) Notice: Subject to any disclaimer, the term of this patent is extended or adjusted under 35 U.S.C. 154(b) by 103 days.

This patent is subject to a terminal disclaimer.

(21) Appl. No.: 16/241,764

(22) Filed: Jan. 7, 2019

(65) Prior Publication Data
US 2019/0133572 A1 May 9, 2019

Related U.S. Application Data

(63) Continuation of application No. 15/216,482, filed on Jul. 21, 2016, now Pat. No. 10,226,245.
(Continued)

(51) Int. Cl.
*A61B 17/04* (2006.01)
*A61B 17/062* (2006.01)
(Continued)

(52) U.S. Cl.
CPC ...... *A61B 17/0469* (2013.01); *A61B 17/0625* (2013.01); *A61B 17/06133* (2013.01);
(Continued)

(58) Field of Classification Search
CPC ............ A61B 17/0469; A61B 17/0482; A61B 17/0625; A61B 17/06133;
(Continued)

(56) References Cited

U.S. PATENT DOCUMENTS

| 1,037,864 A | 9/1912 | Carlson et al. |
| 2,738,790 A | 3/1956 | Todt, Sr. et al. |

(Continued)

FOREIGN PATENT DOCUMENTS

| CN | 201263696 Y | 7/2009 |
| CN | 101961256 A | 2/2011 |

(Continued)

OTHER PUBLICATIONS

Asik et al.; Strength of different meniscus suturing techniques; Knee Sur, Sports Traumotol, Arthroscopy; vol. 5; No. 2; pp. 80-83; (year of publication is sufficiently earlier than the effective U.S. filing date and any foreign priority date) 1997.

(Continued)

*Primary Examiner* — Erich G Herbermann
(74) *Attorney, Agent, or Firm* — Norman F. Hainer, Jr.

(57) ABSTRACT

Suture passers and methods of use. Described herein are suture passers preloaded with suture, including cartridges that couple to a suture passer to form a loaded suture passer that are configured to prevent a length of suture (e.g., already-passed suture) from re-entering the channel of the suture passer jaw and getting recaptured and/or entangled by the tissue penetrator. In particular, described herein are preloaded and automatically re-loading suture passers that are adapted to include a gate, guide, or shield on one of the jaws of the suture passer, and methods of operating such suture passers for surgical use including repairing tissue.

16 Claims, 28 Drawing Sheets

Related U.S. Application Data

(60) Provisional application No. 62/195,141, filed on Jul. 21, 2015.

(51) Int. Cl.
  *A61B 17/06* (2006.01)
  *A61B 17/00* (2006.01)

(52) U.S. Cl.
  CPC .............. *A61B 2017/0053* (2013.01); *A61B 2017/06042* (2013.01)

(58) Field of Classification Search
  CPC .... A61B 2017/0477; A61B 2017/0479; A61B 2017/048; A61B 2017/0472; A61B 2017/06052; A61B 2017/06042; A61B 2017/0053
  See application file for complete search history.

(56) References Cited

U.S. PATENT DOCUMENTS

| | | |
|---|---|---|
| 2,748,773 A | 6/1956 | Vacheresse, Jr. |
| 3,470,875 A | 10/1969 | Johnson |
| 3,580,256 A | 5/1971 | Wilkinson et al. |
| 3,807,407 A | 4/1974 | Schweizer |
| 3,842,840 A | 10/1974 | Schweizer |
| 3,901,244 A | 8/1975 | Schweizer |
| 4,021,896 A | 5/1977 | Stierlein |
| 4,109,658 A | 8/1978 | Hughes |
| 4,164,225 A | 8/1979 | Johnson et al. |
| 4,236,470 A | 12/1980 | Stenson |
| 4,345,601 A | 8/1982 | Fukuda |
| 4,440,171 A | 4/1984 | Nomoto et al. |
| 4,553,543 A | 11/1985 | Amarasinghe |
| 4,605,002 A | 8/1986 | Rebuffat |
| 4,706,666 A | 11/1987 | Sheets |
| 4,836,205 A | 6/1989 | Barrett |
| 4,957,498 A | 9/1990 | Caspari et al. |
| 4,981,149 A | 1/1991 | Yoon et al. |
| 5,002,561 A | 3/1991 | Fisher |
| 5,011,491 A | 4/1991 | Boenko et al. |
| 5,037,433 A | 8/1991 | Wilk et al. |
| 5,059,201 A | 10/1991 | Asnis |
| 5,059,206 A | 10/1991 | Winters |
| 5,112,344 A | 5/1992 | Petros |
| 5,129,912 A | 7/1992 | Noda et al. |
| 5,139,520 A | 8/1992 | Rosenberg |
| 5,156,608 A | 10/1992 | Troidl et al. |
| 5,193,473 A | 3/1993 | Asao et al. |
| 5,219,358 A | 6/1993 | Bendel et al. |
| 5,222,962 A | 6/1993 | Burkhart |
| 5,250,053 A | 10/1993 | Snyder |
| 5,250,055 A | 10/1993 | Moore et al. |
| 5,281,237 A | 1/1994 | Gimpelson |
| 5,312,422 A | 5/1994 | Trott |
| 5,320,633 A | 6/1994 | Allen et al. |
| 5,330,488 A | 7/1994 | Goldrath |
| 5,336,229 A | 8/1994 | Noda |
| 5,342,389 A | 8/1994 | Haber et al. |
| 5,364,410 A | 11/1994 | Faille et al. |
| 5,368,601 A | 11/1994 | Sauer et al. |
| 5,383,877 A | 1/1995 | Clarke |
| 5,389,103 A | 2/1995 | Melzer et al. |
| 5,391,174 A | 2/1995 | Weston |
| 5,397,325 A | 3/1995 | Della Badia et al. |
| 5,403,328 A | 4/1995 | Shallman |
| 5,405,352 A | 4/1995 | Weston |
| 5,405,532 A | 4/1995 | Loew et al. |
| 5,431,666 A | 7/1995 | Sauer et al. |
| 5,431,669 A | 7/1995 | Thompson et al. |
| 5,437,681 A | 8/1995 | Meade et al. |
| 5,454,823 A | 10/1995 | Richardson et al. |
| 5,454,834 A | 10/1995 | Boebel et al. |
| 5,468,251 A | 11/1995 | Buelna |
| 5,474,057 A | 12/1995 | Makower et al. |
| 5,478,344 A | 12/1995 | Stone et al. |
| 5,478,345 A | 12/1995 | Stone et al. |
| 5,480,406 A | 1/1996 | Nolan et al. |
| 5,496,335 A | 3/1996 | Thomason et al. |
| 5,499,991 A | 3/1996 | Garman et al. |
| 5,507,756 A | 4/1996 | Hasson |
| 5,507,757 A | 4/1996 | Sauer et al. |
| 5,520,702 A | 5/1996 | Sauer et al. |
| 5,540,704 A | 7/1996 | Gordon et al. |
| 5,540,705 A | 7/1996 | Meade et al. |
| 5,562,686 A | 10/1996 | Sauer et al. |
| 5,569,301 A | 10/1996 | Granger et al. |
| 5,571,090 A | 11/1996 | Sherts |
| 5,571,119 A | 11/1996 | Atala |
| 5,575,800 A | 11/1996 | Gordon |
| 5,578,044 A | 11/1996 | Gordon et al. |
| 5,601,576 A | 2/1997 | Garrison |
| 5,607,435 A | 3/1997 | Sachdeva et al. |
| 5,616,131 A | 4/1997 | Sauer et al. |
| 5,618,290 A | 4/1997 | Toy et al. |
| 5,626,588 A | 5/1997 | Sauer et al. |
| 5,632,748 A | 5/1997 | Beck et al. |
| 5,632,751 A | 5/1997 | Piraka |
| 5,643,289 A | 7/1997 | Sauer et al. |
| 5,645,552 A | 7/1997 | Sherts |
| 5,653,716 A | 8/1997 | Malo et al. |
| 5,665,096 A | 9/1997 | Yoon |
| 5,669,917 A | 9/1997 | Sauer et al. |
| 5,674,229 A | 10/1997 | Tovey et al. |
| 5,674,230 A | 10/1997 | Tovey et al. |
| 5,681,331 A | 10/1997 | de la Torre et al. |
| 5,690,652 A | 11/1997 | Wurster et al. |
| 5,713,910 A | 2/1998 | Gordon et al. |
| 5,728,107 A | 3/1998 | Zlock et al. |
| 5,728,113 A | 3/1998 | Sherts |
| 5,730,747 A | 3/1998 | Ek et al. |
| 5,741,278 A | 4/1998 | Stevens |
| 5,749,879 A | 5/1998 | Middleman et al. |
| 5,755,728 A | 5/1998 | Maki |
| 5,759,188 A | 6/1998 | Yoon |
| 5,766,183 A | 6/1998 | Sauer |
| 5,792,153 A | 8/1998 | Swain et al. |
| 5,797,958 A | 8/1998 | Yoon |
| 5,800,445 A | 9/1998 | Ratcliff et al. |
| 5,814,054 A | 9/1998 | Kortenbach et al. |
| 5,814,069 A * | 9/1998 | Schulze ............ A61B 17/0469 206/339 |
| 5,824,009 A | 10/1998 | Fukuda et al. |
| 5,827,300 A | 10/1998 | Fleega |
| 5,843,126 A | 12/1998 | Jameel |
| 5,865,836 A | 2/1999 | Miller |
| 5,871,490 A | 2/1999 | Schulze et al. |
| 5,876,411 A | 3/1999 | Kontos |
| 5,876,412 A | 3/1999 | Piraka |
| 5,895,393 A | 4/1999 | Pagedas |
| 5,895,395 A | 4/1999 | Yeung |
| 5,897,563 A | 4/1999 | Yoon et al. |
| 5,899,911 A | 5/1999 | Carter |
| 5,906,630 A | 5/1999 | Anderhub et al. |
| 5,908,428 A | 6/1999 | Scirica et al. |
| 5,910,148 A | 6/1999 | Reimels et al. |
| 5,935,138 A | 8/1999 | McJames, II et al. |
| 5,938,668 A | 8/1999 | Scirica et al. |
| 5,944,739 A | 8/1999 | Zlock et al. |
| 5,947,982 A | 9/1999 | Duran |
| 5,980,538 A | 11/1999 | Fuchs et al. |
| 5,993,466 A | 11/1999 | Yoon |
| 5,997,554 A | 12/1999 | Thompson |
| 6,039,753 A | 3/2000 | Meislin |
| 6,042,601 A | 3/2000 | Smith |
| 6,048,351 A | 4/2000 | Gordon et al. |
| 6,051,006 A | 4/2000 | Shluzas et al. |
| 6,053,933 A | 4/2000 | Balazs et al. |
| 6,056,771 A | 5/2000 | Proto |
| 6,071,289 A | 6/2000 | Stefanchik et al. |
| 6,077,276 A | 6/2000 | Kontos |
| 6,099,550 A | 8/2000 | Yoon |
| 6,099,568 A | 8/2000 | Simonian et al. |
| 6,113,610 A | 9/2000 | Poncet |

(56) References Cited

U.S. PATENT DOCUMENTS

| | | | |
|---|---|---|---|
| 6,126,666 A | 10/2000 | Trapp et al. |
| 6,129,741 A | 10/2000 | Wurster et al. |
| 6,139,556 A | 10/2000 | Kontos |
| 6,152,934 A | 11/2000 | Harper et al. |
| 6,159,224 A | 12/2000 | Yoon |
| 6,190,396 B1 | 2/2001 | Whitin et al. |
| 6,221,085 B1 | 4/2001 | Djurovic |
| 6,231,606 B1 | 5/2001 | Graf et al. |
| 6,238,414 B1 | 5/2001 | Griffiths |
| 6,264,694 B1 | 7/2001 | Weiler |
| 6,277,132 B1 | 8/2001 | Brhel |
| 6,322,570 B1 | 11/2001 | Matsutani et al. |
| 6,325,808 B1 | 12/2001 | Bernard et al. |
| 6,355,050 B1 | 3/2002 | Andreas et al. |
| 6,368,334 B1 | 4/2002 | Sauer |
| 6,368,343 B1 | 4/2002 | Bonutti et al. |
| 6,443,963 B1 | 9/2002 | Baldwin et al. |
| 6,511,487 B1 | 1/2003 | Oren et al. |
| 6,533,795 B1 | 3/2003 | Tran et al. |
| 6,533,796 B1 | 3/2003 | Sauer et al. |
| 6,551,330 B1 | 4/2003 | Bain et al. |
| 6,585,744 B1 | 7/2003 | Griffith |
| 6,626,917 B1 | 9/2003 | Craig |
| 6,626,929 B1 | 9/2003 | Bannerman |
| 6,638,283 B2 | 10/2003 | Thal |
| 6,638,286 B1 | 10/2003 | Burbank et al. |
| 6,641,592 B1 | 11/2003 | Sauer et al. |
| 6,719,765 B2 | 4/2004 | Bonutti |
| 6,723,107 B1 | 4/2004 | Skiba et al. |
| 6,770,084 B1 | 8/2004 | Bain et al. |
| 6,833,005 B1 | 12/2004 | Mantas |
| 6,896,686 B2 | 5/2005 | Weber |
| 6,921,408 B2 | 7/2005 | Sauer |
| 6,923,806 B2 | 8/2005 | Hooven et al. |
| 6,923,819 B2 | 8/2005 | Meade et al. |
| 6,936,054 B2 | 8/2005 | Chu |
| 6,972,027 B2 | 12/2005 | Fallin et al. |
| 6,984,237 B2 | 1/2006 | Hatch et al. |
| 6,991,635 B2 | 1/2006 | Takamoto et al. |
| 6,997,931 B2 | 2/2006 | Sauer et al. |
| 6,997,932 B2 | 2/2006 | Dreyfuss et al. |
| 7,004,951 B2 | 2/2006 | Gibbens, III |
| 7,029,480 B2 | 4/2006 | Klein et al. |
| 7,029,481 B1 | 4/2006 | Burdulis, Jr. et al. |
| 7,041,111 B2 | 5/2006 | Chu |
| 7,063,710 B2 | 6/2006 | Takamoto et al. |
| 7,087,060 B2 | 8/2006 | Clark |
| 7,112,208 B2 | 9/2006 | Morris et al. |
| 7,118,583 B2 | 10/2006 | O'Quinn et al. |
| 7,131,978 B2 | 11/2006 | Sancoff et al. |
| 7,153,312 B1 | 12/2006 | Torrie et al. |
| 7,166,116 B2 | 1/2007 | Lizardi et al. |
| 7,175,636 B2 | 2/2007 | Yamamoto et al. |
| 7,211,093 B2 | 5/2007 | Sauer et al. |
| 7,232,448 B2 | 6/2007 | Battles et al. |
| 7,235,086 B2 | 6/2007 | Sauer et al. |
| 7,311,715 B2 | 12/2007 | Sauer et al. |
| 7,344,545 B2 | 3/2008 | Takemoto et al. |
| 7,390,328 B2 | 6/2008 | Modesitt |
| 7,481,817 B2 | 1/2009 | Sauer |
| 7,481,826 B2 | 1/2009 | Cichocki |
| 7,491,212 B2 | 2/2009 | Sikora et al. |
| 7,588,583 B2 | 9/2009 | Hamilton et al. |
| 7,594,922 B1 | 9/2009 | Goble et al. |
| 7,632,284 B2 | 12/2009 | Martinek et al. |
| 7,674,276 B2 | 3/2010 | Stone et al. |
| 7,717,927 B2 | 5/2010 | Hahn et al. |
| 7,722,630 B1 | 5/2010 | Stone et al. |
| 7,731,727 B2 | 6/2010 | Sauer |
| 7,736,372 B2 | 6/2010 | Reydel et al. |
| 7,749,236 B2 | 7/2010 | Oberlaender et al. |
| 7,842,050 B2 | 11/2010 | Diduch et al. |
| 7,879,046 B2 | 2/2011 | Weinert et al. |
| 7,883,519 B2 | 2/2011 | Oren et al. |
| 7,951,147 B2 | 5/2011 | Privitera et al. |
| 7,951,159 B2 | 5/2011 | Stokes et al. |
| 7,972,344 B2 | 7/2011 | Murray et al. |
| 8,298,230 B2 | 10/2012 | Sutter et al. |
| 8,394,112 B2 | 3/2013 | Nason |
| 8,398,673 B2 | 3/2013 | Hinchliffe et al. |
| 8,449,533 B2 | 5/2013 | Saliman et al. |
| 8,465,505 B2 | 6/2013 | Murillo et al. |
| 8,500,809 B2 | 8/2013 | Saliman |
| 8,540,732 B2 * | 9/2013 | Weinert ............. A61B 17/0469 606/139 |
| 8,562,631 B2 | 10/2013 | Saliman |
| 8,632,563 B2 | 1/2014 | Nagase et al. |
| 8,647,354 B2 | 2/2014 | Domingo |
| 8,663,253 B2 | 3/2014 | Saliman |
| 8,702,731 B2 | 4/2014 | Saliman |
| 8,808,299 B2 | 8/2014 | Saliman et al. |
| 8,821,518 B2 | 9/2014 | Saliman |
| 8,888,848 B2 | 11/2014 | Saliman et al. |
| 8,911,456 B2 | 12/2014 | McCutcheon et al. |
| 8,920,441 B2 | 12/2014 | Saliman et al. |
| 9,011,454 B2 | 4/2015 | Hendrickson et al. |
| 9,211,119 B2 | 12/2015 | Hendrickson et al. |
| 9,247,934 B2 | 2/2016 | Murillo et al. |
| 9,247,935 B2 | 2/2016 | George et al. |
| 9,314,234 B2 | 4/2016 | Hirotsuka et al. |
| 9,332,980 B2 | 5/2016 | George et al. |
| 9,492,162 B2 | 11/2016 | Murillo et al. |
| 9,700,299 B2 | 7/2017 | Saliman et al. |
| 9,848,868 B2 | 12/2017 | Saliman |
| 9,861,354 B2 | 1/2018 | Saliman et al. |
| 9,913,638 B2 | 3/2018 | Saliman et al. |
| 10,004,492 B2 | 6/2018 | Hendricksen et al. |
| 10,143,464 B2 | 12/2018 | George et al. |
| 10,188,382 B2 | 1/2019 | Murillo et al. |
| 2001/0041938 A1 | 11/2001 | Hein |
| 2002/0169477 A1 | 11/2002 | Demopulos et al. |
| 2003/0023250 A1 | 1/2003 | Watschke et al. |
| 2003/0065336 A1 | 4/2003 | Xiao |
| 2003/0065337 A1 | 4/2003 | Topper et al. |
| 2003/0078599 A1 | 4/2003 | O'Quinn et al. |
| 2003/0078617 A1 | 4/2003 | Schwartz et al. |
| 2003/0181926 A1 | 9/2003 | Dana et al. |
| 2003/0204194 A1 | 10/2003 | Bittar |
| 2003/0216755 A1 | 11/2003 | Shikhman et al. |
| 2003/0233106 A1 | 12/2003 | Dreyfuss |
| 2004/0117014 A1 | 6/2004 | Bryant |
| 2004/0249392 A1 | 12/2004 | Mikkaichi et al. |
| 2004/0249394 A1 | 12/2004 | Morris et al. |
| 2004/0267304 A1 | 12/2004 | Zannis et al. |
| 2005/0033319 A1 | 2/2005 | Gambale et al. |
| 2005/0033365 A1 | 2/2005 | Courage |
| 2005/0043746 A1 | 2/2005 | Pollak et al. |
| 2005/0080434 A1 | 4/2005 | Chung et al. |
| 2005/0090837 A1 | 4/2005 | Sixto, Jr. et al. |
| 2005/0090840 A1 | 4/2005 | Gerbino et al. |
| 2005/0154403 A1 | 7/2005 | Sauer et al. |
| 2005/0228406 A1 | 10/2005 | Bose |
| 2005/0288690 A1 | 12/2005 | Bourque et al. |
| 2006/0020272 A1 | 1/2006 | Gildenberg |
| 2006/0047289 A1 | 3/2006 | Fogel |
| 2006/0084974 A1 | 4/2006 | Privitera et al. |
| 2006/0178680 A1 | 8/2006 | Beverly et al. |
| 2006/0282098 A1 | 12/2006 | Shelton et al. |
| 2007/0032799 A1 | 2/2007 | Pantages et al. |
| 2007/0038230 A1 | 2/2007 | Stone et al. |
| 2007/0156174 A1 | 7/2007 | Kaiser et al. |
| 2007/0185532 A1 | 8/2007 | Stone et al. |
| 2007/0219571 A1 | 9/2007 | Balbierz et al. |
| 2007/0250118 A1 | 10/2007 | Masini |
| 2007/0260260 A1 | 11/2007 | Hahn et al. |
| 2007/0260278 A1 | 11/2007 | Wheeler et al. |
| 2008/0086147 A1 | 4/2008 | Knapp |
| 2008/0091219 A1 | 4/2008 | Marshall et al. |
| 2008/0097482 A1 | 4/2008 | Bain et al. |
| 2008/0097489 A1 | 4/2008 | Goldfarb et al. |
| 2008/0140091 A1 | 6/2008 | DeDeyne et al. |
| 2008/0140094 A1 | 6/2008 | Schwartz et al. |
| 2008/0228204 A1 | 9/2008 | Hamilton et al. |
| 2008/0234725 A1 | 9/2008 | Griffiths et al. |

(56) References Cited

U.S. PATENT DOCUMENTS

| | | |
|---|---|---|
| 2008/0243147 A1 | 10/2008 | Hamilton et al. |
| 2008/0269783 A1 | 10/2008 | Griffith |
| 2008/0275553 A1 | 11/2008 | Wolf et al. |
| 2008/0294256 A1 | 11/2008 | Hagan et al. |
| 2009/0012520 A1 | 1/2009 | Hixson et al. |
| 2009/0012538 A1 | 1/2009 | Saliman et al. |
| 2009/0018554 A1 | 1/2009 | Thorne et al. |
| 2009/0062816 A1 | 3/2009 | Weber |
| 2009/0062819 A1 | 3/2009 | Burkhart et al. |
| 2009/0105729 A1 | 4/2009 | Zentgraf |
| 2009/0105751 A1 | 4/2009 | Zentgraf |
| 2009/0112232 A1 | 4/2009 | Crainich et al. |
| 2009/0131956 A1 | 5/2009 | Dewey et al. |
| 2009/0209998 A1 | 8/2009 | Widmann |
| 2009/0216268 A1 | 8/2009 | Panter |
| 2009/0228041 A1 | 9/2009 | Domingo |
| 2009/0259233 A1 | 10/2009 | Bogart et al. |
| 2009/0281619 A1 | 11/2009 | Le et al. |
| 2009/0306684 A1 | 12/2009 | Stone et al. |
| 2009/0306776 A1 | 12/2009 | Murray |
| 2010/0057109 A1 | 3/2010 | Clerc et al. |
| 2010/0106169 A1 | 4/2010 | Niese et al. |
| 2010/0114137 A1 | 5/2010 | Vidal et al. |
| 2010/0121352 A1 | 5/2010 | Murray et al. |
| 2010/0130990 A1 | 5/2010 | Saliman |
| 2010/0145364 A1 | 6/2010 | Keren et al. |
| 2010/0185232 A1 | 7/2010 | Hughett et al. |
| 2010/0198235 A1 | 8/2010 | Pierce et al. |
| 2010/0217286 A1 | 8/2010 | Gerber et al. |
| 2010/0228271 A1 | 9/2010 | Marshall et al. |
| 2010/0241142 A1 | 9/2010 | Akyuz et al. |
| 2010/0249809 A1 | 9/2010 | Singhatat et al. |
| 2010/0280530 A1 | 11/2010 | Hashiba |
| 2010/0305581 A1 | 12/2010 | Hart |
| 2010/0305583 A1 | 12/2010 | Baird et al. |
| 2011/0022061 A1 | 1/2011 | Orphanos et al. |
| 2011/0022063 A1 | 1/2011 | McClurg et al. |
| 2011/0028998 A1 | 2/2011 | Adams et al. |
| 2011/0060350 A1 | 3/2011 | Powers et al. |
| 2011/0071563 A1 | 3/2011 | Magliani |
| 2011/0087246 A1 | 4/2011 | Saliman et al. |
| 2011/0100173 A1 | 5/2011 | Stone et al. |
| 2011/0112555 A1 | 5/2011 | Overes et al. |
| 2011/0118760 A1 | 5/2011 | Gregoire et al. |
| 2011/0130773 A1 | 6/2011 | Saliman et al. |
| 2011/0152892 A1 | 6/2011 | Saliman et al. |
| 2011/0190815 A1 | 8/2011 | Saliman |
| 2011/0251626 A1 | 10/2011 | Wyman et al. |
| 2011/0270306 A1 | 11/2011 | Denham et al. |
| 2012/0101524 A1 | 4/2012 | Bennett |
| 2012/0303046 A1 | 11/2012 | Stone et al. |
| 2013/0072948 A1 | 3/2013 | States, III et al. |
| 2013/0085512 A1 | 4/2013 | Wyman et al. |
| 2013/0253536 A1 | 9/2013 | Harris et al. |
| 2014/0188136 A1 | 7/2014 | Cournoyer et al. |
| 2014/0222034 A1 | 8/2014 | Saliman |
| 2015/0034694 A1 | 2/2015 | Cappola |
| 2015/0073442 A1 | 3/2015 | Saliman et al. |
| 2015/0157317 A1 | 6/2015 | Bagaoisan et al. |
| 2015/0173742 A1 | 6/2015 | Palese et al. |
| 2015/0173743 A1 | 6/2015 | Palese et al. |
| 2015/0209029 A1 | 7/2015 | Hendricksen et al. |
| 2015/0257756 A1 | 9/2015 | Sauer |
| 2015/0297215 A1 | 10/2015 | Hendricksen et al. |
| 2015/0313589 A1 | 11/2015 | Hendricksen et al. |
| 2016/0302789 A1 | 10/2016 | Hirotsuka et al. |
| 2017/0020512 A1 | 1/2017 | Murillo et al. |
| 2017/0027558 A1 | 2/2017 | Murillo et al. |
| 2017/0119372 A1 | 5/2017 | Peter et al. |
| 2018/0116651 A1 | 5/2018 | Saliman |
| 2018/0125479 A1 | 5/2018 | Saliman et al. |
| 2018/0199931 A1 | 7/2018 | Saliman et al. |
| 2018/0303476 A1 | 10/2018 | Murillo et al. |

FOREIGN PATENT DOCUMENTS

| | | |
|---|---|---|
| CN | 103298503 A | 9/2013 |
| CN | 103717149 A | 4/2014 |
| EP | 0647431 A2 | 4/1995 |
| EP | 2030575 A1 | 3/2009 |
| EP | 2184015 A2 | 5/2010 |
| EP | 2081481 B1 | 11/2015 |
| JP | 3032847 U | 3/1991 |
| JP | 2009138029 A | 6/2009 |
| JP | 2009538190 A | 11/2009 |
| SU | 376089 A | 4/1973 |
| SU | 728848 A1 | 4/1980 |
| SU | 1725847 A1 | 4/1992 |
| WO | WO92/05828 A1 | 4/1992 |
| WO | WO95/13021 A1 | 5/1995 |
| WO | WO98/11825 A1 | 3/1998 |
| WO | WO98/31288 A1 | 7/1998 |
| WO | WO99/34744 A1 | 7/1999 |
| WO | WO99/42036 A1 | 8/1999 |
| WO | WO99/47050 A2 | 9/1999 |
| WO | WO01/56478 A1 | 8/2001 |
| WO | WO02/07607 A1 | 1/2002 |
| WO | WO02/096296 A1 | 12/2002 |
| WO | WO03/077771 A1 | 9/2003 |
| WO | WO2006/001040 A1 | 1/2006 |
| WO | WO2006/040562 A1 | 4/2006 |
| WO | WO2010/141695 A1 | 12/2010 |
| WO | WO2011/057245 A2 | 5/2011 |

OTHER PUBLICATIONS

Asik et al.; Failure strength of repair devices versus meniscus suturing techniques; Knee Surg, Sports Traumatol, Arthrosc; vol. 10; No. 1; pp. 25-29; Jan. 2002.

Arthrex®, Arthrex, Inc., "The Next Generation in Shoulder Repair Technology," Product Brochure from Arthrex, Inc; Naples, Florida, (year of pub. sufficiently earlier than effective US filing date and any foreign priority date) 2007, 22 pages.

ArthroCare® Sportsmedicine, Sunnyvale, CA, SmartStitch® Suture Passing System with the PerfectPasserTM, Product brochure, (year of pub. sufficiently earlier than effective US filing date and any foreign priority date) 2006, 4 pages.

BiPass(TM) Suture Punch, Biomet® Sports Medicine, Inc., accessed Feb. 29, 2008 at <http://www.arthrotek.com/prodpage.cfm?c=0A05&p=090706> 2 pages.

Boenisch et al.; Pull-out strength and stiffness of meniscal repair using absorbable arrows or Ti-Cron vertical and horizontal loop sutures; Amer. J. of Sports Med.; vol. 27; No. 5 pp. 626-631; Sep.-Oct. 1999.

Cayenne Medical; CrossFix® II System (product webpage); 4 pgs.; downloaded Nov. 21, 2011 (www.cayennemedical.com/products/crossfix/).

CETERIX; Novocut suture manager; retrieved from the internet (https://web.archive.org/web/20150314071511/http://www.ceterix.com:80/im-a-physician/products/) on Oct. 11, 2017; 1 page; Mar. 12, 2015.

CETERIX; Novocut suture manager; retrieved from the internet (https://www.youtube.com/watch?v=6txqBJxvnuA) on Oct. 11, 2017; 1 page; Mar. 5, 2015.

Covidien Surgical; Endo Stitch 10 mm Suturing Device; accessed Dec. 4, 2012 at <http://www.autosuture.com/autosuture/pagebuilder.aspx?topicID=7407&breadcrumbs=0:63659,30691:0,309:0> 2 pgs.

Depuy Mitek, Inc; Raynham, MA, "Versalok Surgical Technique for Rotator Cuff Repair: The next generation in rotator cuff repair," Product brochure, (year of pub. sufficiently earlier than effective US filing date and any foreign priority date) 2007, 18 pages.

dictionary.com; Adjacent (definition); 5 pgs.; retrieved from the internet (http://www.dictionary.com/browse/adjacent) on Apr. 5, 2016.

Duerig, T. et al., "An overview of nitinol medical applications" Materials Science and Engineering A273-275, pp. 149-160; May 1999.

(56) References Cited

OTHER PUBLICATIONS

Linvatec Conmed Company, Largo, Florida, Product descriptions B17-19, B21; Tissue Repair Systems, Tissue Repair Accessories, and Master Arthroscopy Shoulder Instrument Set, (printed on or before Aug. 2007), 4 pages.

Ma et al; "Biomechanical Evaluation of Arthroscopic Rotator Cuff Stitches," J Bone Joint Surg Am, Jun. 2004; vol. 86(6):1211-1216.

MEDSFERA; Suturing devices; accessed Dec. 4, 2012 at <http://www.medsfera.ru/shiv.html> 13 pages.

Nho et al; "Biomechanical fixation in Arthroscopic Rotator Cuff Repair," Arthroscopy: J of Arthroscop and Related Surg; vol. 23. No. 1, Jan. 2007: pp. 94-102.

Nord et al.; Posterior lateral meniscal root tears and meniscal repair; Orthopedics Today; 5 pgs; Nov. 2010; retrieved from the internet on Aug. 21, 2014 (http://www.healio.com/orthopedics/arthroscopy/news/print/orthopedics-today/%7B1b52a700-e986-4524-ac7d-6043c9799e15%7D/posterior-lateral-meniscal-root-tears-and-meniscal-repair).

Rimmer et al.; Failure Strength of Different Meniscal Suturing Techniques; Arthroscopy: The Journal of Arthroscopic and Related Surgery; vol. 11; No. 2; pp. 146-150; Apr. 1995.

Schneeberger, et al; "Mechanical Strength of Arthroscopic Rotator Cuff Repair Techniques: An in Vitro Study," J Bone Joint Surg Am., Dec. 2002; 84:2152-2160.

Smith&Nephew; Fast-Fix Meniscal Repair System (product webpage); 4 pgs.; downloaded Nov. 21, 2011 (http://endo.smith-nephew.com/fr/node.asp?NodeId=3562).

Strobel; Manual of Arthroscopic Surgery (1st Edition); Springer Verlag, Hiedelberg ©2002; pp. 127-129; Dec. 15, 2001.

USS SportsMedicine ArthoSewTM Single Use Automated Suturing Device with 8.6 mm ArthroPort Cannula Set, Instructions for Use, <http:www.uss-sportsmed.com/imageServer.aspx? contentID=5020 &contenttype=application/pdf> accessed Apr. 25, 2007, 2 pages.

USS SportsMedicine ArthroSewTM Suturing Device, <http://www.uss-sportsmed.com/SportsMedicine/pageBuilder.aspx?webPageID=0&topicID=7141&xsl=xsl/productPagePrint.xsl>, product description, accessed Apr. 25, 2007, 3 pages.

George et al., U.S. Appl. No. 16/208,526 entitled "Arthroscopic knot pusher and suture cutter," filed Dec. 3, 2018.

\* cited by examiner

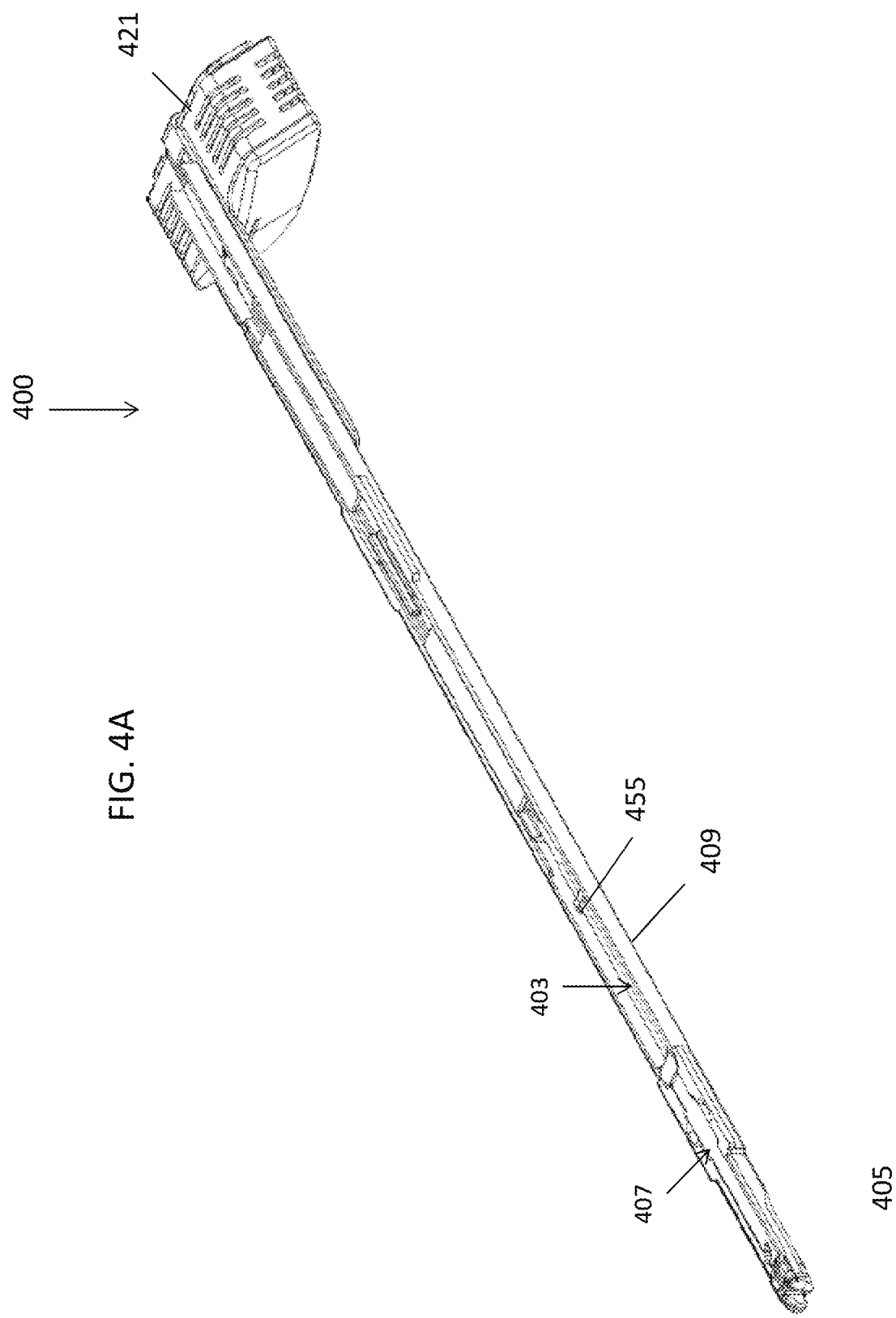

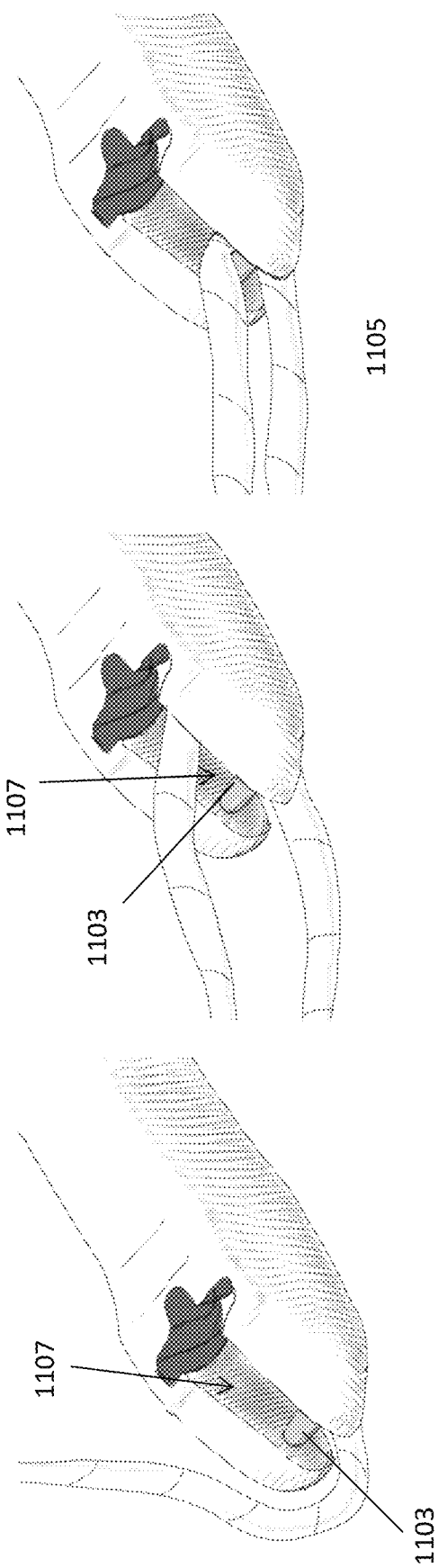
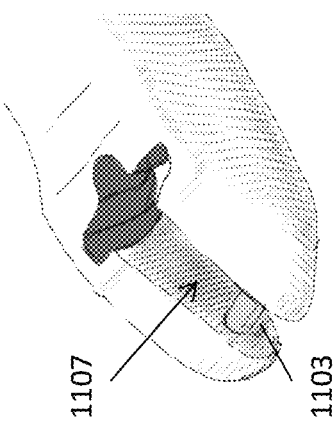
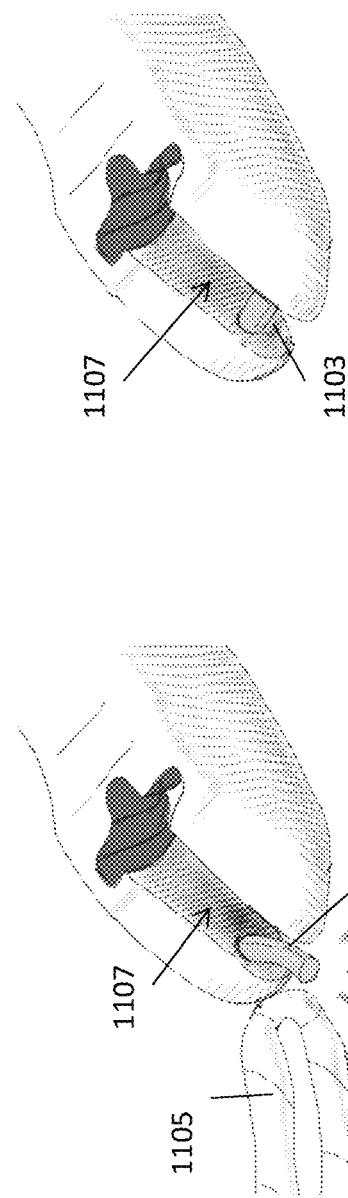
FIG. 11D  FIG. 11E  FIG. 11F  FIG. 11G  FIG. 11H 1207 — This is the end of suture 1 that meets up with the middle of the suture and transitions into suture 2

1201 — Terminal end of suture 1 (End not shown in image. End would be tucked into lower jaw in actual implementation.)

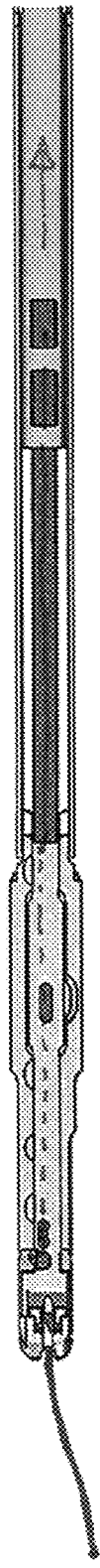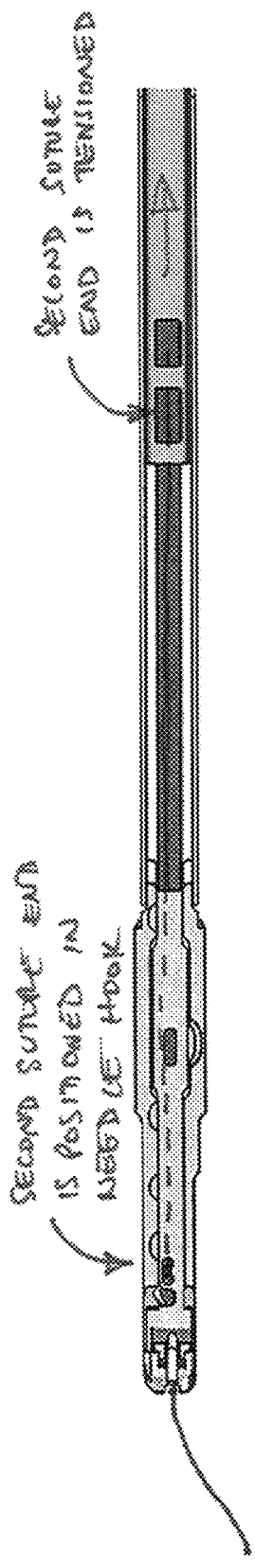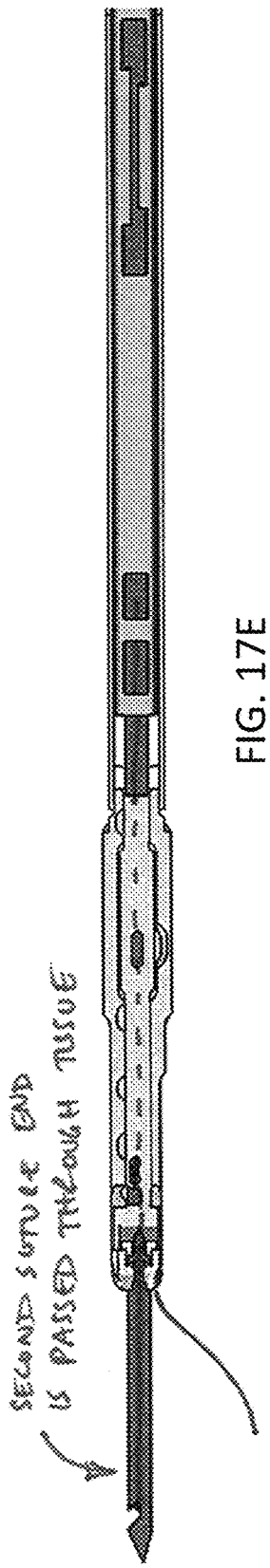

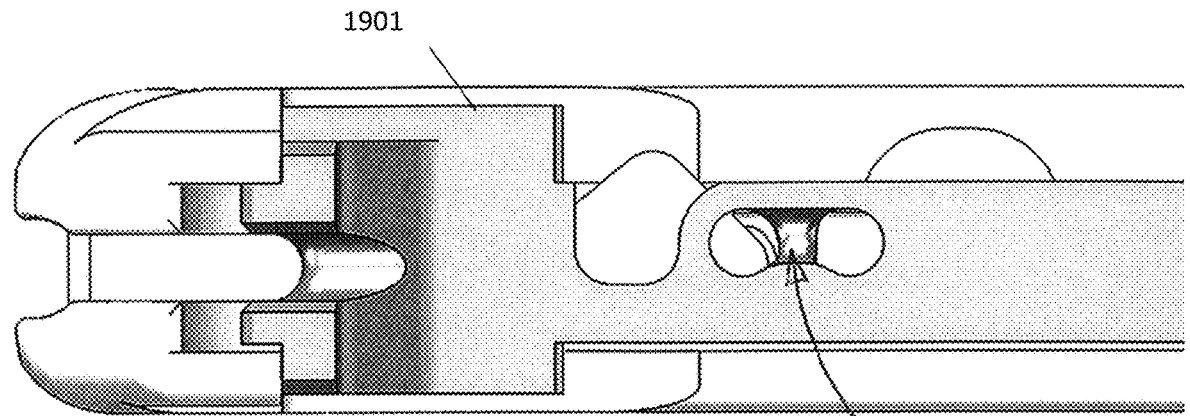
FIG. 19A  1905 "SUTURE GUIDE" FEATURE
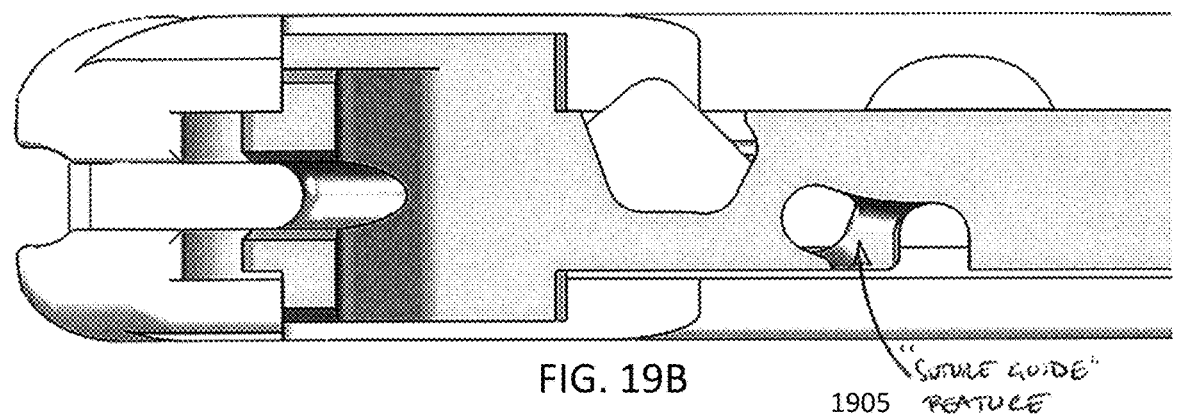
FIG. 19B  1905 "SUTURE GUIDE" FEATURE
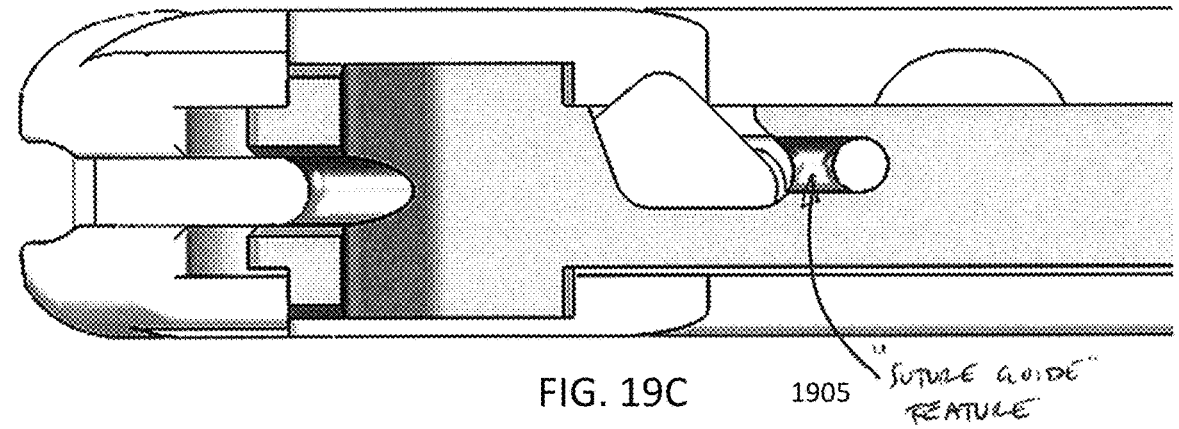
FIG. 19C  1905 "SUTURE GUIDE" FEATURE

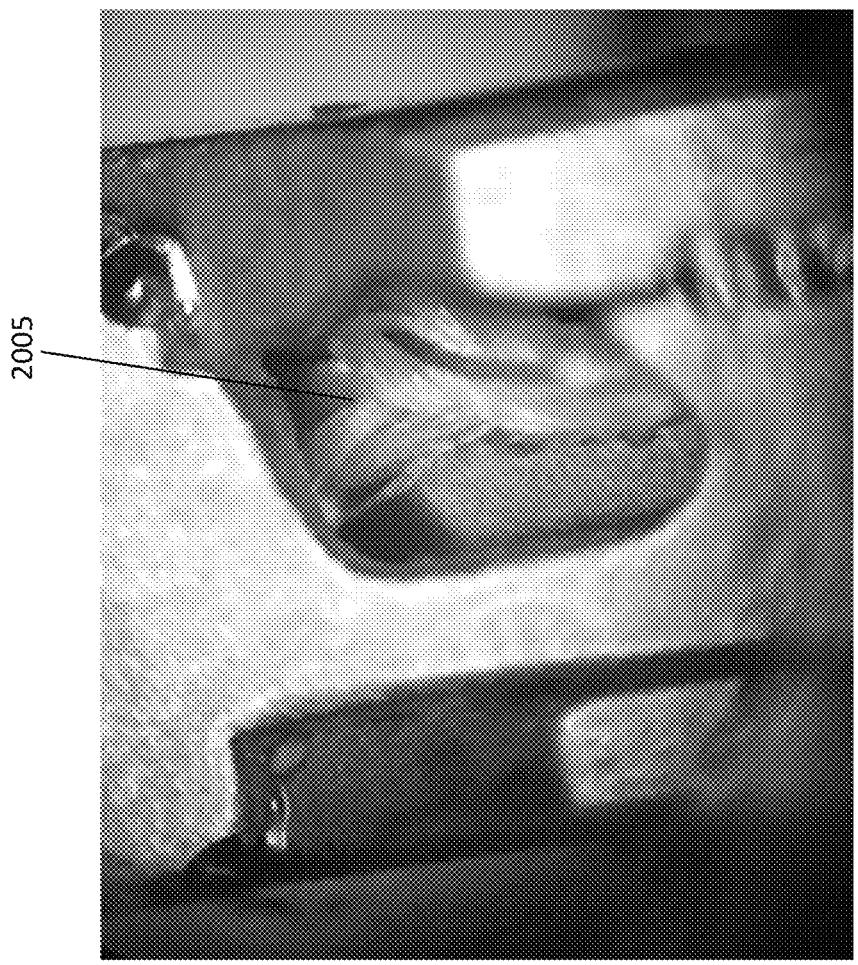
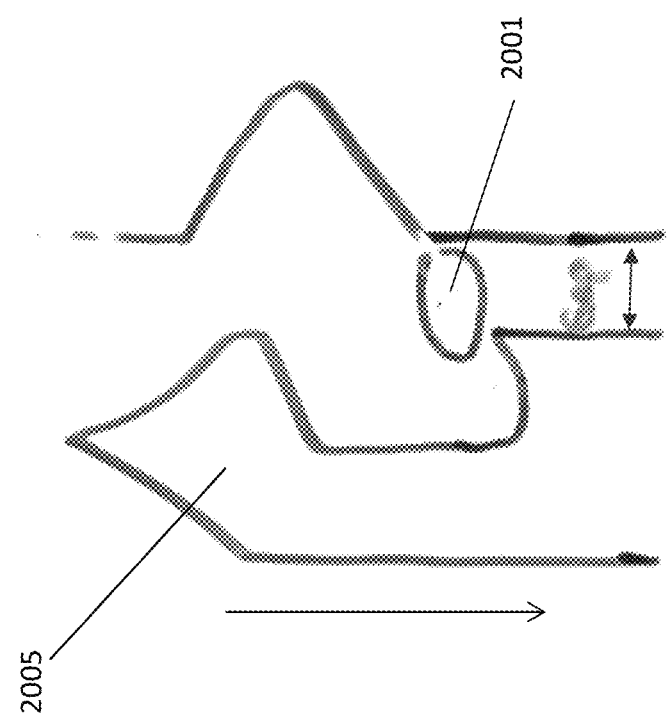
FIG. 20B
FIG. 20A ions Ser. No. 15/216,482, filed Jul. 21, 2016, titled "AUTO-
AUTOMATICALLY RELOADING SUTURE PASSER DEVICES THAT PREVENT ENTANGLEMENT

CROSS REFERENCE TO RELATED APPLICATIONS

This application is a continuation of U.S. patent application Ser. No. 15/216,482, filed Jul. 21, 2016, titled "AUTOMATICALLY RELOADING SUTURE PASSER DEVICES THAT PREVENT ENTANGLEMENT," which application claims priority to U.S. Provisional Patent Application No. 62/195,141, filed Jul. 21, 2015, titled "AUTOMATICALLY RELOADING SUTURE PASSER DEVICES THAT PREVENT ENTANGLEMENT," each of which is herein incorporated by reference in its entirety.

This patent application may be related to U.S. patent application Ser. No. 14/572,485, titled "AUTOMATICALLY RELOADING SUTURE PASSER DEVICES AND METHODS," filed Dec. 16, 2014, now U.S. Pat. No. 9,492,162, which claims priority as a continuation-in-part to International Patent Application No. PCT/US2014/030137, titled "SUTURE PASSER DEVICES AND METHODS," filed Mar. 17, 2014, Publication No. WO 2014/145381, and U.S. Provisional Patent Application No. 61/916,735, titled "AUTOMATICALLY RELOADING SUTURE PASSER DEVICES AND METHODS," filed Dec. 16, 2013. Each of these applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The methods and apparatuses (e.g., devices and systems) described herein may be used to suture tissue, particularly in difficult to access regions. In particular, described herein are preloaded and automatically re-loading suture passers that are adapted to include a gate, guide, or shield on one of the jaws of the suture passer, and methods of operating such suture passers for surgical use including repairing tissue.

BACKGROUND

Suturing of tissue during surgical procedures is time consuming and can be particularly challenging in difficult to access body regions and regions that have limited clearance, such as regions partially surrounded or covered by bone. For many surgical procedures, it is necessary to make a large opening in the human body to expose the area requiring surgical repair. However, in many cases, accessing the tissue in this manner is undesirable, increasing recovery time, and exposing the patient to greater risk of infection.

Suturing instruments ("suture passers" or "suturing devices") have been developed to assist in accessing and treating internal body regions, and to generally assist a physician in repairing tissue. Although many such devices are available for endoscopic and/or percutaneous use, these devices suffer from a variety of problems, including limited ability to navigate and be operated within the tight confines of the body, risk of injury to adjacent structures, problems controlling the position and/or condition of the tissue before, during, and after passing the suture, and difficulties loading the suture into the device, particularly for threading multiple suture loops.

For example, some surgical instruments used in endoscopic procedures are limited by the manner in which they access the areas of the human body in need of repair. In particular, the instruments may not be able to access tissue or organs located deep within the body or that are in some way obstructed. In addition, many of the instruments are limited by the way they grasp tissue, apply a suture, or recapture the needle and suture. Furthermore, many of the instruments are complicated and expensive to use due to the numerous parts and/or subassemblies required to make them function properly. Suturing remains a delicate and time-consuming aspect of most surgeries, including those performed endoscopically.

The knee joint is one example of a tissue region that is notoriously difficult to access. For example, the meniscus is a C-shaped piece of fibrocartilage which is located at the peripheral aspect of the joint (e.g., the knee) between the condyles of the femur and the tibia on the lateral and medial sides of the knee. The central two-thirds of the meniscus has a limited blood supply while the peripheral one third typically has an excellent blood supply. Acute traumatic events commonly cause meniscus tears in younger patients while degenerative tears are more common in older patients as the menisci become increasingly brittle with age. Typically, when the meniscus is damaged, a torn piece of meniscus may move in an abnormal fashion inside the joint, which may lead to pain and loss of function of the joint. Early arthritis can also occur due to these tears as abnormal mechanical movement of torn meniscal tissue and the loss of the shock absorbing properties of the meniscus lead to destruction of the surrounding articular cartilage. Occasionally, it is possible to repair a torn meniscus. While this may be done arthroscopically, surgical repair using a suture has proven difficult to perform because of the hard-to-reach nature of the region and the difficulty in placing sutures in a way that compresses and secures the torn surfaces.

The meniscus of the knee is just one example of a tissue that is difficult to access so that appropriate suturing may be performed. FIG. 2 illustrate the anatomy of the meniscus in the context of a knee joint. As shown in FIG. 2 the capsule region (the outer edge region of the meniscus) is vascularized. Blood enters the meniscus from the menisculocapsular region 291 lateral to the meniscus. A typical meniscus has a flattened bottom 298 (inferior surface or side adjacent to the tibia) and a concave top 296 (superior surface or side, adjacent to the femur), and the outer cross-sectional shape may be somewhat triangular, with a meniscus tip region 294. The outer edge of the meniscus transitions into the capsule 291. The meniscus may include circumferential fibers extending along the curved length of the meniscus, as well as radial fibers, and more randomly distributed mesh network fibers. Because of the relative orientations and structures of these fibers, and the predominance of circumferential fibers, it may be beneficial to repair the meniscus by suturing radially (vertically) rather than longitudinally or horizontally, depending on the type of repair being performed. Most prior art devices for suturing or repairing the meniscus are only capable of reliably repairing vertical/longitudinal tears. Such devices are not typically useful for repairing radial or horizontal tears. Furthermore, prior art device mechanisms have a high inherent risk for iatrogenic injury to surrounding neurovascular structures and chondral surfaces.

Thus, there is a need for methods and apparatuses (e.g., devices and systems) for suturing tissue, particularly tissue in difficult to access regions of the body including the joints (shoulder, knee, etc.). In particularly, it has proven useful to provide a device that may simply and reliably reach and pass sutures within otherwise inaccessible tissue regions. Such devices should be extremely low profile, and may be adapted or otherwise configured to fit in the tight spaces of the joints. Finally, would be useful to provide suturing apparatuses that allow selective and specific penetration of the tissue by both the tissue penetrator (needle element) and a jaw so that complex (including right-angled) suturing patterns may be achieved.

Although a suture passers that may be preloaded or reloadable with one or more sutures have been suggested, these devices typically require manual loading, activation and control of the suture in order to operate. Suture passers that could pass two (or more) lengths of suture, including two or more portions of the same suture, without requiring manual loading or reloading, would be highly advantageous, as they could increase the ease of suturing and reduce the time required for surgical procedures, as well as elimination or reducing a possible source of operational error.

To address these needs, U.S. application Ser. No. 14/572,485 (incorporated by reference above) describes preloaded suture passers that may pass multiple lengths (bights) of one or more suture. Unfortunately, when passing multiple lengths of suture using a preloaded suture passer, one failure mode is the recapture or entangle the previously passed length of suture, when passing the second length of suture.

Described herein are preloaded suture passers, preloaded cartridges for suture passers, and methods of operating such apparatuses to repair tissue capable of automatically passing a preloaded length of suture and automatically preloading with a second length of suture, while preventing entanglement and/or entrapment of the first bight. These apparatuses (e.g., devices, including suture passers, and cartridges for suture passers, and systems of suture passers) and the methods of operating them described herein may be used to access difficult-to reach tissues.

The apparatuses and methods described herein may address the needs and potential benefits briefly discussed above.

SUMMARY OF THE DISCLOSURE

Described herein are preloaded cartridges for suture passers, preloaded suture passers, systems including preloaded suture passers and/or cartridges for suture passers, and methods of operating any of these to pass multiple lengths or suture and/or repair tissue, having a gate, shield, or otherwise configured to prevent a length of suture from re-entering a channel in the preloaded cartridge (e.g., in the jaw formed by the preloaded cartridge) and being entrapped by the tissue penetrator within the preloaded cartridge. In particular, described herein are preloaded cartridges in which a first length of suture is preloaded into the tissue penetrator (e.g., needle) and, after passing the first length of suture, the cartridge automatically applies tension to load a second length of suture into the tissue penetrator; the jaw formed by the preloaded cartridge includes a gate that prevents a length of suture outside of the cartridge from reentering the cartridge and being ensnared/entangled by the tissue penetrator.

Also described herein are suture passers that include a jaw member adapted, e.g., by including a gate at the distal end to prevent a length of suture from re-entering the distal end of the suture passer and becoming entrapped and/or captured and/or entangled by the tissue penetrator, which may be loaded or configured to be loaded with a second length of suture. In general, the distal end of the jaw member (e.g., a second or lower jaw member) typically includes a channel extending proximally from the distal end region. The channel may be continuous with a channel in which the tissue penetrator resides or slides so that it can extend out of and retract into the jaw member to push a loop (bight) of suture through the tissue and engage another jaw (e.g., a first or upper jaw) on an opposite side of the tissue. The gate is generally positioned at the distal end of this channel in the jaw housing the tissue penetrator. In some variations the gate is a deflectable gate (e.g. a deflectable pin, member, arm, etc.) that extends across the channel opening. A deflectable gate is typically configured to open in a one direction (e.g., outwards relative to the channel) and allow a length, loop or bight of suture to be pushed out of the channel, but be closed and resist opening in the opposite direction (e.g., inwards relative to the channel). Thus, the gate may be a deflectable gate that is configured to open in one direction only (e.g., outwardly) but remain closed in the opposite direction. In some variations, the gate may be configured to rotate or pivot to open and close, and may be prevented from rotating/pivoting inwards. In some variations the gate is bendable so that it can be deflected by changing shape (elastically) or bending on an elastic hinge region, to open outwards and close to prevent a suture from entering the channel.

In some variations the distal end of the jaw is configured to prevent reentry of a suture length by having a narrow and/or off-axis opening at the distal end of the channel. For example, in some variations the distal end of the jaw (e.g., the lower jaw housing the tissue penetrator) is configured to have a rounded/curved distal surface with a narrow channel opening. In contrast, the distal end of the channel within the jaw may be shaped to encourage a length of suture to exit (but not reenter) the narrow opening at the distal end of the channel.

In some variations, the distal end of the jaw is configured so that the opening into the distal portion of the channel is offset on a side (e.g., a lateral side) of the jaw, making it much less likely that a suture would be recaptured into the channel an entangled by the tissue penetrator.

Any of the suture passer devices described herein, including a gate to prevent entanglement of a length of suture as mentioned above, may include a jaw that is part of or includes a cartridge. A cartridge may be configured to be fully-enclosed, though with opening from which the loaded tissue penetrator may be extended and retracted. The cartridge may be configured as a jaw for use with a suture passer, or may include a jaw region. The cartridge may be coupled to a durable (e.g., reusable) suture passer; the cartridge may be disposable or recyclable. The cartridge may be coupleable to a suture passer, and may be slideable or adjustable once on the suture passer. The suture passer may engage with the cartridge to control the position of the jaw portion of the suture passer and/or the tissue penetrator.

In any of the apparatuses and methods described herein, the tissue penetrator may be preloaded with a first bight of suture in a suture engagement portion of the tissue penetrator, and may also include a second bight of suture positioned to be loaded into the tissue engagement portion when the first bight has been passed by the suture passer. The apparatus may include a releasable hold securing a portion (such as an end region) of the suture to the tissue penetrator so that this portion of the suture can move with the tissue penetrator; sliding the tissue penetrator may therefore tension (e.g., pull taught) a region of suture between the portion held by the releasable hold and a second bight of suture. If the suture engagement portion of the tissue penetrator (needle) is empty, the tension can pull the second bight of suture into the tissue engagement region for automatically reloading the second bight into onto the tissue penetrator. The second bight of suture is typically held in a suture holding region that remains fixed relative to the tissue penetrator.

A replaceable jaw cartridge that is preloaded with suture for use with a suture passer device may be configured to prevent entanglement and/or recapture of a length of suture by the tissue penetrator. For example a replaceable jaw cartridge may include: a jaw housing configured to releasably engage the suture passer device, the jaw housing having a channel extending proximally from a distal end region of the jaw housing; a tissue penetrator configured to slide distally and proximally within the jaw housing; a suture within the jaw housing, the suture comprising a first bight region loaded in a suture engagement region at a distal end region of the tissue penetrator, and a second bight region loaded in a suture holding region within the jaw housing; and a gate at the distal end region of the jaw housing, wherein the gate is configured to open distally to allow the release of the suture from the channel, and to close to prevent a portion of the suture from re-entering the channel.

The gate may comprises a deflectable pin. In some variations, the gate comprises a turnstile mechanism. The jaw housing may be configured to completely enclose the suture and tissue penetrator until the tissue penetrator is extended from the jaw housing. The jaw housing may comprise a keyed connector configured for coupling with an elongate member of the suture passer device.

A suture passer apparatus (e.g., device or system) with a preloaded suture may be configured to prevent entanglement and/or recapture of a length of suture that has already been passed by the apparatus and may include: an elongate body extending distally and proximally; a first jaw coupled to a distal end of the elongate body; a second jaw having a channel extending proximally from a distal end region of the second jaw; a tissue penetrator configured to slide distally and proximally within the second jaw; a suture within the second jaw, the suture comprising a first bight region loaded in a suture engagement region at a distal end region of the tissue penetrator, and a second bight region loaded in a suture holding region within the second jaw; and a gate at the distal end region of the jaw housing, wherein the gate is configured to open distally to allow the release of the suture from the channel, and to close to prevent a portion of the suture from re-entering the channel. As mentioned, above the gate may comprise a deflectable pin (e.g., that opens in one direction, to allow suture to exit, but not enter, the channel), for example, the gate may comprise a turnstile mechanism.

The second jaw may be configured to enclose the tissue penetrator until the tissue penetrator is extended from the jaw housing.

As will be described in more detail below, in any of these apparatuses, the first jaw may be configured to pivot relative to the elongate body and wherein the second jaw may be configured to slide axially relative to the elongate body.

Any of the apparatuses described herein (including preloaded cartridges, systems using preloaded cartridges, or integrated preloaded suture passers) may also include in the enclosure or housing holding the tissue penetrator and suture, one or more suture management elements such as guides, funnels, storage regions, spools, etc. to direct or hold the suture.

Any of the apparatuses described herein may include a deflection surface at or near an exit through the jaw housing, wherein the deflection surface is configured to deflect the tissue penetrator away from the jaw housing as the tissue penetrator slides distally out of the exit. The tissue penetrator may be generally configured to exit laterally from the side of the second jaw (e.g., the replaceable jaw cartridge). The tissue penetrator may be an elongate, thin, flat, or otherwise bendable structure. The tissue penetrator may be a metal (e.g., a shape memory alloy such as Nitinol) that is capable of being stored in a relatively straight configuration, and deflected one or more times when passing a length of suture, then restored to the relatively straight configuration when retracted back into the jaw housing.

A jaw housing may be configured to completely enclose the suture and tissue penetrator until the tissue penetrator is extended from the jaw housing. The jaw housing may be completely closed or it may include one or more openings. The jaw housing may include a region configured as a jaw. This jaw region may be configured to mate with another jaw region of a suture passer, such as an upper or pivoting jaw; the two jaws may form a distal-facing opening that can be opened and closed relative to each other to partially surround and/or grip target tissue to be sutured. Thus, the jaw housing may include a tissue-engaging surface that can be positioned opposite another jaw surface on the suture passer. The tissue-engaging surface may be smooth, or it may include a texture or geometry that aids in grasping and/or holding tissue.

In variations in which the cartridge is replaceably coupleable to a suture passer, the suture passer may not be competent to pass suture without a cartridge attached; for example durable portion of the suture passer may include a handle, controls, an elongate body and a fixed or rotatable upper jaw member, but may lack a lower jaw (e.g., a sliding lower jaw) and/or a tissue penetrator. Such suture passers may be referred to herein as durable (or reusable) suture passers, because they can be re-sterilized and reused, or generally used with multiple replaceable jaw cartridges.

Thus, in some variations the cartridge includes elements that help connect the cartridge to the durable suture passer. For example, a jaw housing may include a keyed connector configured for coupling with an elongate member of the suture passer device.

In general, the apparatuses described herein include a holding region (suture holding region) for holding the second bight of suture that will be automatically re-loaded into the suture engagement region of the tissue penetrator. For example, any of these apparatuses may include a suture holding region that is configured as a notched region between the tissue penetrator and an inner surface of the jaw housing. The suture holding region may act in conjunction with the releasable hold on the tissue penetrator to hold the length of suture between the suture holding region and the reliable hold in tension. In some variations the suture holding region pinches or grasps the second bight region of the suture. In other variations the suture holding region does not apply any force to the second bight region; because the second bight region bends over/within the suture holding region (e.g., a notch forming the suture holding region) the second bight region may be held in the suture holding region.

In general, the suture holding region may be configured to be positioned opposite from the suture engagement region of the tissue penetrator when the tissue penetrator is withdrawn proximally within the jaw housing. Thus, tension on the second bight region (e.g. from the releasable hold) may allow it to slide from the suture holding region into the suture engagement region when the first bight is no longer in the suture holding region and when the tissue penetrator has been positioned within the housing to align the suture engagement region with the suture holding region.

Any appropriate suture may be used, including synthetic, natural or hybrid sutures. The suture may be monofilament or woven, and may be coated or uncoated. Although in some variations different suture may be used, in general the first and second bights of suture may be formed from different regions of the same suture. For example, the first bight region may be formed as a bend in the suture located near a distal end of the suture and the second bight region may be formed as a bend in the suture located near the proximal end of the suture.

In general, a releasable hold is attached to the tissue penetrator and moves with the tissue penetrator; the releasable hold typically holds an end region of a suture against the tissue penetrator as it moves and holds the end region relatively fixed to the tissue penetrator, providing tension to the pull the second bight suture to load it into the tissue penetrator. If the force (tension) on this length of suture exceeds a threshold (e.g., a release threshold), the releasable hold will release the suture; in some variations the suture is not completely released above the threshold, but the releasable hold continues to apply a holding force to the end region of the suture that is less than the release force. In some variations the releasable hold stops applying a holding force when the tension exceeds the release threshold. Any appropriate releasable hold may be used. In general, the releasable hold holds a portion of the suture against the tissue penetrator (needle). The releasable hold may push, press, clamp, pinch, bind, or otherwise temporarily secure the suture against the suture passer. For example, a releasable hold may comprise one or more of: an O-ring, a clip, a friction releasable hold, a band, a clamp, a frangible hold, a wax hold, and a releasable adhesive. The releasable hold may include multiple holding sites (e.g., two or more mechanical holding sites, a mechanical holding site and an adhesive holding site, etc.). In general, the releasable hold is positioned proximally on the tissue penetrator relative to the suture engagement region (which may be positioned near the distal tip of the tissue penetrator); the spacing from the distal tip/suture engagement region is typically greater than the distance traveled by the tip of the tissue penetrator so that the releasable hold remains within the housing during normal operation. Although the releasable hold is typically configured to attached to and move with the tissue penetrator, so as to hold an end portion of the suture fixed to the tissue penetrator, in some variations the releasable hold may slide or be moved on/along the tissue penetrator. In other variations the releasably hold may be fixedly attached to the tissue penetrator.

The needle may also be adapted to help releasable secure a portion of the suture with the suture engagement region. For example, the tissue penetrator may be bent or shaped to help pinch the suture against the releasable hold. In some variations the region of suture may also be configured to engage the releasable hold (e.g., including a knot, aglet, ferrule, etc.).

Any component that couples with (and slides with) the tissue penetrator may be configured as a releasable hold. For example a needle sled (sled) may be configured as a releasable hold. In general, the tissue penetrator within the apparatus may be a sled distally/proximally and extended from and retracted back into the jaw housing (e.g., lower jaw housing, cartridge housing, etc.). Thus, the jaw housing may also include/enclose a sled (e.g., needle sled) configured to couple with the tissue penetrator to facilitate sliding of the tissue penetrator within the jaw cartridge. In variations in which the jaw cartridge is replaceably coupled to a durable suture passer, either or both the tissue penetrator and/or the needle sled may couple with a shaft in the durable suture passer that is also connected to a control on a handle region to control the sliding (extension/retraction) of the suture passer. The needle engagement region may be a keyed region that allows pushing and/or pulling of the tissue penetrator within and out of/into the housing. The needle may be actuated independently of any sliding of the jaw housing relative to the durable suture passer, in variations in which the jaw housing (forming a second or lower jaw) may be slide/moved axially and distally relative to the other jaw member of the suture passer. In some variation the needle and the lower jaw may be moved in conjugate motion.

The sled may be configured as a releasable hold, so that the releasable is part of the sled. For example, the sled may from one or more narrow gap regions into which an end portion of suture may be pinched against the body of the tissue penetrator when the tissue penetrator is coupled with the sled and loaded with suture. In some variations the distal end portion of the sled comprise one or more such gap regions for holding an end portion of the suture. In some variations the sled is configured to couple with the tissue penetrator and releasable hold the end portion of the suture against the tissue penetrator. The tissue penetrator may be bent or curved (e.g., by the sled) to help hold the end region of the suture against the tissue penetrator.

In variations of the apparatus in which the tissue penetrator couples directly to an actuator to slide the tissue penetrator, the engagement between the tissue penetrator and the actuator (push/pull rod, shaft, etc.) may be configured as a releasable hold. Alternatively, a separate releasable hold may be coupled to the tissue penetrator.

The housing (e.g., jaw housing) may also include a storage region for storing the length within the housing. For example, the apparatus may include a suture capsule region configured to hold a portion of the suture. The storage capsule region may be at the proximal end of the apparatus. For example, in variations in which the first and second bight are formed of the proximal and distal end regions of a single suture, the region of suture between the first and second bight may extend proximally along the shaft of the jaw housing to a suture capsule at the proximal end that has an enlarged hollow allowing storage of this intermediate region of suture until it is drawn out of the distal end of the housing when passing the suture to the opposite jaw.

In variations in which the jaw housing is configured as part of a cartridge, the apparatus may include a connector configured to couple the jaw cartridge to the suture passer device and to uncouple the jaw cartridge from the suture passer device. For example, the jaw housing may include keyed regions, such as one or more projections (e.g., flanges, pins, bumps, etc.), to engage with a recess region in the durable suture passer device, or one or more receiving regions (e.g., channels, slots, etc.) to receive projecting portions of the suture passer device, or both.

In some variations, the jaw cartridge includes a suture guide within the jaw housing positioned intermediate of the distal end of the jaw housing and the releasable hold. For example, the housing may include or hold a funnel or channel in which the suture passes, which may help guide the suture so that the movement of the tissue penetrator within the housing does not undesirably engage (e.g., tangle) the suture.

As mentioned, the jaw housing and/or the entire jaw cartridge may slideably engage with a durable suture passer device so that jaw member portion of the jaw housing slides distally to proximally along the long axis of the suture passer, in contrast with and independently of an upper jaw on the durable suture passer, which in some variations pivots relative to the long (distal-to-proximal) axis. For example, the jaw housing may be configured to couple to and uncouple from a durable suture passer to form a sliding lower jaw member on the suture passer so that the tissue penetrator can extend from the jaw housing to an upper jaw member.

Also described herein are methods of operating any of the apparatuses described. For example, described herein are methods of operating a suture passer that is preloaded with a suture. A method of operating a suture passer may include: forming a distal-facing opening between a first jaw of the suture passer and a second jaw; extending a distal tip of a tissue penetrator across the distal-facing opening from within the second jaw, wherein the tissue penetrator comprises a suture engagement region that is preloaded with a first bight region of the suture; retracting the distal tip of the tissue penetrator into the second jaw; withdrawing the tissue penetrator distally within the second jaw to tension the suture between an end region of the suture that is held by a releasable hold on the tissue penetrator and a second bight region of the suture, so that the second bight region is drawn into the suture engagement region of the tissue penetrator; and extending the distal tip of the tissue penetrator from the second jaw and across the distal-facing opening, wherein the tissue penetrator is carrying the second bight region of the suture. The method may include the step of passing a length of suture out of a channel in the second jaw in a first direction, but preventing (e.g., via any of the gates described herein) a length of suture from entering the channel, thereby preventing a length of suture from getting entangled in the lower jaw.

The method may also include coupling a replaceable second jaw, configured as a jaw cartridge, to an elongate body of the suture passer, wherein the suture passer includes a first jaw pivotally coupled to a distal end region of the elongate body.

The step of forming a distal-facing opening between the first jaw of and a second jaw may comprise sliding the second jaw distally relative to the elongate body to form the distal-facing opening between a distal end region of the second jaw and the first jaw.

The method may also include uncoupling the jaw cartridge from the suture passer.

In some of the methods of operating the apparatuses described herein, the method may also include pivoting the first jaw relative to the elongate body and sliding the second jaw distally to form the distal-facing opening, and/or passing the first bight region of the suture to the first jaw.

Also described herein are suture passers that have extremely low profiles. In some variations the devices are adapted so that the lower jaw has a substantially lower profile by reducing the arc of the needle exit, by axially separating the lower jaw into a first (e.g., proximal) region controlling the axial translation (motion) of the lower jaw and a second (e.g., distal) region that contains all of the features of the tissue penetrator pathway; these different regions may have different heights, allowing nesting into the shaft particularly near the proximal end of the device.

Although this disclosure is divided up into parts, indication different features, any of these parts or individual features may be used alone or in combination with any other parts or features described herein or incorporated by reference.

In general, the first or second jaw may hold the tissue penetrator within an internal passage, and the tissue penetrator may be extended between the distal-facing opening to push and/or pull a suture between the first and second jaws. The tissue penetrator may be any appropriate material, but shape memory materials (e.g., shape memory alloys, plastics, etc.) are of particularly interest. The tissue penetrator may have a sharp (e.g., pointed, beveled, etc.) distal tip for penetrating tissue, which may be symmetric (e.g., having a central sharp point in the mid-line of the long axis) or asymmetric (having a sharp point that is not in the mid-line of the tissue penetrator). The tissue penetrator may be biased (e.g., pre-bent) in a curve or bend. In general the tissue penetrator (e.g., needle) may extend from a side region of the first or second jaw, extend across the distal-facing opening, and connect to an opening on the side region of the opposite (e.g., second or first) jaw from which it extends. This opening may include a suture capture region that holds the suture passed by the tissue penetrator. The suture capture region may be a suture retainer that holds the suture when passed by the tissue penetrator. For example, the suture retainer may be a deflecting or deflectable clamping region, a hook, or the like.

In general, the tissue penetrator may be configured to bend as it extends from the jaw and across the distal-facing opening. For example, the tissue penetrator may be pre-biased to assume a bent or curved configuration as it extends from within a jaw. Thus, the tissue penetrator may extend approximately perpendicular to the side of the jaw housing it. In some variations the jaw includes a tissue penetrator deflection (e.g., ramped) region that helps deflect the jaw. In some variations the jaw housing the tissue penetrator does not include a deflector.

For example, described herein are suture passers for forming a loop of suture around a target tissue, the suture passer comprising: an elongate body extending distally and proximally along a long axis; a first jaw extending from a distal end region of the elongate body wherein the first jaw is bent or bendable at an angle relative to the long axis; a second jaw configured to slide axially along the long axis distally and proximally relative to the elongate body, further wherein the first jaw and the second jaw form a distal-facing opening when the second jaw is extended distally and wherein the second jaw is retractable proximally so that it does not form the distal-facing opening with the first jaw; a tissue penetrator configured to extend across the distal-facing opening between the first jaw and the second jaw to pass a suture there between; and a plate having a keyhole capture region, wherein the keyhole capture region comprise a capture pathway including a channel extending through the plate and a release pathway, wherein the capture pathway is connected to the release pathway by at least one bend, further wherein the plate is coupled to the first jaw so that it may receive a suture from the tissue penetrator extending from the second jaw. The capture pathway may comprise an opening mouth at an edge of the plate that tapers to a narrower channel before the release pathway. In some variations, the release pathway comprises an enlarged opening having a larger diameter than the region of the capture pathway adjacent to the release pathway. The bend may be configured to retain the suture immediately after it is passed into the keyhole capture region by the tissue penetrator.

Also described herein are apparatuses and method of operating them that include are devices having a jaw that is adapted to fit into a tight region of the body such as the knee joint, and particularly around the meniscus of the knee. The jaw member (e.g., upper jaw member) may be adapted to be bent (e.g., hinged) relative to a long axis of the (e.g., elongate body of the) apparatus, and may include a proximal region closest to the end of the jaw hinged to the elongate body of the apparatus that is curved on an upper distally-extending surface and is relatively flat on the lower distally-extending surface that contacts the tissue. The flat lower surface may prevent the tissue from being forced out from between the jaws as the upper jaw is closed towards a lower jaw; the curved upper surface may allow the upper jaw member to be positioned easily between the target tissue and a curved bone surface such as the femur (e.g., the head region of the femur).

Tissue penetrators (e.g., needles) may also or alternatively be adapted so that the distal tip region is sharp and tissue-penetrating, and is protected (e.g., shielded or covered) relative to a central loading region that extends longitudinally through the jaw member (e.g., lower jaw member) when the tissue penetrator is retracted into the device prior to being extended. Thus, the sharp distal tip of the needle may be located slightly displaced relative to the middle of the width of the tissue penetrator at the distal end of the tissue penetrator (e.g., offset by between about 1% and about 40% of the midline of the midline of the width of the tissue penetrator, e.g., between about 1%, 2%, 3%, 4%, 5%, 6%, 7%, 8%, 9%, 10%, 12%, 15%, 20%, or 24% and about 25%, 30%, 35%, 40% of the midline of the width of the tissue penetrator).

Any of the apparatuses described herein may include a tissue penetrator that include a distal sharp tissue penetrator region that includes a side opening into a suture retaining region that is located just proximal to the distal tip; the proximal portion of the side opening may be curved towards the proximal end of the tissue penetrator, so that the width of the side opening gradually increases to the overall width of the tissue penetrator as the outer edge of the side opening extends proximally. This configuration may prevent tissue from snagging or catching on this lower (proximal) edge region of the side opening when extending the tissue penetrator distally through the tissue.

Also described herein are devices that include a suture guide feature, also referred to as a centering feature or centering channel, on the jaw (e.g., a first or lower jaw) in which the tissue penetrator and preloaded suture are held; the centering feature may provide centering forces on the preloaded second bight of suture so that it can be reliable pulled into the hook (suture engagement region) of the tissue penetrator (needle). The suture guide feature may be referred to as a centering channel, as it may form a channel through a structure (such as the jaw housing in which the tissue penetrator slides) that one leg of the second preloaded bight of suture is threaded through. The centering feature (centering channel) may include one or more openings, including in some variations two openings, through which the suture leg is threaded. When the centering channel includes two opening through the jaw housing or a structure attached to the jaw housing, a recessed connecting channel may be formed between the two openings. The recessed connecting channel portion of the centering channel may reduce friction due to contact between the suture and the tissue being held in the jaw. For example, described herein are replaceable jaw cartridges for use with a suture passer device, the jaw cartridge comprising: a jaw housing; a tissue penetrator configured to slide distally and proximally within the jaw housing; a suture within the jaw housing, the suture comprising a first bight region loaded in a suture engagement region at a distal end region of the tissue penetrator, and a second bight region loaded in a suture holding region within the jaw housing; a centering channel through which the second bight region is threaded, wherein the centering channel is positioned opposite from (e.g., radially inward of) and proximal to the suture holding region; and a releasable hold that moves with the tissue penetrator and releasably secures a first end region of the suture against the tissue penetrator; wherein the releasable hold is configured to hold a portion of the suture between the first end region and the second bight region so that the portion is in tension when the tissue penetrator is withdrawn proximally so that a centering force is applied to the second bight region to pull the second bight region from the suture holding region into the suture engagement region of the tissue penetrator.

Although this example above (and shown herein) is described as a replaceable cartridge including a jaw, the apparatus may be part of a suture passer that is not configured as a removable cartridge. Further, although the centering element (centering channel) show in the examples provided herein is formed through an upper surface of the jaw housing in which the needle slides, it may be formed of a separate structure that is coupled to the jaw housing, rather than part of the housing itself. For example, the centering channel may be a loop attached to the jaw housing (so that it does not move relative to the jaw housing, even when the tissue penetrator moves, or when the jaw as a whole moves relative to the device), such as a wire loop; the loop (channel) may be within the jaw housing.

As mentioned above, any of the apparatuses described herein may include some or all of the features described and illustrated.

BRIEF DESCRIPTION OF THE DRAWINGS

In FIG. 1C the cartridge is coupled to the suture passer assembly and the lower jaw is fully retracted (thus the cartridge is fully retracted). In FIG. 1D the same suture passer apparatus is shown with the lower jaw extended to form a distal-facing opening between the upper jaw and the lower jaw region of the cartridge.

FIG. 4A shows an enlarged isometric view of one example of a preloaded and automatically reloading cartridge.

In FIGS. 8A-8L, the tissue being repaired corresponds to knee meniscus tissue.

FIG. 9A illustrates passing of the first bight through the tissue, and FIG. 9B shows the resulting entangled or trapped configuration after passing the second bight through the tissue.

FIGS. 11A-11H illustrate the operation of the gate shown in FIG. 10 to prevent a first region of suture from reentering the jaw member when passing a second region of suture.

FIGS. 17A-17E illustrate one example of passing a first preloaded suture, automatically reloading a second end of the suture that is also preloaded and passing the second end.

FIG. 19A-19D illustrate variations of jaw members including centering channels configured to applying a centering force vector to guide the second bight from the lateral suture engagement region into tissue penetrator hook region.

FIGS. 20A and 20B illustrate problems that may occur when loading the second bight that is otherwise preloaded into the suture engagement region into the hook region of a tissue penetrator.

DETAILED DESCRIPTION

Figure 1A:
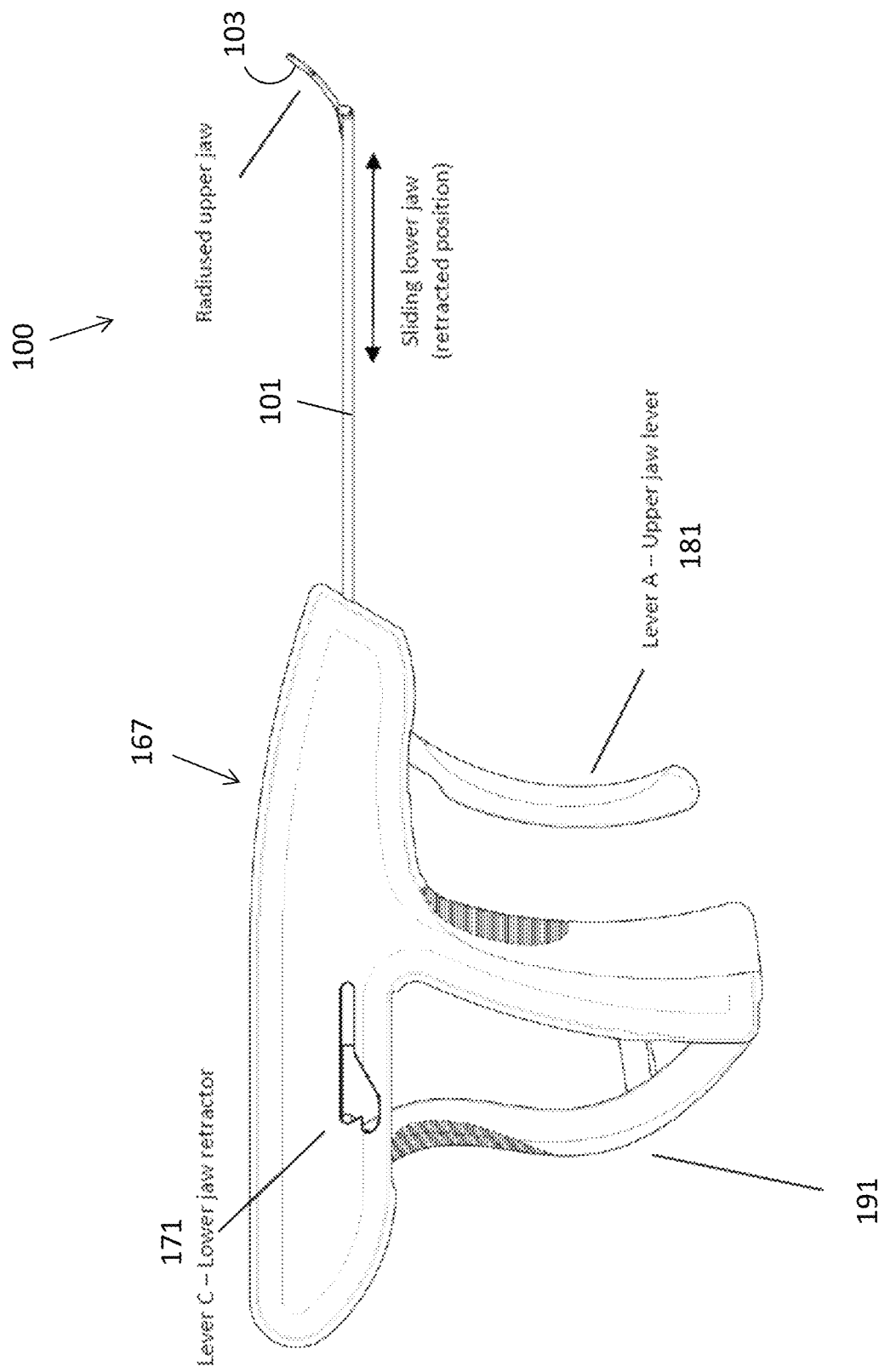
FIG. 1A shows one variation of a suture passer having a bent/bendable upper jaw and a lower jaw that slides axially (distal-to-proximal) in the long axis, with the lower jaw retracted.

In general, described herein are sutures passers configured to prevent a length of suture from re-entering a channel in the preloaded cartridge (e.g., in the jaw formed by the preloaded cartridge) and being entrapped by the tissue penetrator within the preloaded cartridge, methods of operating them, and methods of repairing tissue using them. These suture passers may be used arthroscopically, and may be used to pass one or more length of suture. These suture passers may include an elongate body and a first jaw member (e.g., first jaw) extending from the distal end of the elongate body, wherein the first jaw is bent or bendable relative to the distal to proximal axis of the elongate body. In some variations the first jaw is hinged near the distal end region of the elongate body. Some variations of the suture passers described herein include a second jaw member (e.g., second jaw) that is configured to slide axially (proximally and distally) relative to the elongate body and/or first jaw. The second jaw may be configured to slide axially sufficiently far proximally so that the distal tip of the second jaw is proximal to the distal end of the shaft (e.g., completely retracted). The first and second jaws may be configured to form a distal-facing opening into which tissue may be held. The suture passers described herein may also include a flexible, bendable, or pre-bent tissue penetrator for passing a suture through the tissue. The suture passer may also include a handle at the proximal end with one or more controls for actuating the first and/or second jaws and the tissue penetrator.

The suture passer described herein may have very narrow (thin) jaws. The tissue penetrator may exit the second jaw from the side of the second jaw and extend across a distal-facing opening to engage an opening in the opposite jaw (e.g., the first jaw), where a suture may be secured and/or released. For example, the suture passers described herein may have a second jaw having a maximum diameter (e.g., maximum height) along the length of the second jaw of less than about 0.11 inches, 0.10 inches, 0.09 inches, 0.08 inches, 0.07 inches, 0.06 inches, 0.05 inches, 0.04 inches, 0.03 inches, 0.2 inches, 0.01 inches, etc. The second jaw may be any appropriate width. For example, the width may be approximately 0.15 inches.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Preloaded Suture Passers

In general, any of the suture passer described herein may be adapted or configured prevent a length of suture from re-entering a channel in the preloaded cartridge (e.g., in the jaw formed by the preloaded cartridge) and being entrapped by the tissue penetrator within the preloaded cartridge. FIGS. 1A-1D, and 3A-7C illustrate apparatuses, including suture passers and cartridges for suture passers, that may be configured as described herein to prevent suture from being drawn back into the device where it could be entrapped and/or entangled with the tissue penetrator. For example, any of the suture passers described herein in FIGS. 1A-1D and 3A-7C may be configured as shown in any (or one or more of) FIG. 10-11H, 12A-12B, or 15. For example, any of the suture passers and cartridges for suture passers that are preloaded with one, or more preferably, more than one, length of suture that can be passed through tissue by the suture passer without requiring manual loading may include a gate (e.g., a deflectable gate) that prevents a length of suture from re-entering a distal channel in a lower jaw of the suture passer or preloaded suture passer cartridge and becoming entrapped by the tissue penetrator. A preloaded suture passers and cartridges for suture passers may include a suture holding/tensioning mechanism, which may be referred to as a releasable hold that is connected to, and may ride on, the tissue penetrator ("needle"); the releasable hold releasably secures an end of the suture and provides sufficient tension to load the suture onto the tissue penetrator during operation. A tissue penetrator may also and alternatively be referred to as a needle. A tissue penetrator/needle is generally configured to pierce tissue and pass (push and/or pull) suture. A tissue penetrator may be flat, cylindrical, etc.

and may have a square, oval, circular, or other shaped cross-section. The tissue penetrator is generally elongated and may include a notch, eye, hook, or the like for engaging a suture near or at its distal end.

In general, a suture passer device as described herein may be referred to as suture passer and/or a suturing device. Any of the features described herein may be included as part of a low-profile suture passer that includes a pair of jaws (e.g., distal-facing jaws) between which the needle may extend to pass suture. The low-profile suture passers may be configured to allow axial (sliding) movement of a jaw of the suture passer relative to the elongate body of the suture passer; the suture passer may also be configured so that the opposite jaw of the suture passer pivots or rotates relative to the elongate body of the suture passer, so that tissue can be clamped between the jaws before and/or during suturing. Low-profile suture passers having both sliding and rotating jaws may be referred to as dual deployment suture passers, and/or clamping/sliding suture passers.

Figure 1B:
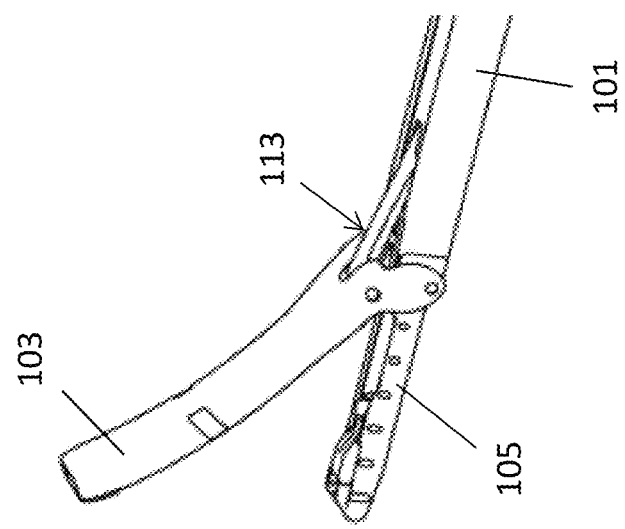
FIG. 1B shows a close-up of the distal end FIG. 1A with the lower jaw extended. The suture passer in FIGS. 1A and 1B may include an integrated preloaded and automatically reloading suture.

For example, a suture passer may generally include a first jaw member and second jaw member that both extend from the end of an elongate body region to form a distal-facing mouth into which tissue to be sutured fits. One or both jaws forming the mouth may be independently moved. FIGS. 1A and 1B illustrate one variation of a dual deployment suture passer 100. In this example, the device has a first (upper) jaw member 103 extending distally from the distal end of a more proximal elongate member 101. A second jaw member 105 (in FIG. 1B) extends distally beneath the first jaw member 103. This second jaw member may slide distally and proximally to retract and extend. A handle 107 is located at the proximal end of the device and includes multiple controls for independently controlling the movements of the first jaw 103, second jaw 105, and tissue penetrator (not shown in FIGS. 1A and 1B, though it may be housed with the tip retracted within either the first or second jaws.

One example of a suture passer that may be configured as a preloaded suture passer is shown in FIGS. 1A and 1B. In FIG. 1A, a first jaw member 103 is held at an angle relative to a long axis of the proximal elongate member 101. The first jaw 103 in this example is curved ("radiused") slightly and connected to the elongate body by a hinge region 113 about which the first jaw 103 may be angled relative to the elongate member 101. In some variations, this hinge region is a pinned hinge; non-pinned (e.g., living hinges) regions may be used. Any appropriate articulating region that allows the first jaw member to move at an angle relative to the proximal portion of the device (e.g., the elongate member) may be used. In some variations, this first jaw member 103 is referred to as an upper jaw member, but alternative variations (in which the first jaw member is a lower jaw member) are also possible.

A jaw lever 181 can be used to move (bend) or hold the first jaw member 103 angle. The first jaw member 103 may be actuated by any appropriate mechanism, including a tendon member (e.g., push rod, pull rod, or the like), and may be held (locked) at any angle (e.g., between 0° and 180° relative to a line extending from the distal end of the elongate body, between about 0° and 90°, between about 0° and 60°, etc.). In some variations the device has a neutral position during which no force is applied to the controller to move the first jaw member, so that the first jaw member is angled "open" (e.g., at 30°, 45°, 50°, 90° or at any angle between about 15° and about 90°) relative to the elongate body; actuating (e.g., pressing) the control on the handle results in the first jaw member moving towards the "closed" position (e.g., reducing the angle with respect to a line extending from the distal end of the elongate body). In some variations the jaw member is in the neutral position when angled with 0°/180° relative to the elongate body.

The first jaw member 103 shown in FIGS. 1A and 1B also includes a suture retainer region near the distal end. A suture retainer can hold a suture that has been passed into the suture retainer from the tissue penetrator. This suture retainer region may include a grasper, a pair of graspers, a deflectable member into which the suture may be pushed and held (e.g., handed off from the tissue penetrator), or the like. For example, the retainer may be a leaf spring element that is displaced by the tissue penetrator as it enters the jaw member in variation in which the tissue penetrator is housed in/behind the lower (sliding) jaw.

The second jaw 105 is shown in FIG. 1B as a lower jaw member. In this variation, the lower jaw 105 is configured to slide proximally towards and into the proximal elongate body 101 of the device (as shown in FIG. 1A). The second jaw 105 typically moves axially, in the direction of the proximal-distal axis of the suture passer. The second jaw member 105 may move axially completely past the distal end of the elongate body; alternatively, the second jaw member 105 may slide axially in the proximal direction only partially (e.g. to align with the hinge region of the first jaw member). The suture passer may be configured so that the second jaw 105 can retract completely into, and extend out of, the lower portion of the elongate body 101. A control (e.g., retractor lever) 171 on the handle 107 can be used to trigger retraction of the second jaw member 105 while another control (e.g., lower jaw/needle lever) 191 can be used to extend the second jaw 105. In FIGS. 1A and 1B, the lower jaw/needle lever is configured to both extend the lower jaw when squeezed once, and to extend and retract the tissue penetrator (needle) when squeezing the lever a second time; squeezing the second time extends the needle and releasing the lever retracts the needle.

A tissue penetrator (not visible in FIGS. 1A and 1B) may be housed within or behind the second jaw 105. Alternatively, the suture passer may be configured so that the tissue penetrator is housed within or behind the upper jaw and the suture retainer region is on the opposite (e.g., lower) jaw. The tissue penetrator may be configured as a needle, wire, knife, blade, or other element that is configured to extend from within either the first or second jaw members and across the opening between the jaw members to engage a suture and push the suture through the tissue from a first jaw (e.g., the lower jaw) where it can be held by the suture retainer region on the opposite jaw (e.g., the upper jaw). In general, the tissue penetrator may be configured to completely retract into the housing of the second jaw member 105. It may be extended across the opening between the jaws by actuating a member in the handle to push or otherwise drive (slide) it out of the jaw and deflect it across the opening, and though any tissue held between the jaws. In FIGS. 1A and 1B, the second jaw member 105 completely houses the tissue penetrator and includes a deflection region that drives the tissue penetrator up and out of the second jaw member by deflecting it across the opening between the two. The jaw/needle lever 191 can be used to extend the tissue penetrator (for example, a first squeeze can advance the second jaw member 105 and once the lower jaw is extended, an additional squeeze or squeezes can extend the needle.

A suture passer, such as the suture passer described in FIGS. 1A and 1B, can be configured to be preloaded with suture for multiple passes. This can be performed either with a replaceable cartridge or by configuring the lower jaw of the suture passer to include a suture having a first bight (e.g., bend, loop, etc.) region, a second bight region, a tissue penetrator holding the first length (bight) of suture, a suture holding region holding the second bight, and a releasable hold on the suture passer that drives the second bight region from the holding region to re-load the tissue penetrator after the first bight has been passed.

For example, a suture passer apparatus as described herein may be configured to operate with cartridge (e.g., a preloaded cartridge). In general, the preloaded cartridge may be part of a replaceable assembly that is preloaded with suture; the preloaded cartridge engages with a durable assembly including components of the suture passer that can be reused, while the cartridge includes "disposable" components (e.g., suture, tissue penetrator) that are consumable, and/or limited-use.

In general, a cartridge may include one of the jaw members of a suture passer, such as the lower jaw, the suture, and the tissue penetrator, as well as a releasable hold that re-loads the suture into the tissue penetrator after it has been passed. A cartridge may also include a housing that completely or partially covers the suture and tissue penetrator. The housing may also include a storage region (e.g., capsule) for holding the length(s) of suture, and any additional suture management components (e.g., funnels, channels, spools, etc.) for guiding the suture. As mentioned above, in some variations a removable, replaceable and/or releasable cartridge is not used, but the entire suture passer may be preloaded with suture and disposable after use.

In some variations of the cartridge described herein the cartridge is preloaded with suture and a tissue penetrator and engages with a durable suture passer body. The reusable or durable suture passer body may be referred to as a durable portion or durable assembly of a suture passer apparatus. In general, the durable portion may include an elongate body, a first jaw member (e.g., pivoting, bent, bendable, or fixed), and a handle including controls for controlling movement of the jaw(s) and tissue penetrator. The replaceable cartridge portion may be referred to as a cartridge assembly, and typically includes a housing attached to or forming all or part of a (e.g., second) jaw, a tissue penetrator (e.g., needle) and a suture. The suture is typically both preloaded into the tissue penetrator and may also be "primed" for loading a second length into the tissue penetrator after the first length has been passed from the tissue penetrator.

For example, the second jaw member 105 can be part of a suture cartridge that is configured to hold at least two preloaded loops of suture to be passed. Further, as described more detail below, the suture cartridge can be configured to attach to and detach from the rest of the apparatus (e.g., to the durable assembly portion of the suture passer).

Figure 1C:
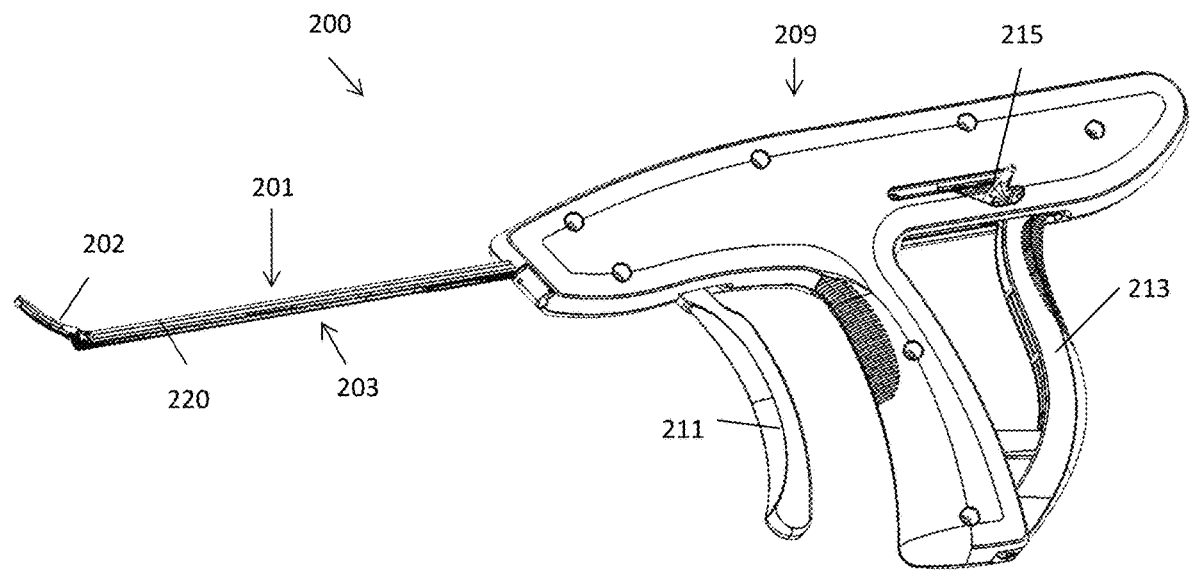
FIGS. 1C and 1D show side perspective views of an example of a suture passer apparatus formed of a reusable/durable suture passer assembly including the upper (pivoting) jaw, elongate body and handle with controls, to which a preloaded and automatically reloading cartridge forming the lower jaw assembly has been attached.
Figure 1D:
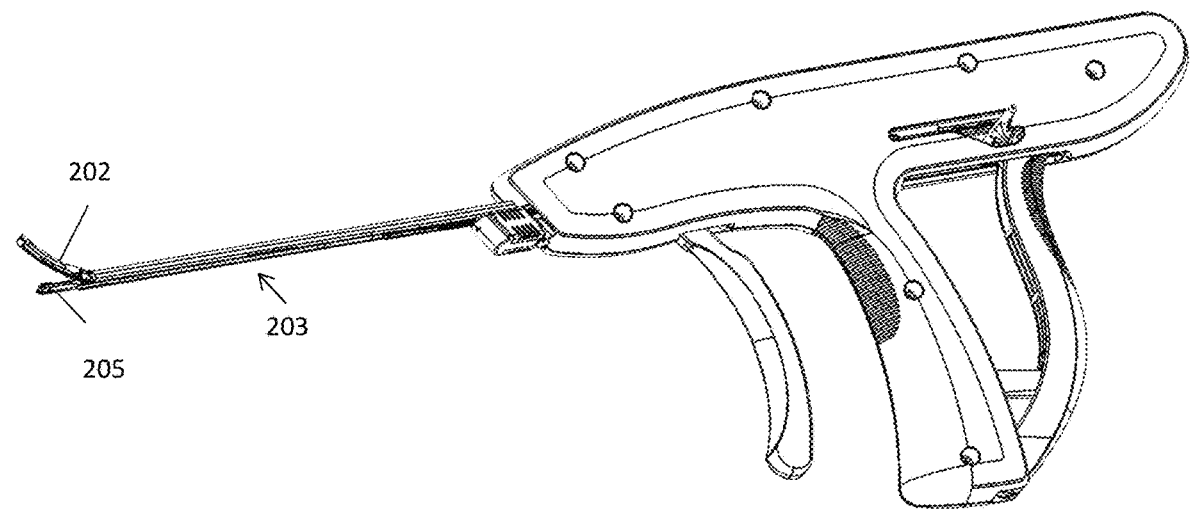
Figure 2:
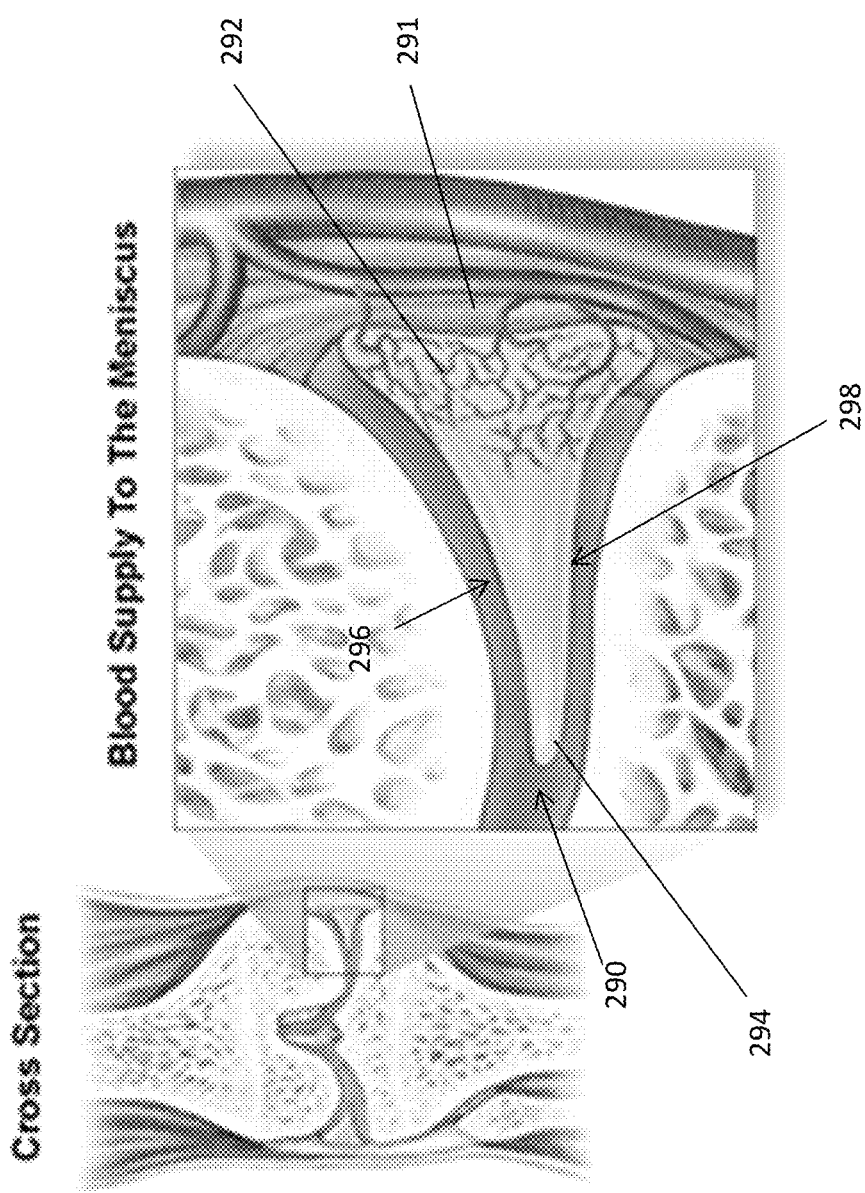
FIG. 2 illustrates the anatomy of the meniscus, including the capsule and associated vascular tissue.

FIGS. 1C and 1D illustrate a suture passer 200 that is configured as a clamping/sliding suture passer, having both a sliding lower jaw 205 and bending/pivoting upper jaw 207, where the lower jaw is formed as part of a preloaded cartridge 203. In FIG. 1C the durable assembly 201 and the replaceable cartridge assembly 203 are combined to form the suture passer 200. When combined, the operation of the device may be controlled as described above. The handle 209 includes a first control (upper jaw or bending jaw control) 211 for controlling the angle of the upper jaw 202, a second control (e.g., jaw extending/needle extending control) 213 for controlling extension of the lower jaw and extension/retraction of the tissue penetrator, and a lower jaw release 215 control that retracts the lower jaw after it has been extended. In FIGS. 1C and 1D, the lower jaw is part of the cartridge assembly and in FIG. 1C is shown retracted proximally relative to the elongate shaft 220 of the apparatus. In FIG. 1D, the lower jaw 205 is shown extended distally relative to the long axis (e.g., the distal-to-proximal axis of the elongate body 220); this may be achieved by actuating (e.g., squeezing) the second control to extend the entire cartridge 203 and therefore the lower jaw region 205 distally. When extended distally the upper 202 and lower 205 jaws form a distal-facing opening across which a tissue penetrator (not shown) may be extended from the cartridge to pass the preloaded suture.

Figure 3A:
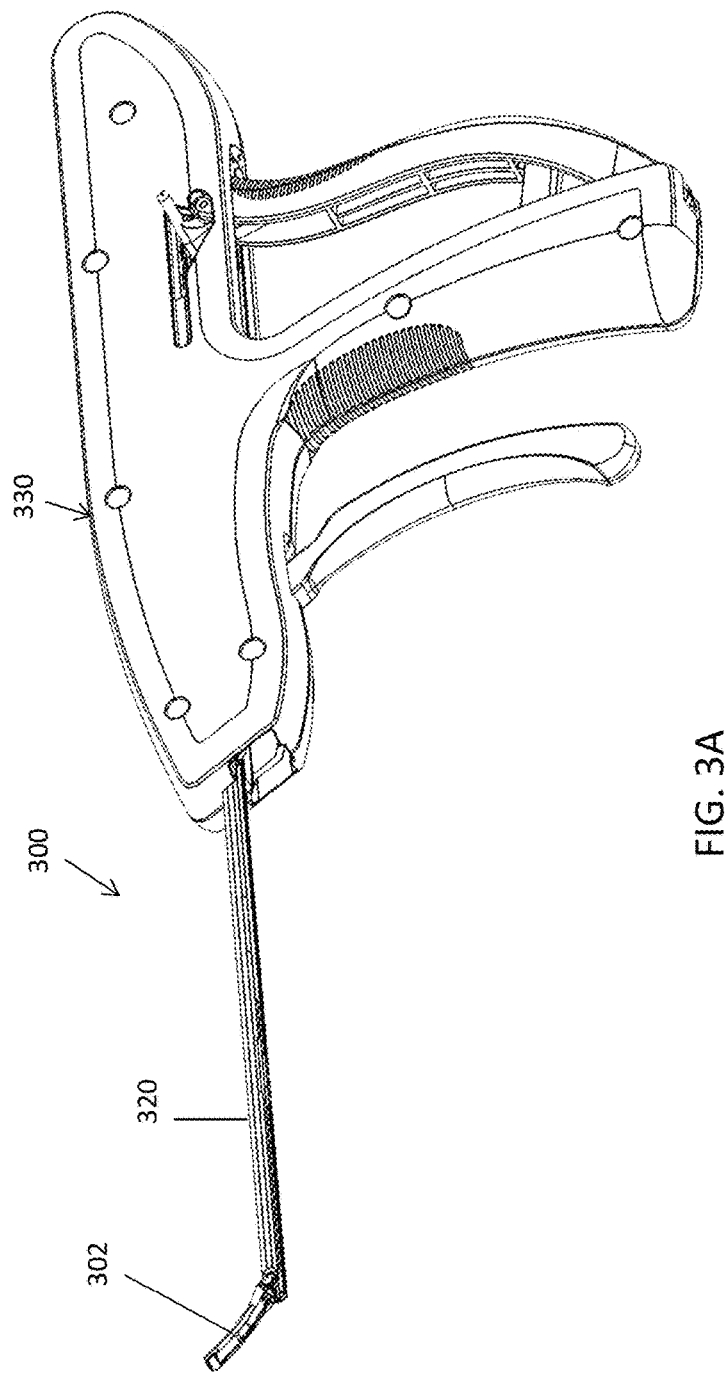
FIG. 3A shows an example of a suture passer assembly (which may be configured as a reusable/durable suture passer assembly) such as the one shown in FIGS. 1C and 1D without a cartridge attached.
Figure 3B:
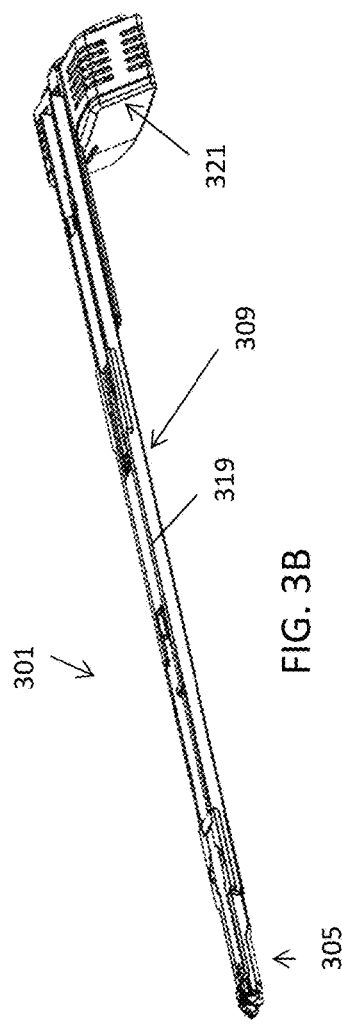
FIG. 3B shows a cartridge (including a lower jaw housing, tissue penetrator, and suture) that is configured to be preloaded and automatically reloading the suture.

FIG. 3A illustrates one embodiment of a durable assembly 300 of a suture passer, without the attached cartridge shown in FIG. 3B. In FIG. 3A, the durable assembly includes the upper jaw 302, an elongate body 320, and a handle 330 with controls. The durable assembly is adapted for releasably coupling with a preloaded cartridge, such as the one shown in FIG. 3B. For example the durable assembly may include one or more keyed regions to which a cartridge may be coupled. The cartridge may therefore include complementary regions for engaging the durable assembly. An example of how a cartridge may be engaged with a durable assembly to form the suture passer is described in greater detail below.

Figure 3C:
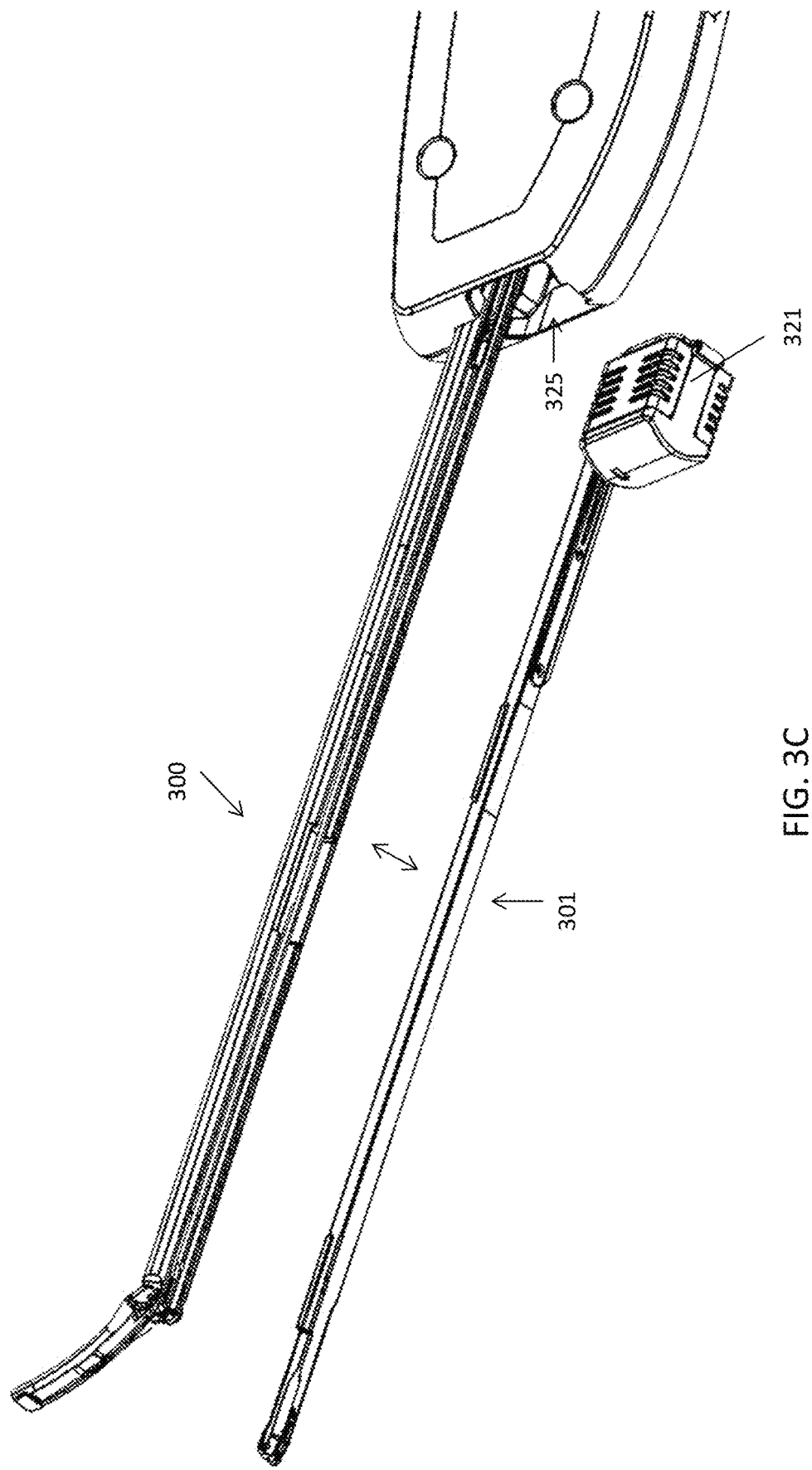
FIG. 3C shows the suture passer assembly of FIG. 3A being coupled to the cartridge of FIG. 3B.

FIGS. 3B and 3C show perspective views of a cartridge 301 that includes a jaw (lower jaw) region 305 and a housing 309 that at least partially encloses a suture, tissue penetrator, suture holding region and releasable hold on the tissue penetrator. In this example, the housing includes a lower jaw region 305, an elongate region 319, and a suture capsule 321. The suture capsule stores at least a portion of the suture to be passed. In some variations a single long (e.g., 2 inches, 3 inches, 4 inches, 5 inches, 6 inches, 7 inches, 8 inches, 9 inches, 10 inches, 12 inches, 13 inches, 14 inches, etc.) length of suture may be used to form both a first bight region and a second bight region that are separately passed by the device and loaded automatically and/or preloaded into the tissue penetrator by the cartridge. The first bight may be at one end region and the second bight may be at the other end region. As indicated in FIG. 3C, the cartridge 301 may be connected and disconnected from the durable assembly 300. Thus, in operation a new preloaded cartridge 301 may be connected to a durable assembly 300, the device may be used (e.g., to pass two lengths/bights of suture) and the assembly may be removed and a fresh (preloaded) cartridge attached. The used cartridge may be refurbished (e.g., by replacing the suture and/or the tissue penetrator), reloaded, recycled, or otherwise disposed of. A portion of the cartridge may be inserted into the durable assembly. For example, in FIG. 3C, the suture capsule region 321 may be retracted into a portion 325 of the handle when the lower jaw is retracted proximally.

The elongate body 101 shown in FIGS. 1A-3C is illustrated as a relatively straight, flattened and cylindrical structure, though other shapes may be used. For example, the elongate body may be curved, bent, or angled. In some variations the elongate body is configured to be bent, curved or angled dynamically (e.g., by changing the bend or curve).

The elongate body of the suture passer (which may include both the elongate body region of the durable component and/or the elongate body portion of the cartridge that can mate with the durable component) may be any appropriate length. For example, the elongate body may be between about 6 and about 24 inches long, e.g., 6 inches long, 8 inches long, 10 inches long, 12 inches long, etc. The suture passers described herein may be used for arthroscopic surgeries and therefore may be dimensioned for use as such. Thus the diameter of the device may be configured to be small enough for insertion into a cannula, tube or the like for insertion into the body.

In general, a suture can be preloaded in a suture cartridge 1000 for use in automatically and sequentially passing two or more lengths of suture with a suture passer, such as the suture passers of FIG. 1A-1B or 1C-1D. FIG. 4A illustrate a variation of a suture cartridge 400 configured to be used as part of a suture passer that can hold and pass two lengths of suture. As mentioned, the suture cartridge 400 can be configured to attach and detach from a durable assembly of a suture passer. The suture cartridge 400 in this example includes a lower jaw 405 (i.e., similar to the lower jaw 105 of FIGS. 1A and 1B) as well as a suture storage capsule 421.

The lower jaw 405 can include a housing 409 that encloses a tissue penetrator 403 and first and second bights. A track can run within the housing 409 of the cartridge along which the tissue penetrator 403 can slide when moving within and/or extending in and out of the cartridge. The track can be sized such that the tissue penetrator 403 fits within the track but prevents the suture from engaging in the track. A suture holding region (not visible in FIG. 4A) may be formed between the housing (e.g., the track) and the tissue penetrator, for holding the second bight region of suture. A top cover 407 can be placed over a distal portion of the housing which may help retain the ends of the suture(s), including the bight regions, in a correct position within the cartridge.

Figure 4B:
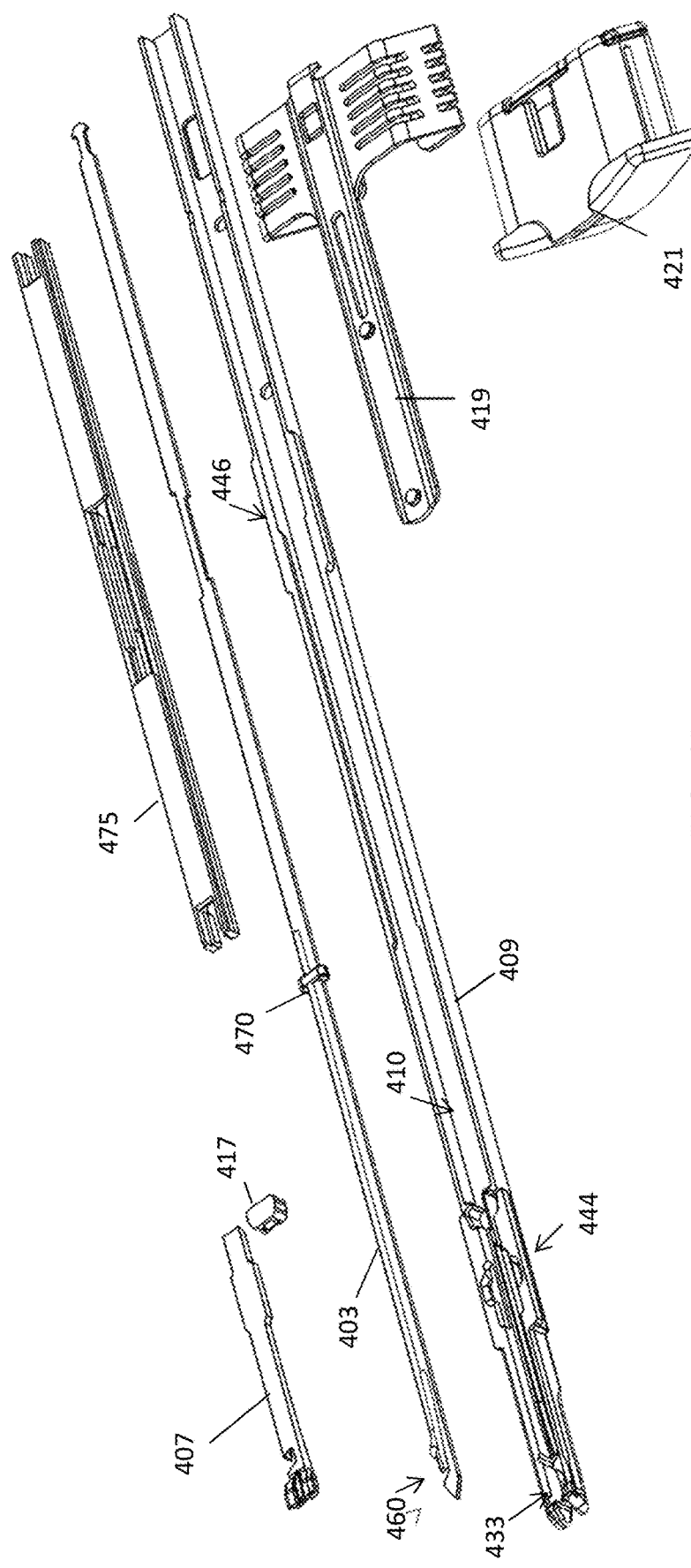
FIG. 4B shows an exploded view of the cartridge of FIG. 4A.

FIG. 4B shows an exploded view of the cartridge shown in FIG. 4A. The cartridge may be assembled to include the housing 409, which may be referred to as a jaw housing or lower jaw housing. A suture holding region (suture capsule 421) may be integral with the jaw housing or separate from it, but is attached so that the suture can continue from the jaw housing to the suture holding region. If the holding region 421 is separate from the jaw housing 409, a connection tab 419 may be attached over the housing at the proximal end of the cartridge and may secure the holding region to the rest of the housing. The inner region 410 of the housing may be configured to hold the suture and tissue penetrator, and also to allow the tissue penetrator to slide within and out of the housing. For example, the inner region 410 of the housing may include a distal deflector (ramp) region 433. The housing 409 may also include the engagement regions such as extending structures (posts, flanges, etc.) that may be keyed to complementary engagement regions on a durable assembly to secure the durable assembly and the cartridge together. In FIG. 4B, two sets of flanges or keyed regions 444, 446 are shown.

A suture 460 and tissue penetrator 403 may also fit within the cartridges lower jaw housing. In FIG. 4B, the suture is shown coupled to the tissue penetrator so that a first bight is preloaded into a notch region forming a suture engagement region of the tissue penetrator. A second bight at the second end of the same suture is held to the side of the tissue penetrator and the end region of the suture distal from the second bight region is coupled to the tissue penetrator by a releasable hold 470 configured as a clasp in this example. The tissue penetrator may be coupled to a sled (e.g., needle sled) 475 that is also held within the jaw housing. As described in detail below in some variations a separate releasable hold is not required; for example the sled may be configured to include the releasable hold (see, e.g., FIG. 11A). A needle sled may act to couple the tissue penetrator to a push/pull rod in the durable component for actuating the needle. The lower jaw housing may also include a cover (e.g., top cover) 407 over all or a portion of the jaw housing, such as the distal end region. Additional suture management regions may also be included, such as a funnel 417 that can be used to guide the suture within the housing, and help prevent it from tangling within the housing or getting pinched between a wall of the housing and the needle.

Figure 5A:
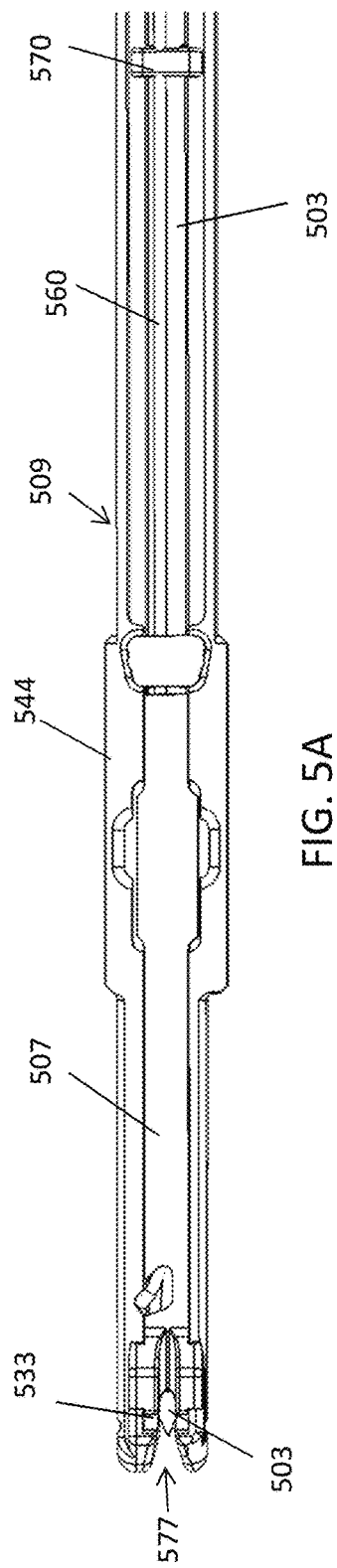
FIGS. 5A-5C show top, side perspective and side views, respectively, of the distal end of a preloaded and automatically reloadable cartridge such as the one shown in FIG. 4A.
Figure 5B:
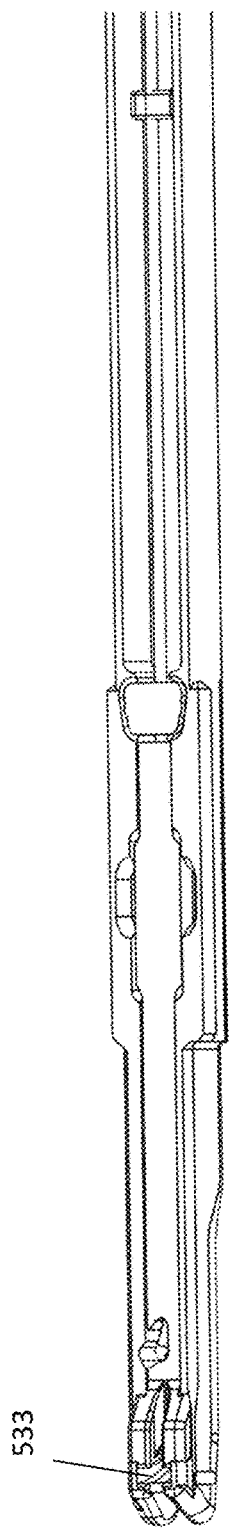
Figure 5C:
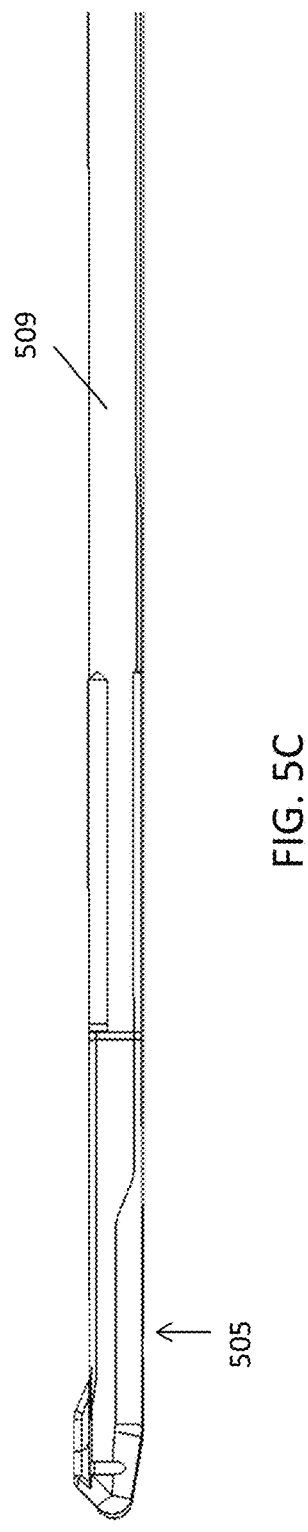

FIGS. 5A-5C show additional detail of a variation of an assembled cartridge such as the one shown in FIG. 4A. In FIG. 5A, a top view of the distal end region of the assembly shows a housing 509, top cover 507, and tissue penetrator 503. A releasable hold 570 is coupled to the tissue penetrator, holding a distal end region of a suture 560. The housing includes a flanged region 544 to engage with a durable assembly of a suture passer, and a ramped deflection region 533 to direct the tissue penetrator laterally from the cartridge.

Figure 6:
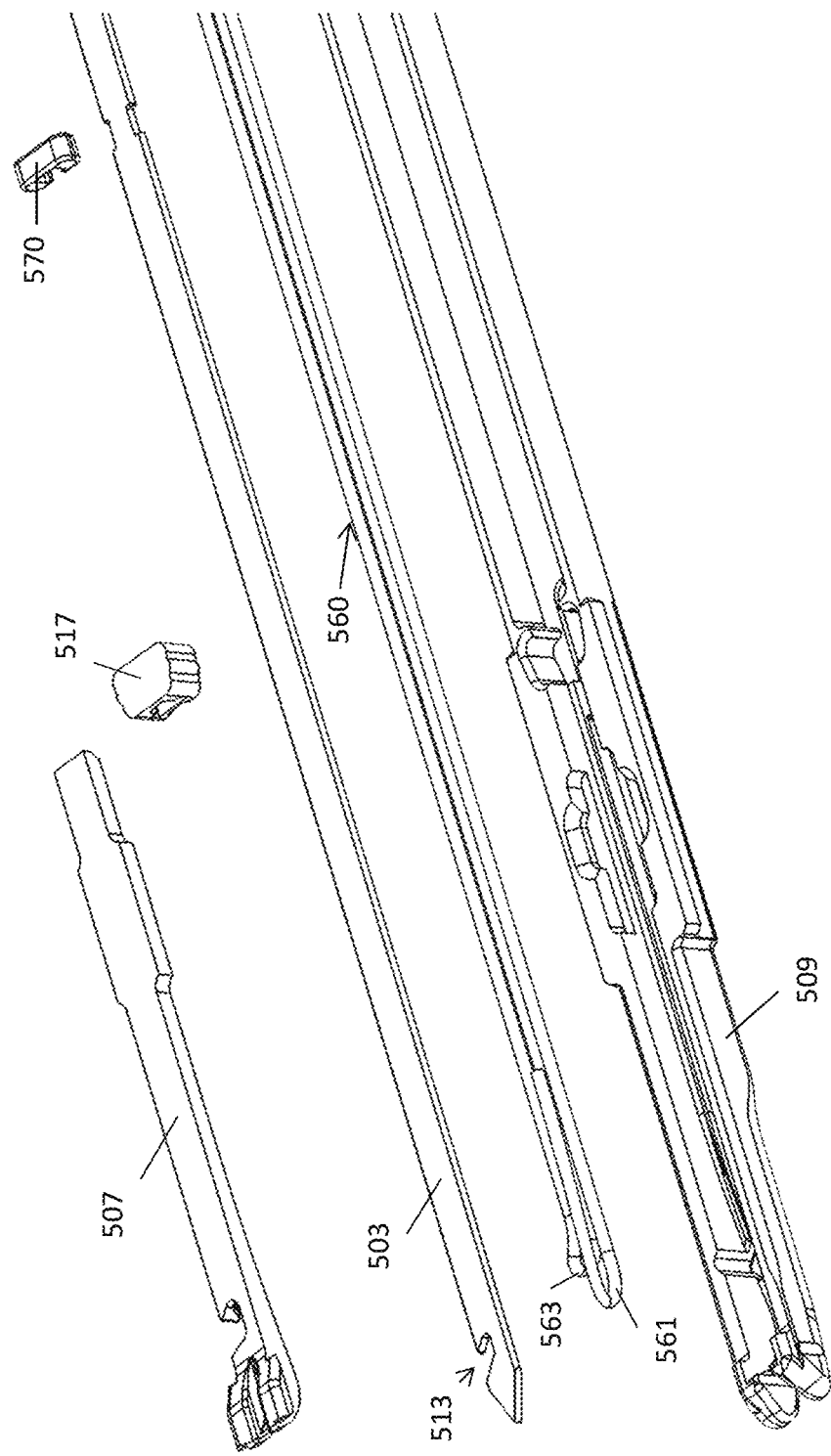
FIG. 6 is an exploded view of a distal end region of one variation of a preloaded and automatically reloadable cartridge.

FIG. 5B shows a side perspective view and FIG. 5C shows a side view. As can be seen in FIG. 5B, the cartridge, and particularly the lower jaw region 505 is thin and relatively flat. FIG. 6 is an enlarged and exploded view of the distal end of the cartridge, showing the housing 509, a suture 560 (including a first bight region 561 and second bight region 563), tissue penetrator 503 (including suture engagement region 513), a releasable hold (clasp 570), top cover 507, and suture management element (funnel 517).

Figure 7A:
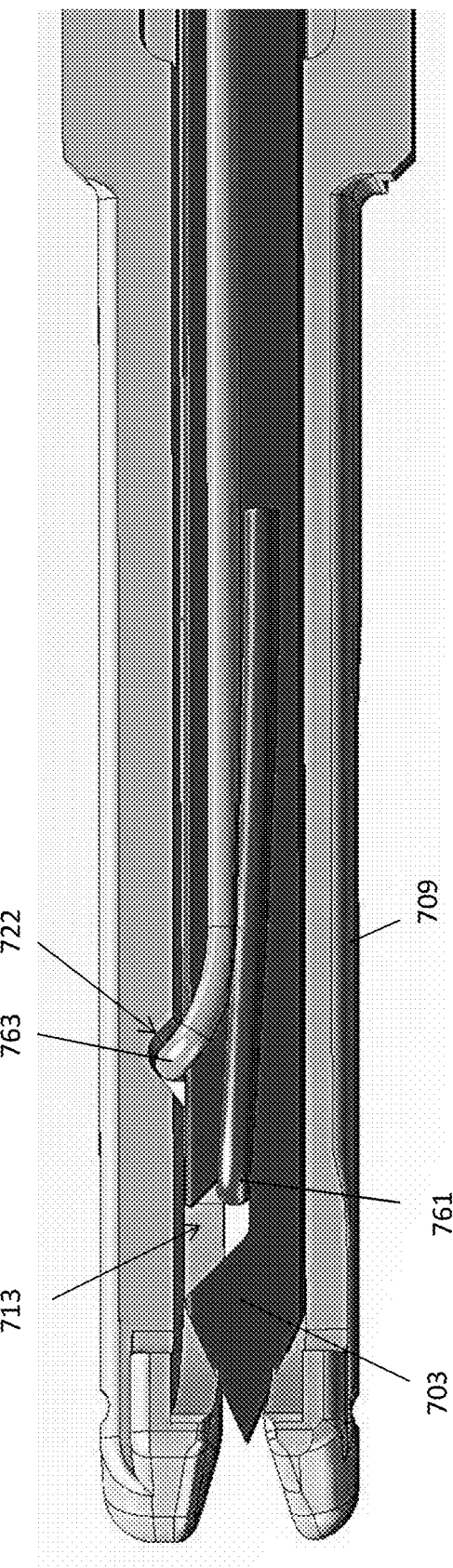
FIG. 7A shows an enlarged view of the distal end region of a preloaded and automatically reloadable cartridge such as the one shown in FIGS. 5A-5C.
Figure 7B:
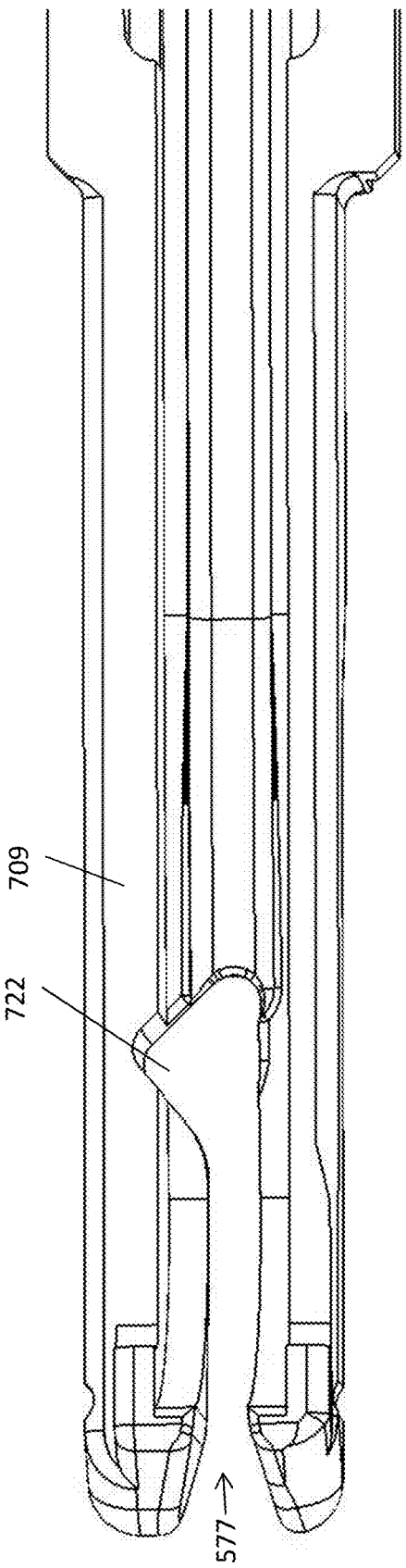
FIG. 7B shows an enlarged view of the cartridge housing for the preloaded and automatically reloadable cartridge of FIG. 7A.

Similarly, FIGS. 7A and 7B show a top view of the distal end region of a cartridge. In FIG. 7A a top cover has been made removed to show how the bights and end regions of the suture engage with the tissue penetrator within the cartridge. As shown in FIG. 7A, the first bight 761 of suture is held in the suture engagement region 713 of the tissue penetrator. A tissue penetrator generally retains a suture so that the suture can be pushed (or, in some variations pulled, or pushed and pulled) through the tissue by the tissue penetrator until it is held by a suture retainer on the opposite jaw. For example, in FIG. 7A, the tissue penetrator includes a notched region forming the suture engagement region 713; the notch is oriented at an angle relative to the length of the tissue penetrator, directed proximally, so that the suture is retained within the tissue penetrator as it is advanced distally. Other suture engagement regions may be used, including distal-facing suture engagement regions, or the like.

In FIG. 7A, a single suture forms the first and second bight regions; the portion of the suture between the first bight 761 and the second bight 763 runs behind the tissue penetrator (not visible in FIG. 7A), between the tissue penetrator and the jaw housing 709. The second bight region 763 on the opposite end of the suture is held in a suture holding region 722 that is off of the tissue penetrator, while the distal end region of the suture just distal to the second bight region 763 is secured to the tissue penetrator by the releasable hold (not visible in FIG. 7A, but see, e.g., FIG. 5A). The suture holding region 722 in FIGS. 7A and 7B is a notched region formed within the jaw housing laterally positioned relative to the tissue penetrator, and on the same side of the tissue penetrator as the opening into the suture engagement region 713 of the tissue penetrator 703. In operation, the suture holding region holds the second bight until the suture engagement region of the tissue penetrator is empty (e.g., of a bight of suture).

Figure 7C:
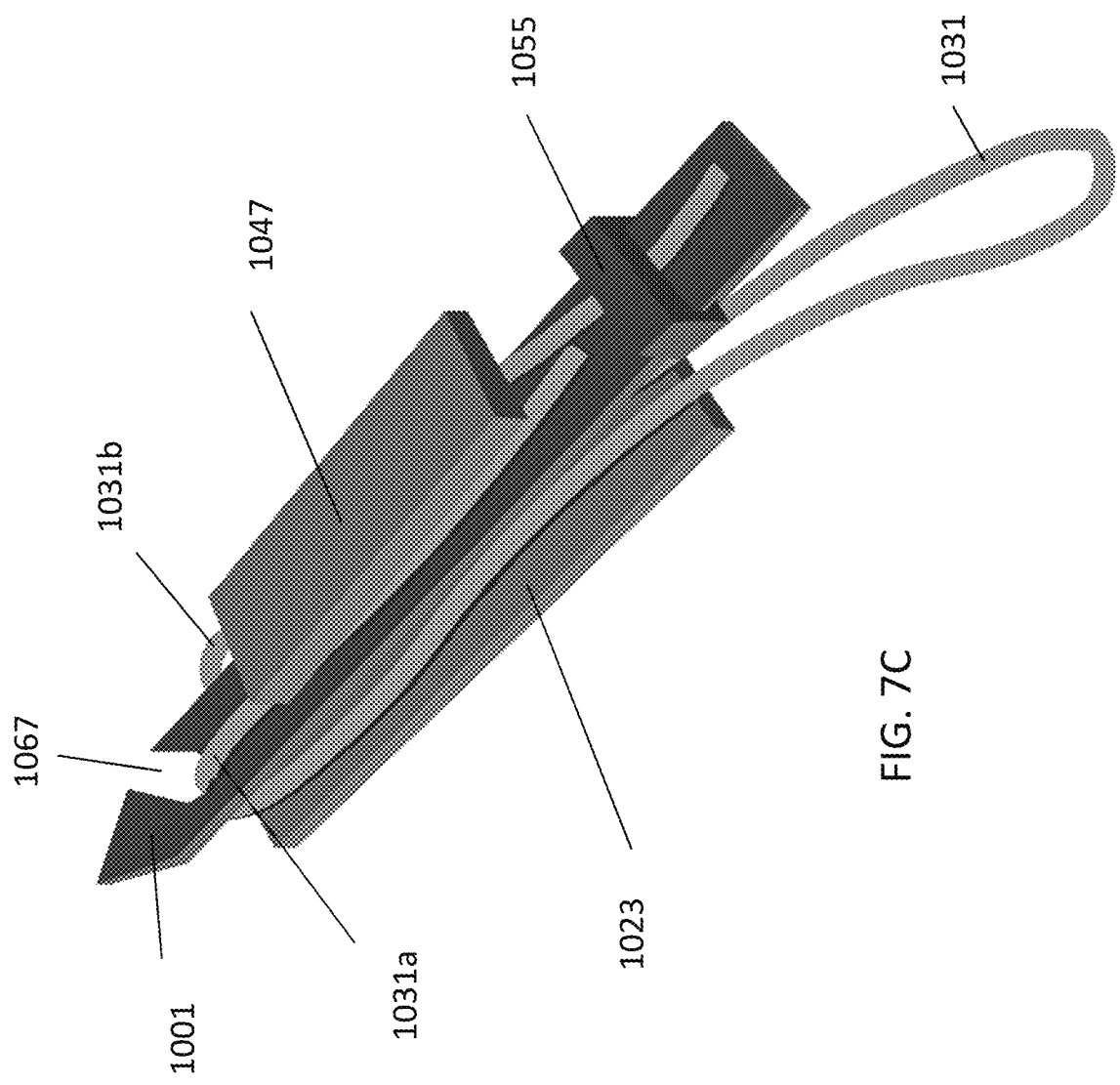
FIG. 7C is a partial perspective view, with some of the components removed or made partially transparent, showing the relationship between the tissue penetrator, suture and releasable hold, lower jaw housing, and top of one variation of a preloaded and automatically reloadable cartridge such as the one shown in FIGS. 7A-7B.

As used herein, a bight or bight region of suture refers to a length of suture. The length of suture forming the bight may be bent or looped; for example, the bight region may be bent so that the suture bends 180 degrees, as illustrated in FIG. 7A and FIG. 7C, discussed below. In some variations the bend forming the bight may prevent the suture from sliding or pulling distally or proximally.

Figure 9B:
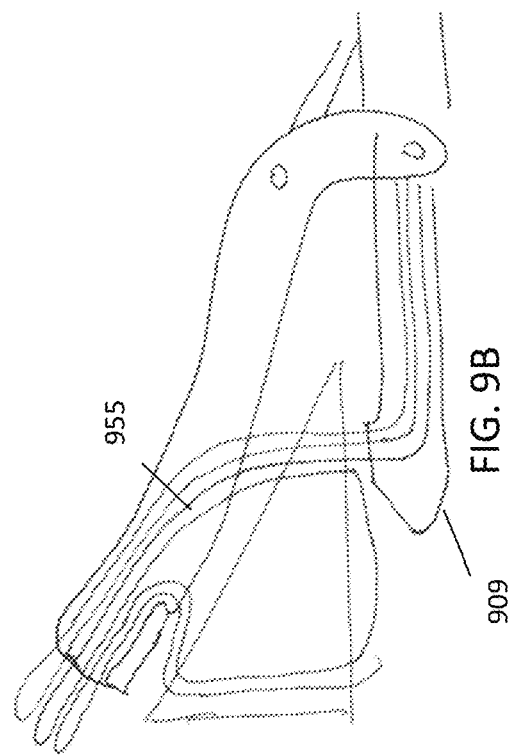
FIGS. 9A and 9B illustrate a failure mode of a suture passer in which a portion of a first region of suture (e.g., first bight or loop) is undesirably recaptured by the device when a second region (e.g., second bight or loop) is passed.
Figure 9A:
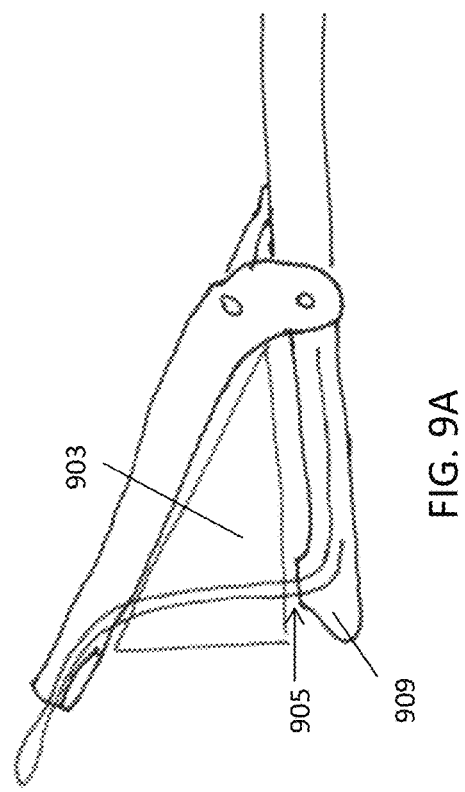
Figure 9C:
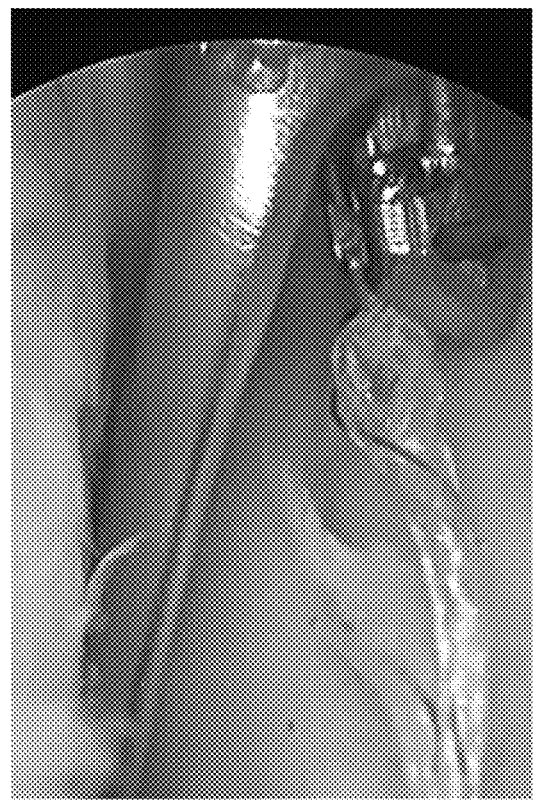
FIG. 9C is a picture illustrating a clinical example of this entanglement/entrapment of a portion of the first bight when passing the second bight using a preloaded suture such as those illustrated above.

As mentioned above, any of the suture passer apparatuses described herein may include a gate to prevent entanglement and/or entrapment of a suture. FIGS. 9A-9C illustrate the problem of entrapment or entanglement using a suture passer as shown above, similar to the one shown in FIGS. 3A-4C. When passing a suture using a preloaded suture passer as shown in FIGS. 3A-4C, the tissue penetrator may initially push a first (preloaded) bight of suture through a tissue held between the first and second jaws 903, as shown in FIG. 9A. Thereafter, the first bight is held in the tissue and the suture passer may be repositioned in a second location to pass the second bight of tissue and form the completed next bight. In variations in which the distal end region of the lower jaw 909 includes a channel (see, e.g., FIG. 5A, opening 577 into the distal channel), once the length of suture has been passed and has left the lower jaw member into which it was preloaded, it is possible for the length of suture to re-enter this channel in the lower jaw and get entangled in the tissue penetrator and/or the second bight of the suture, such that once the tissue penetrator is again passed through the tissue, it will extend this entangled region as well as the second bight through the tissue, as shown in FIG. 9B. In FIG. 9B, the entangled first region 955 is held within the capture region of the upper jaw, potentially preventing the suture passer from correctly withdrawing from the tissue, damaging the tissue, and compromising the procedure. FIG. 9C shows an actual figure from which this failure mode was identified in a cadaver knee procedure.

Figure 10:
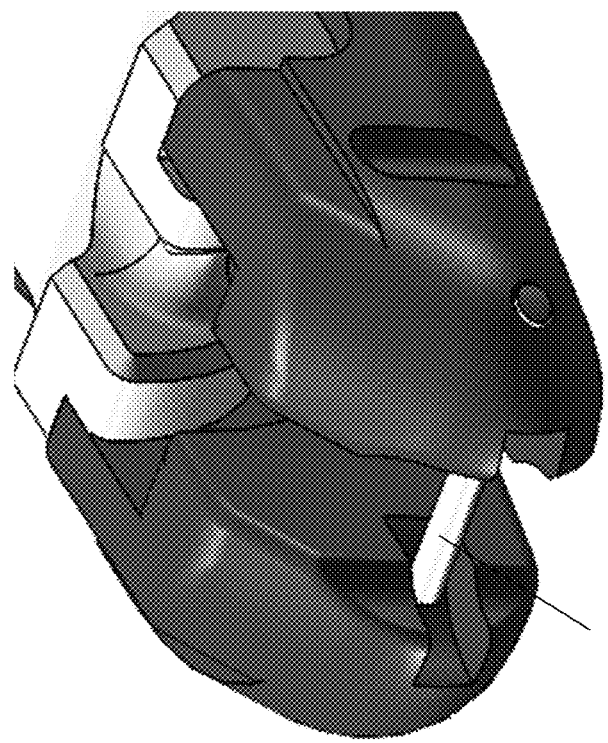
FIG. 10 illustrates a first embodiment of a preloaded suture passer having a gate (e.g., barrier, shown in this example as a turnstile-type gate or barrier) to prevent a region of suture, e.g., from the first bight, from inadvertently falling back into the channel or opening in the lower jaw member housing the suture passer/needle, thereby preventing entanglement of the suture with the second bight/loop being passed by the preloaded suture passer device.

One technique for addressing this failure mode is illustrated in FIGS. 10 and 11A-11H. As shown in FIG. 10, in any of the variation of suture passers shown herein, the distal end may include a deformable gate 1010 that is configured to prevent a loop of suture from passing through the metal gate and into the channel 1013 into the lower jaw, which s continuous with the path taken by the tissue penetrator within the lower jaw. In FIG. 10, the gate member is a pin that is attached at one end, but otherwise is free to move into a distal open position, but is prevented from opening proximally and allowing suture to enter the channel. In alternative variations, the gate pin shown in FIGS. 10 and 11A-11H includes is flexible and closes as shown in FIG. 10, and dynamically illustrated in FIGS. 11A-11H, described in greater detail below.

Figure 11C:
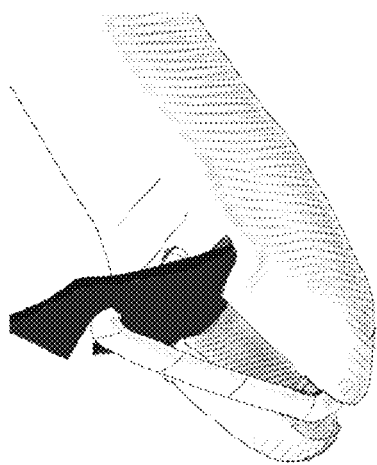
Figure 11B:
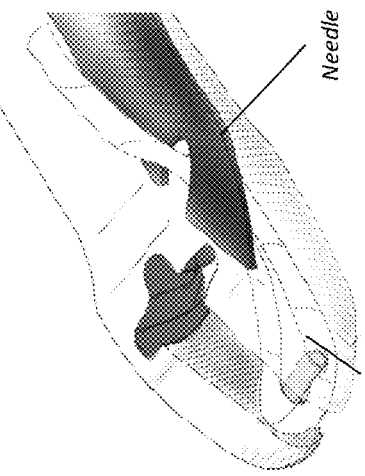
Figure 11A:
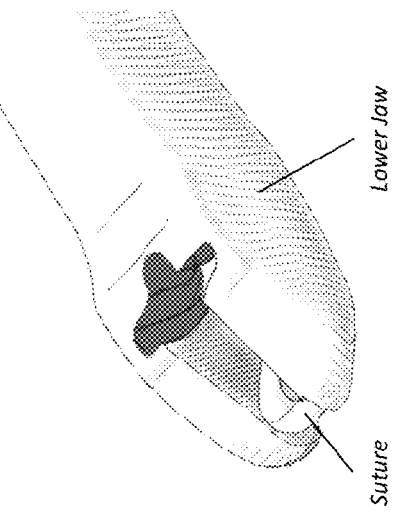

For example, in FIG. 11A, the distal end region of a lower jaw member shows the gate pin 1010 in a ready position, closed, but with a bight of the first preloaded suture looped over the gate pin. The partially transparent view shown in FIG. 11B illustrates the preloaded first length of suture loaded into the cut-out region in the tissue penetrator, and FIG. 11C illustrates how the tissue penetrator continues to extend through the tissue and pull or push the first length of suture along with it, and away from the gate pin. In FIG. 11D, the first bight been fully passed into the tissue and the needle (tissue penetrator) withdrawn. As shown in FIGS. 11E-11G, thereafter the region of the suture 1105 may be pulled away from the suture passer (lower jaw) and, the gate pin 1103. This is illustrated in FIG. 11G, showing the gate pin 1105 bending distally away to allow the suture length to be removed from within the channel 1107, after opening the gate 1103. As shown in FIG. 11H, once the suture length (connected to the first region of suture passed through the tissue) has been pulled out of the channel 1107, the gate 1105 prevents any suture from re-entering the channel 1107, where it may become entrapped by the tissue penetrator.

In FIG. 11A, one end of the suture is routed around the gate pin, which can swing out but not back in. As shown in FIG. 11B, the suture is still loaded around the needle but the additional routing around the gate pin places the suture outside the jaw upon exit. After passing the suture as normal (FIGS. 11C and 11D), the device is retracted, and the first suture end is routed outside the pin is still on the outside but the second suture end is inside the device, as shown in FIG. 11E. After the end of the suture has paid out from the cartridge (as shown in FIG. 11F), the final bight of the suture gets caught on the gate pin, which can flex (FIG. 11G) and allow the release of the final bight, thereby freeing the suture from the cartridge. Thereafter, the gate pin springs back towards its original position, as shown in FIG. 11H.

Figure 12B:
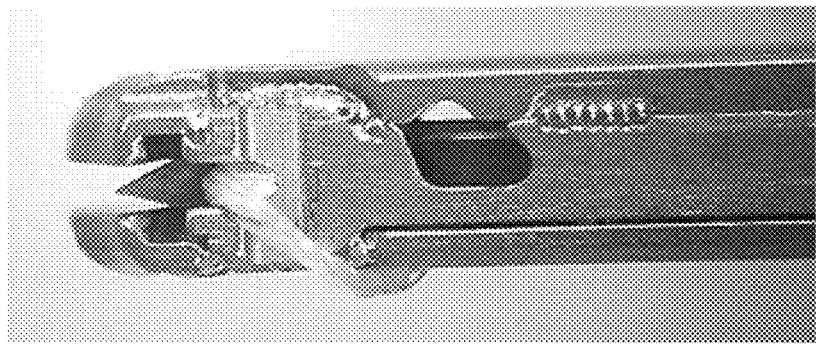
FIG. 12B illustrates the back of the preloaded jaw member shown in FIG. 12A.
Figure 12A:
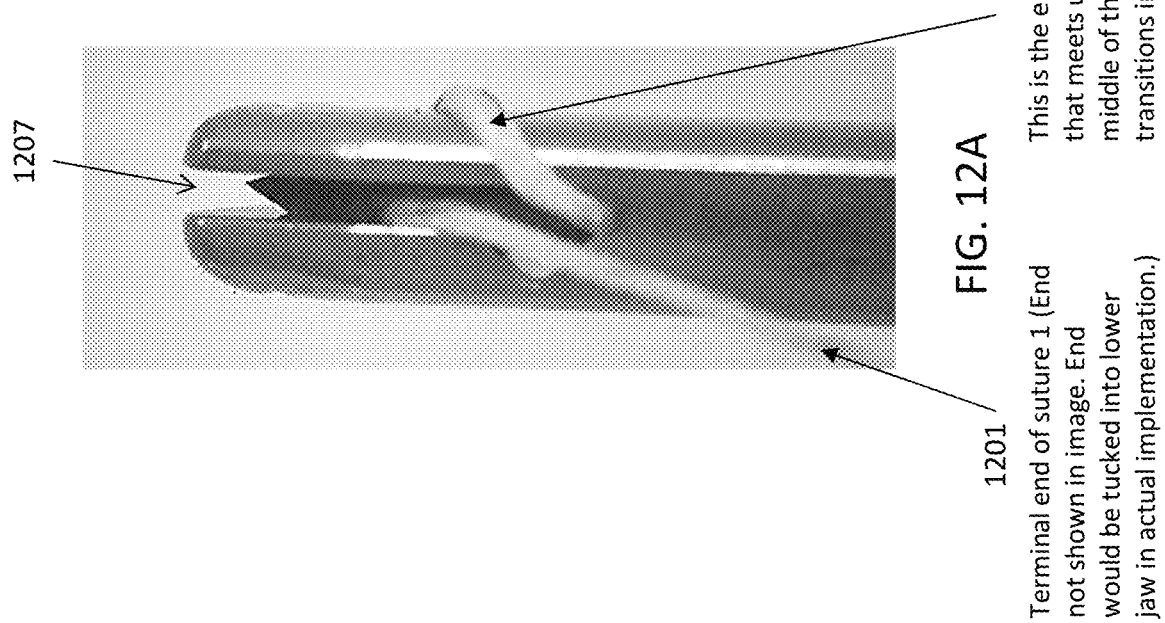
FIG. 12A illustrates another configuration of a preloaded suture passer (e.g., preloaded lower jaw member of the suture passer) configured to prevent entanglement/entrapment of another (e.g., first bight) region of a suture when passing a second region (e.g., second bight). In this example, the preloaded jaw is configured so that the first region of suture (the region between the first bight/loop preloaded and the second bight/loop preloaded is wound around the outside (or within a channel in/on) the lower jaw member.

FIGS. 12A and 12B illustrate another variation of a suture passer and/or preloaded cartridge for a suture passer that is configured to prevent a length of suture (e.g., already passed suture) back into the channel in the jaw where it may be entrapped by the tissue penetrator. In this example, the terminal end of the first preloaded suture bight region 1201 is wrapped around the lower jaw member as shown in FIGS. 12A and 12B, preventing it from re-entering the opening at the distal end 1207. FIG. 12B shows the back of the lower jaw member, while FIG. 12A shows the front. The jaw may include an outer channel (not shown) for holding the wrapped suture.

In operation, the preloaded suture passers described herein may be used to suture any appropriate tissue, not limited to knee (e.g., meniscus, ACL, etc.), hip (e.g., hip labrum, etc.), shoulder (e.g., rotator cuff), etc. For example, FIGS. 8A-8L illustrate one method, including optional steps, of using a preloaded suture passer to repair tissue; in this example, the meniscus includes a tear 2609 which may be circumferentially stitched by placing a first end of the suture through the meniscus on one side of the tear, and placing the opposite end of the suture on the other side of the tear.

Figure 8A:
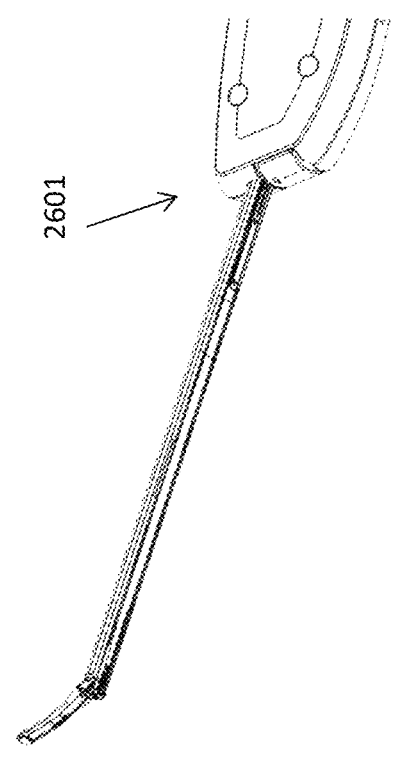
FIGS. 8A-8L illustrate one method (including optional steps) of operating a system such as the systems described herein including a preloaded and automatically reloadable cartridge to repair tissue.
Figure 8B:
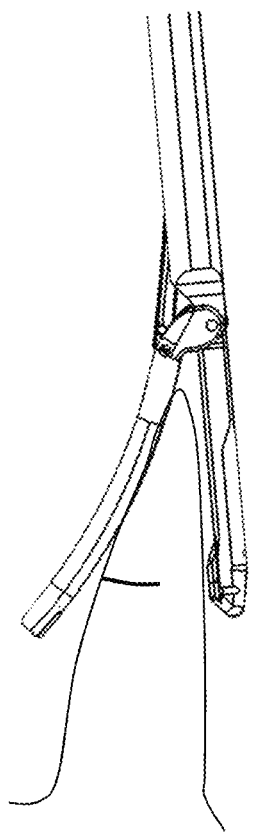
Figure 8C:
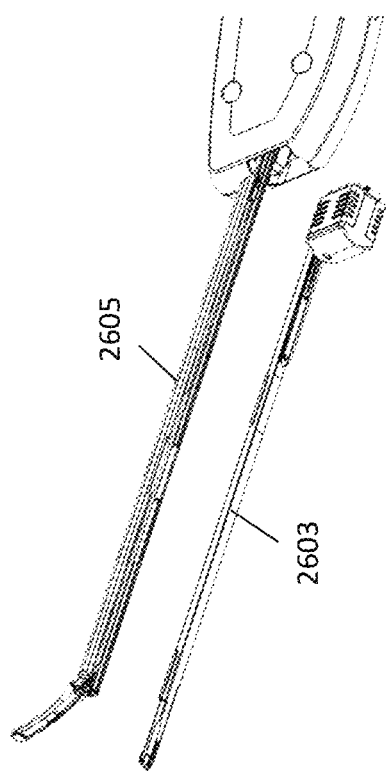
Figure 8D:
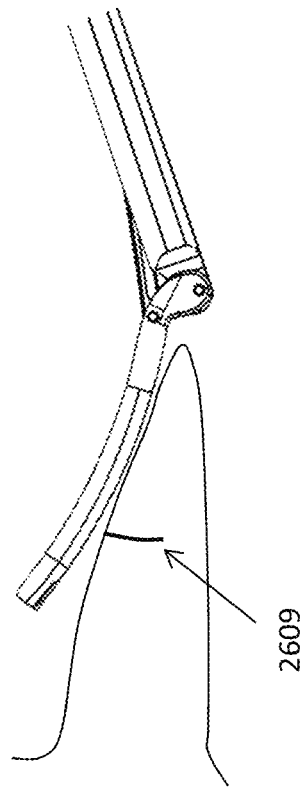
Figure 8E:
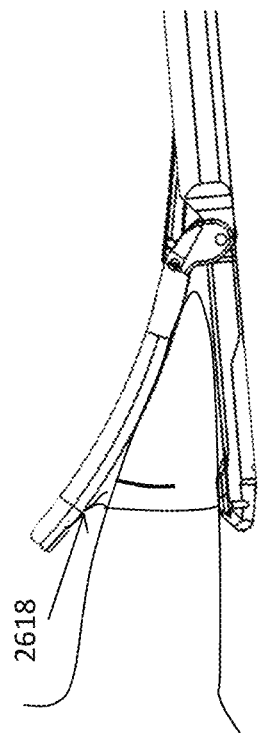
Figure 8F:
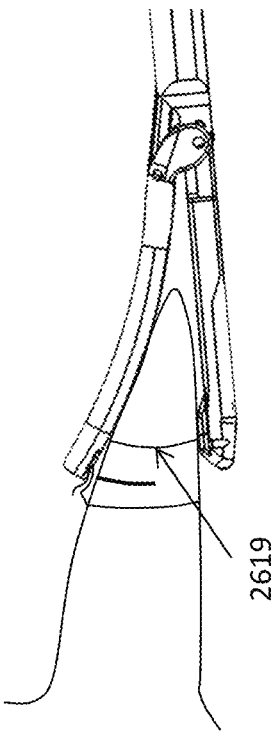

In FIGS. 8A and 8B, the suture passer is first assembled by coupling a preloaded cartridge 2603 with a durable assembly 2605 to form a suture passer 2601. In FIG. 8C, the suture passer is positioned adjacent to the target (torn meniscus) tissue; in this example, the upper jaw of the suture passer is pivotable/bendable relative to the elongate axis of the device, and the lower jaw is axially retracted (proximally) so that the tip of the suture passer has a very narrow profile and can fit into the narrow confines of the anatomy. In FIG. 8D, the lower jaw is extended distally to surround the torn meniscus. In FIG. 8E the tissue penetrator 2611 is extended from the lower jaw (from the cartridge) to the upper jaw while pushing a first bight region of suture. The tissue penetrator is then retracted, leaving the first bight region of suture at a first end of the suture held in the suture retainer region 2618 of the upper jaw, as shown in FIG. 8F. The suture 1615 then extends from the upper (superior) side of the meniscus and the upper jaw to the lower (inferior) side of the meniscus and the lower jaw. Withdrawing the tissue penetrator into the lower jaw housing (shown in FIG. 8E) may automatically re-load the tissue penetrator with the second bight of suture near the distal end of the suture, as discussed above. For example, when the second bight of suture is held in a fixed position and the distal end region of the suture next to the second bight is held in a releasable hold on the tissue penetrator, the tension pulling the second bight proximally may pull the second bight into the suture engagement region (now empty) on the tissue penetrator. This automatically re-loads the tissue penetrator with a second bight of tissue.

Figure 8G:
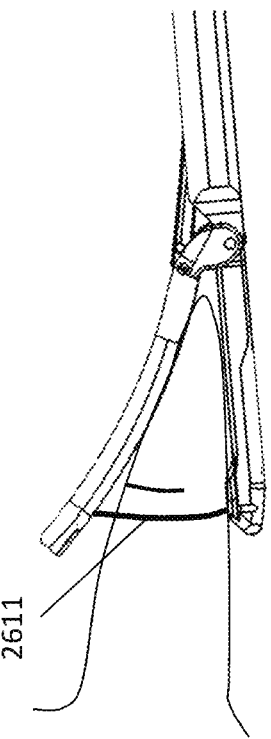
Figure 8H:
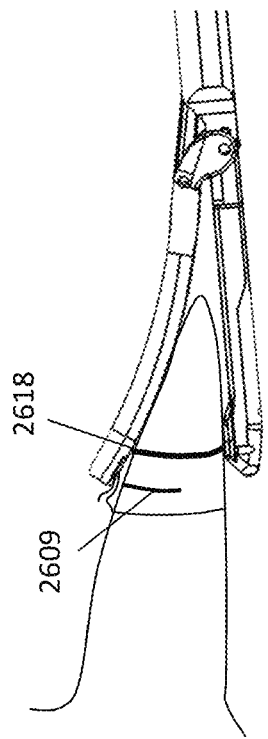
Figure 8J:
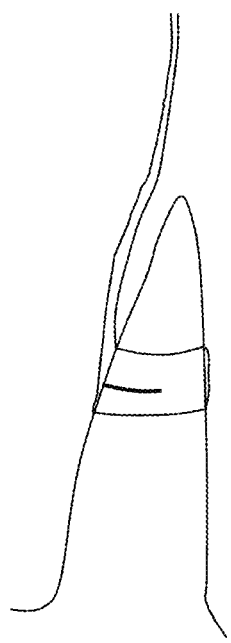
Figure 8L:
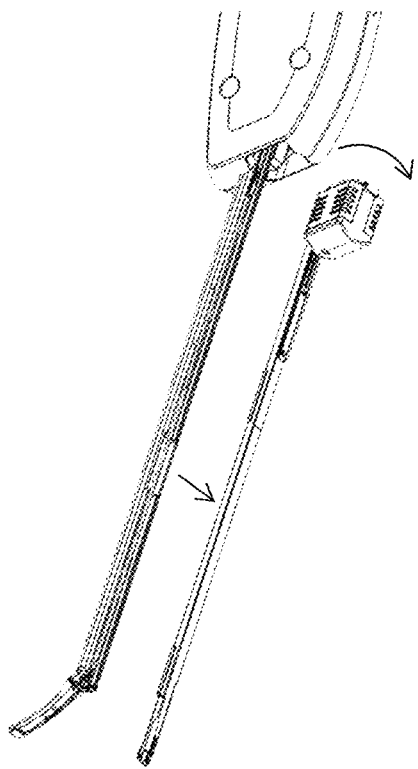
Figure 8I:
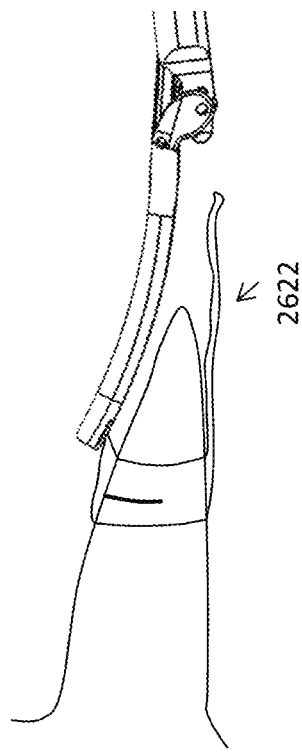
Figure 8K:
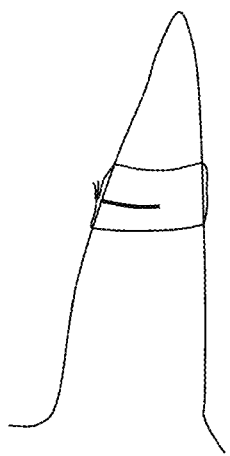

In FIG. 8G the suture passer is repositioned on the meniscus so that it can suture on the more apical side of the tear 2609. Once positioned, the suture passer is again activated (e.g., by actuating the lower jaw/needle extension control on the handle) to drive the tissue penetrator from the lower jaw through the tissue to the upper jaw, where the second bight region also engages with a suture retainer 2618 in the upper jaw. The same or a different suture retainer may be used. Withdrawing the tissue penetrator again leaves the second length 2619 of suture behind in the meniscus, as shown in FIG. 8H. Thereafter, the lower jaw can be retracted, leaving the suture "slack" 2622 (the suture body) on the inferior side of the meniscus, and allowing the loop to be closed by withdrawing the suture passer (including the upper jaw) from the knee, as shown in FIG. 8J. A knot pusher (not shown) can then be used to tighten and tie a knot in the loop of suture, repairing the tear, as shown in FIG. 8K. The cartridge may then be removed from the durable assembly, as shown in FIG. 8L, and another (new) cartridge may be applied.

Asymmetric Needles

The needles shown in FIGS. 4A-7C above are typically symmetric at their distal tip. For example, compare needle of FIG. 13B (symmetric) with the needle of FIG. 13A (not symmetric). Making the needle tip asymmetric such that the tip resides in the lower jaw channel may also help solve the problem described above with recapture of the suture length by the tissue penetrator.

The tissue penetrators (needles) described herein typically have a sharp distal tip that is adapted to penetrate tissue. The sharp distal tip may be located anywhere along the width of the tissue penetrator. For example, the sharp distal tip may be centered relative to the width, as shown in FIG. 7A, or it may be laterally offset from the midline of the tissue penetrator (where the midline extends in a proximal to distal direction).

Figure 14A:
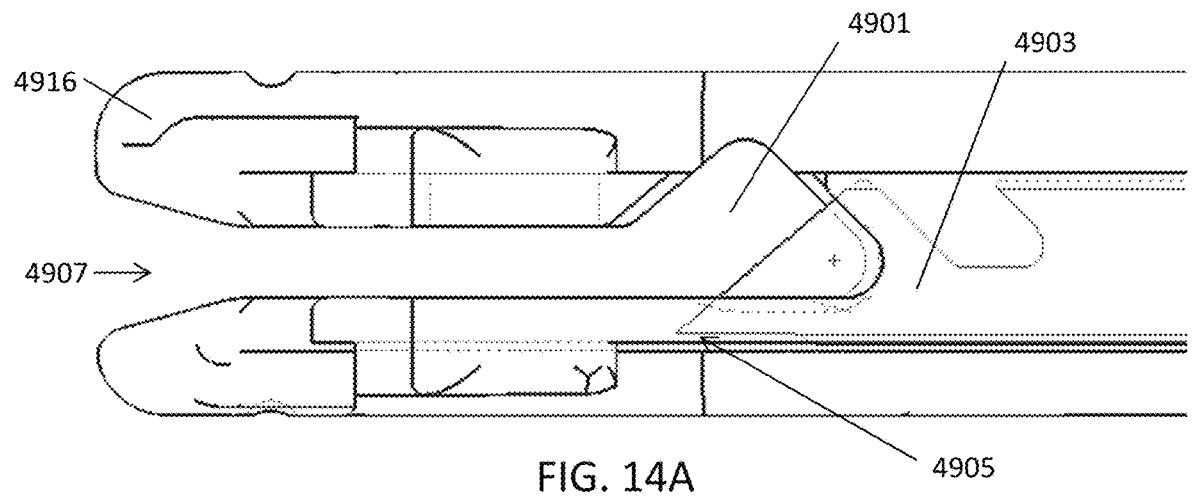
FIG. 14A shows a top view of a lower jaw member having a tissue penetrator such as the one shown in FIG. 13B, with a laterally positioned sharp tip (relative to the width of the tissue penetrator).

In some variations, it may be desirable to have the sharp distal tip region laterally offset from the midline of the width, as illustrated in FIG. 14A. In particular, in variations in which the jaw member in which the tissue penetrator is housed include a longitudinal suture loading channel. However, a needle having a centered sharp distal tip may snag or catch on the suture when loading the suture into the central channel. For this reason, a laterally offset sharp distal tip. An asymmetric needle tip offers advantages for loading suture when there is a central suture loading channel in the lower jaw, because having the needle tip off to one side of the loading groove may ensure that the sharp tip of the needle is not exposed to the suture, mitigating the chances that the suture will snag on the needle tip, as shown in FIG. 14A. The central suture-loading channel 4907 in the jaw 4916 is continuous with a suture holding region 4901 and the entire channel (and thus any suture held within the channel) is protected from the sharp distal tip 4905, as the sharp distal tip 4905 of the tissue penetrator 4903 is laterally displaced and is held within the jaw 4916.

Figure 14B:
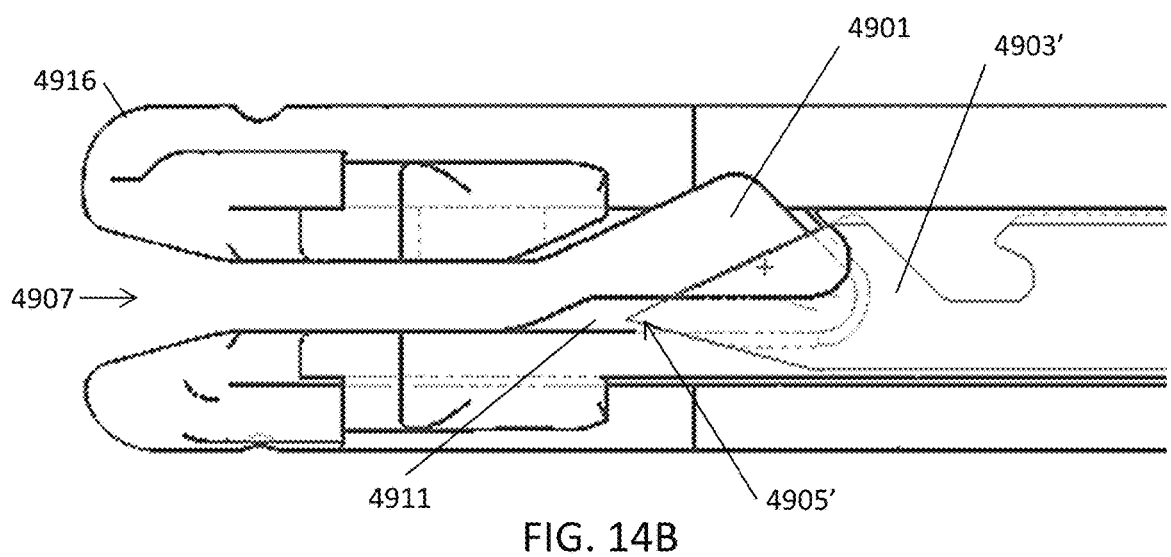
FIG. 14B shows an example of a lower jaw including a tissue penetrator such as the one shown in FIG. 14A, in which the distal tip region is less than 40% off-center. The lower jaw member includes a tip shield region in the central suture loading channel to prevent a suture from snagging on the sharp distal tip when loading/unloading into the tissue penetrator. This may also prevent entanglement/entrapment of a region of suture as described herein.
Figure 16:
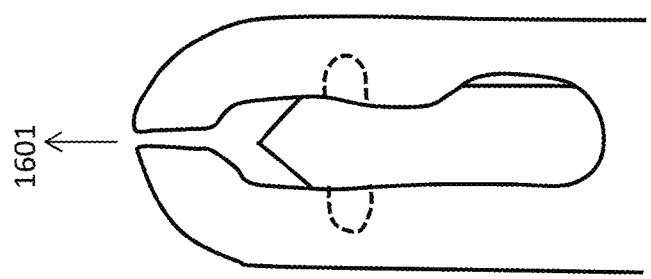
FIG. 16 is another example of a variation of a lower jaw member of a preloaded suture passer configured to prevent entanglement and/or entrapment of a region of suture when passing a second (or a second region of a) suture. In this example, the opening at the distal end is narrow, and shaped with the outer-facing (distal-facing) surface rounded, to prevent or reduce the likelihood that a region of suture from entering into the opening before or during passing of a second length of suture.

In general, tissue penetrators having less asymmetrically located sharp distal tips (e.g., less laterally offset from the midline) may have less of a tendency to deviate laterally when extending through the tissue, and may therefore have a higher reliability when contacting the suture retention feature in the opposite jaw. However, to ensure that suture can enter the loading area of the suture passer without snagging on the needle tip, the shape of loading channel may be modified to cover the needle tip. For example, FIG. 14B illustrates one variation of a jaw having a central suture loading channel 4907 to load a suture into a tissue penetrator. The jaw includes a ramped cover 4911 housing the centrally (or slightly offset from the midline, e.g., less than 30% offset, less than 25% offset, less than 20% offset, less than 15% offset, etc. from the midline) located sharp distal tip 4905' of the tissue penetrator 4903'. Thus, a suture may be protected from snagging on the tissue penetrator tip when being loaded in the central channel 4907.

Any of the tissue penetrators described herein may also be adapted to prevent snagging of tissue (e.g., capsule or meniscal tissue) when extending through the tissue. Any of the suture passers described herein could be used for repair of soft tissue in joints, to sew in allografts or artificial soft tissue constructs such as an artificial meniscal scaffold or graft, and/or for meniscus repair.

Figure 15:
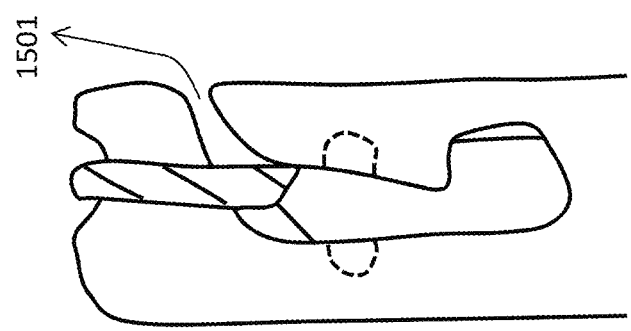
FIG. 15 illustrates another variation of a lower jaw member of a preloaded suture passer configured to prevent entanglement and/or entrapment of a region of suture when passing a second (or a second region of a) suture. In this example, the lower jaw member has an opening only at the lateral side, not the distal end, out of which the suture loop may pass.

In some variations the jaw member housing the tissue penetrator may also or alternatively be reconfigured to prevent or reduce the likelihood of entrapment/recapture of the suture in the jaw (e.g., by the tissue penetrator). For example, in some variations, the lower jaw may be reconfigured to have a closed distal end that the suture wraps around, similar to the pin, but without having to open. Instead, the distal end region of the jaw may include a laterally-offset opening into the distal channel. As shown in FIG. 15, this may allow the suture to escape the lower jaw through a side channel 1501, while preventing a suture from easily entering the distal end of the jaw member.

Alternatively, in some variations, the opening at the distal end (distally—facing opening) into the channel within the jaw member housing the tissue penetrator is still present, but is adapted to reduce the likelihood of a suture re-entering the channel. This may be achieved by having a very narrow channel (e.g., having a diameter approximately the same as or just slightly larger than the diameter of the suture); the outer edge of the channel may transition abruptly from a smooth or rounded distal-facing surface, which does not guide a suture into the channel. This very narrow channel at the tip of the lower jaw may therefore allow the suture to escape when the suture is in tension 1601, but would be narrow enough to make it difficult for the suture to enter the lower jaw channel when the lower jaw is pushed against the suture.

Although many of the variations of suture passer devices described herein are configured so that the tissue penetrator extends distally from an opening in a jaw, any of the suture passers described herein may be configured so that the tissue penetrator extends proximally after extending between the upper and lower jaws. Thus, the deflection features on the upper jaw could be set to facilitate the needle heading in the proximal direction. For example, in some variations the tissue penetrator extends proximally within (or out of) the upper jaw member after extending across the opening between the jaws.

Centering Second Suture Bight

Any of the apparatuses described herein may include one or more features such as a centering channel that pulls a second bight of suture into the needle's hook as the needle is retracted (e.g., when reloading the suture into the needle), which may help in positioning the second bight of suture within the hook, to ensure that the suture is loaded and passed successfully.

Figure 13A:
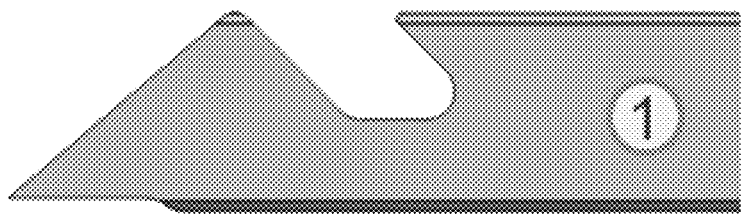
FIG. 13A illustrates a symmetric tissue penetrator (needle).
Figure 13B:
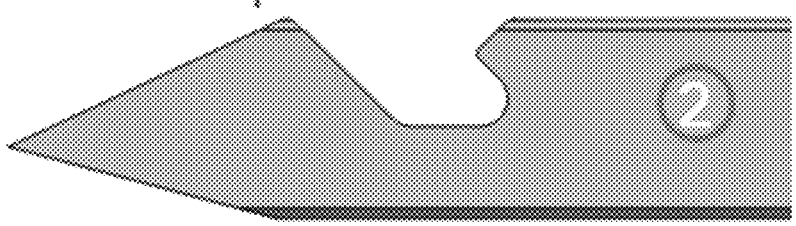
FIGS. 13B and 13C illustrate examples of asymmetric tissue penetrators (needles).
Figure 13C:
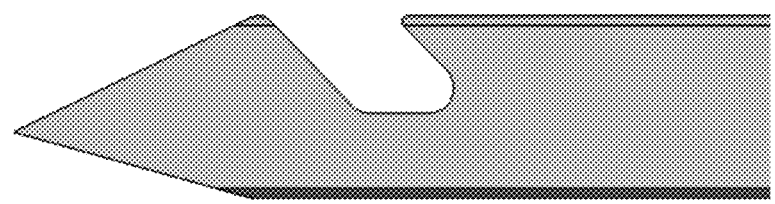

For example, FIGS. 13A-13C illustrate examples of needles having hooks that may be preloaded with a first length of suture and then reloaded with another length of suture into a hook of the needle.

In some variations, the needle is coupled to a sled or or sleeve. The sled may be attached to the needle, and may travel with the needle. As described in U.S. application Ser. No. 14/572,485, filed Dec. 16, 2014 (US-2015-0196294), now U.S. Pat. No. 9,494,162, herein incorporated by reference in its entirety, a needle sled may be used to releasably hold and apply tension to a second suture end so that it may be pulled into the hook region of the needle when the needle is withdrawn back into the suture passer after passing the first length (end) of suture. For example, once the needle has been extended, and as it is retracted, the needle sled may apply tension to the second suture end held by the sled or a releasable attachment on the sled. In some variations, as described herein, the lower jaw in which the needle is slide and retained, may include a suture guiding feature ("suture guide") through which the second suture end may be threaded. The suture guide feature may be shaped and positioned relative to the needle hook such that when the suture is tensioned, the suture is pulled centrally and loaded into the hook of the needle. The needle can then be re-advanced to pass the second suture end.

In another embodiment, the second suture end is tensioned by the needle rather than by the needle sled.

Figures 17A, 17B:
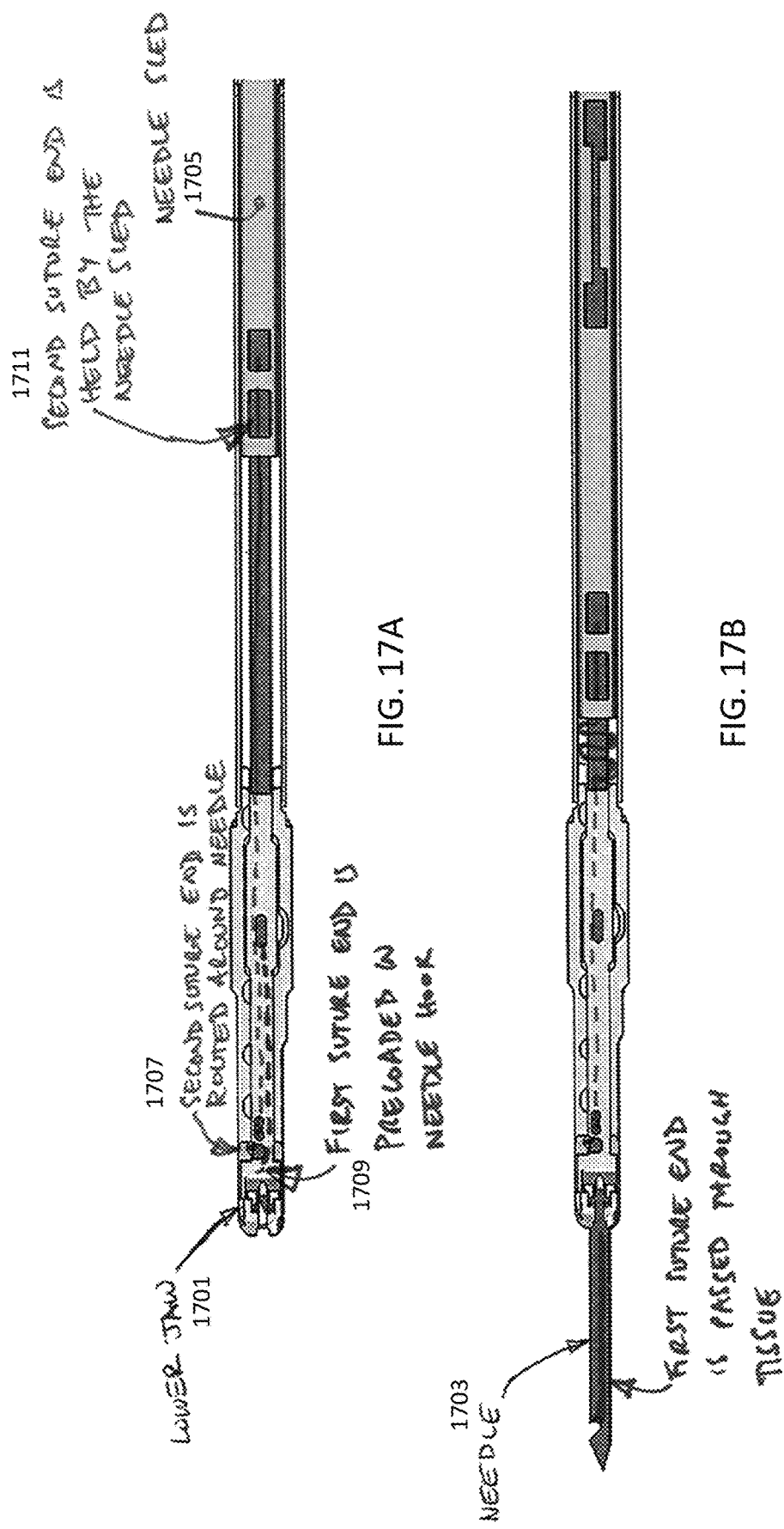

FIGS. 17A-17E illustrate passing both ends of a suture. For example, in FIG. 17A, a first/lower jaw 1701 includes a needle 1703 that is coupled to a sled 1705, and a first suture end 1709 is preloaded into the needle hook, while the second bight (a loop at the second end of the suture) is held within the first jaw 1707, e.g., in a suture holding region within the first/lower jaw, and the second end region 1711 is held on the sled 1705. The first end of the suture is passed through the tissue by extending the needle 1705 (and sled coupled thereto) distally, as shown in FIG. 17B. When the needle and sled are retracted proximally, as shown in FIGS. 17C and 17D, the second end of the suture is tensioned as the sled moves proximally, so that the bight of suture near the second end that is held in the suture holding region within the first/lower jaw can then be pulled into the hook region of the needle, as shown in FIG. 17D. Thereafter, the needle with the loaded second bight region can then be passed through the tissue to pass the second end, as shown in FIG. 17E.

Figure 18A:
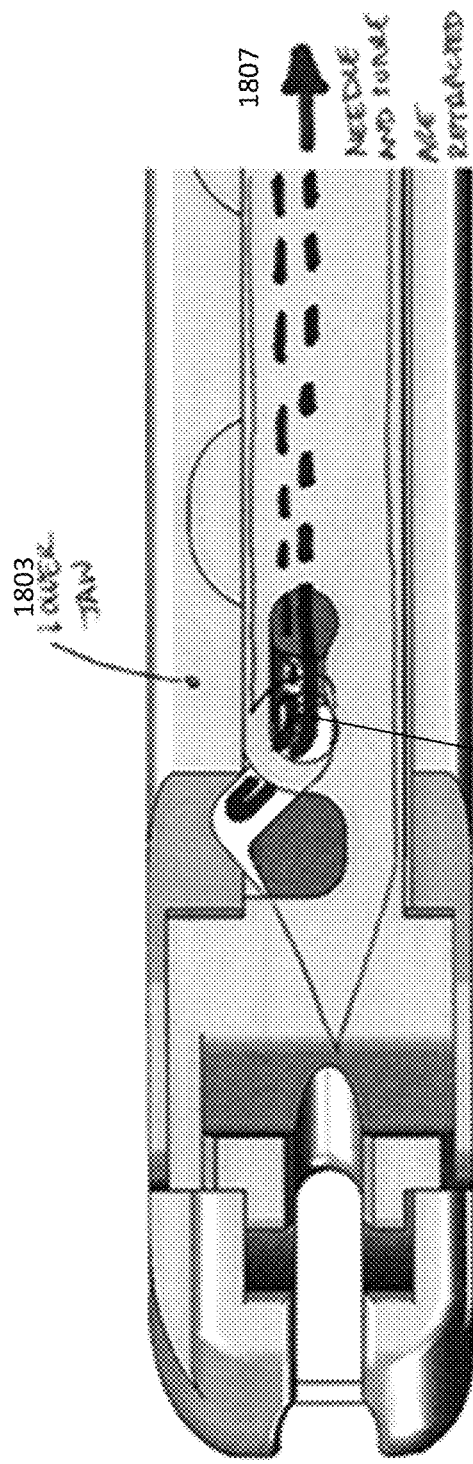
FIGS. 18A and 18B illustrate a first example of a suture passer lower jaw portion including a centering channel (e.g., a suture guide) that may be help direct the second bight of suture into the needle (tissue penetrator) hook region.
Figure 18B:
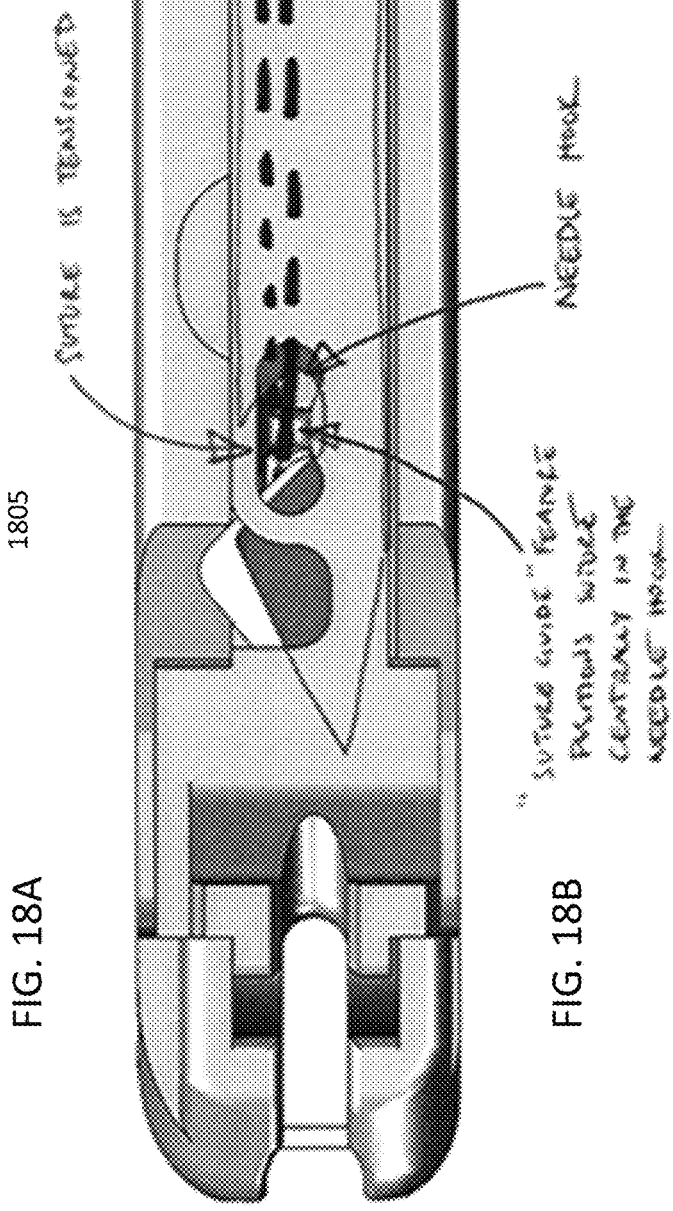

As just discussed above, the step of moving the second bight region into the hook of the needle is important, because if it is not properly performed, the suture (second bight) may not be loaded properly and may fall out of the needle, or may only be partially loaded. Described herein are devices and methods of using them for directly the tension in the second bight/second end of the suture so that it may more accurately be loaded into the hook of the needle. For example, in some variations, a suture guide (e.g., centering channel) may be included to assist in loading the second suture (second bight) into the needle hook. FIGS. 18A and 18B illustrate one example of a suture apparatus as described herein in which a suture guide is included to guide the tensioned second bight region of the suture that is preloaded within the first/lower jaw so that the second bight is pulled reliably and completely into the hook of the needle. The suture guide may be part of the suture holding region within the jaw housing, or it may be separately attached to the first/lower jaw.

For example, FIGS. 18A and 18B, a suture guide feature 1805 is included as part of the first/lower jaw 1803, and the needle slides relative to the suture guide feature. In this example, the suture guide feature loads the second suture bight region into the needle hook after the first bight has been passed, and the needle retracted 1807 proximally. The suture guide feature (or guide feature) 1805 include an eyelet forming a channel that provides a centrally directed force vector to move the suture centrally (toward the midline of the first/lower jaw) and therefore into the hook region of the needle, as shown in FIG. 18B. FIGS. 19A-19D illustrate other variations of suture guide features as described herein. In FIGS. 19A-19D the guide feature includes a channel or opening near the longitudinal midline of the first/lower jaw over which the suture may wrap. When the needle and sled are moved proximally after passing the first suture bight preloaded into the device, the second bight is held within the suture holding region within of the jaw housing laterally offset from the longitudinal midline of the first/lower jaw; the guide feature is positioned opposite and slightly proximally to the suture holding region within the jaw housing, and includes a channel for the second bight region of the suture that directs the second bight region centrally (toward the midline of the first/lower jaw 1901) when a cut-out portion of the needle (such as the hook region) exposes the channel of the guide feature 1905 allowing the second bight to transition from the suture holding region (e.g., a suture holding region within the jaw housing) into the midline region of the jaw along the channel of the guide feature.

As mentioned above, if a suture guide feature is not used, the needle sled may apply tension to the suture without a midline-directed vector (e.g., a vector having a centrally directed component). Without some centrally directed component of tension, it is possible for the needle hook to miss the second leg of the suture, leaving the second leg of the suture to get pulled into the gap between the needle and the lower jaw, as illustrated in FIG. 20A, showing a suture 2001 falling into the gap between the needle 2005 and the suture holding region within the jaw housing. Another possible consequence of pulling on the second suture without a vector that has some centrally directed component is that the tip of the needle hook may grab a partial set of suture strands, but not the entire diameter of the suture, as illustrated in FIG. 20B, showing a needle 2001 hook, in which the needle has been advanced past the point where it is supposed to pick up the second bight, separating the suture 2005, as shown.

The suture guide features described herein may also be referred as centering features or as centering channels, and may be coupled or integral to the jaw (e.g., the first/lower jaw member). In particular, these centering features/centering channels may be formed through the jaw housing within which the tissue penetrator slides. A centering channel may include a channel is that is oriented centrally and configured to provide a force vector on the second bight of suture that is preloaded into a second bight region of the jaw to move the second bight towards the midline of the lower jaw when the needle is retracted. In general, the centering channel may be opposite from, radially inward to (e.g., towards the midline of the long axis), and slightly proximal to, the suture holding region within the jaw housing and located more closely toward the midline.

Figure 19D:
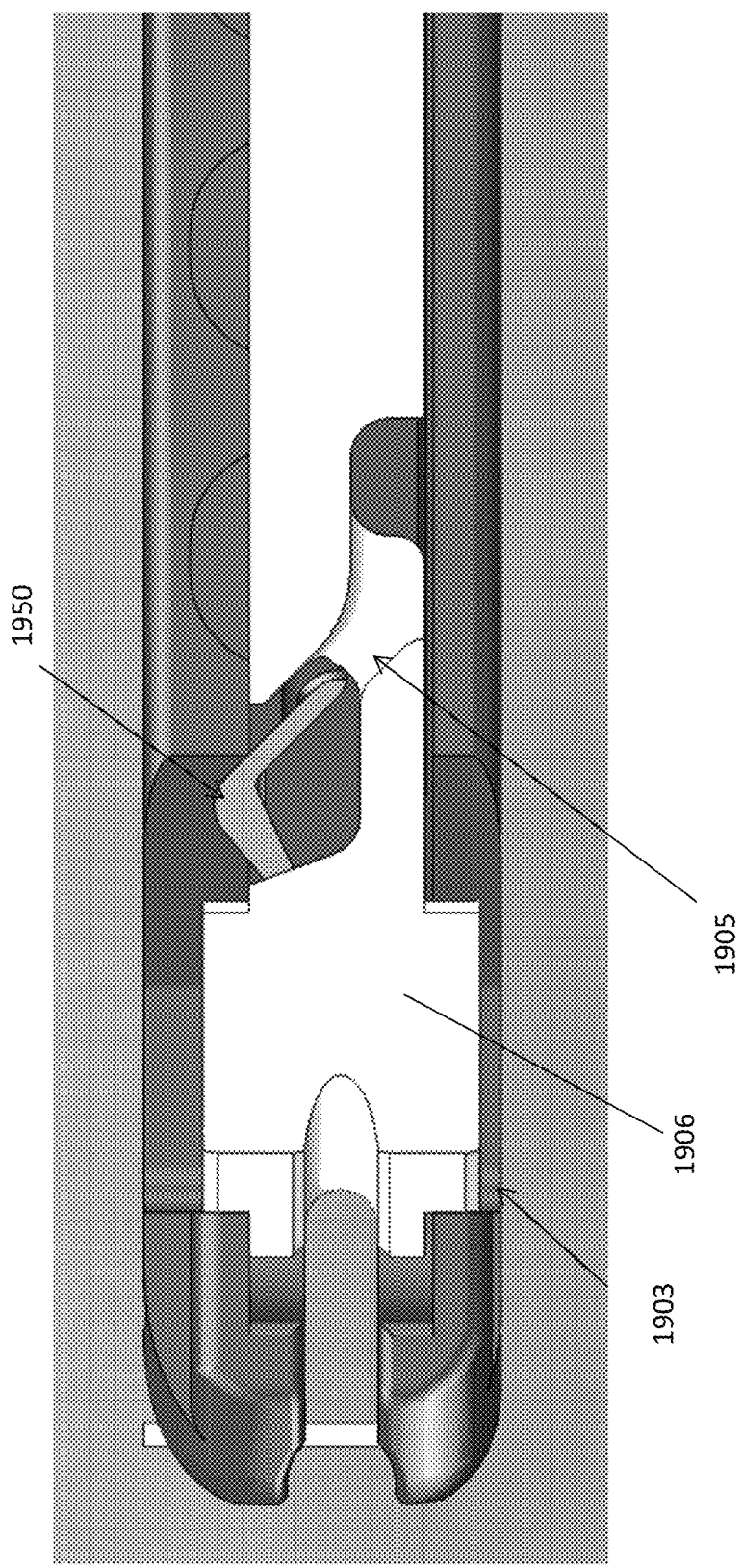

In general, the centering channel may include at least one loop through which a leg of the second bight is threaded. In FIGS. 18A-19D, the centering channel includes a pair of openings through an "upper" surface (or outer surface, such as the surface facing the opposite jaw) of the jaw housing that are connected by a recessed region (recessed channel), recessed relative to the surface of the jaw housing, within which the suture leg passes. The centering channel may be positioned slightly proximally and away from the suture holding region in the jaw housing. For example, in FIG. 19D, the suture holding region of the jaw housing 1950 is shown on the top of the figure in the jaw housing, while the centering channel is formed of a pair of openings through the upper surface of the jaw housing 1960 that are connected by a recessed channel 1905 between the two. The recessed channel is recessed down into the upper surface of the jaw housing 1960, and reduced the contact and friction between the suture and any tissue held in the jaws. In general this upper surface of the jaw housing is attached or integrally formed with the rest of the jaw housing forming the jaw (in this example, a lower jaw) and the tissue penetrator is slideably held within the jaw housing. FIGS. 19B and 19D show examples where the centering channel 1905 is positioned on an opposite side of the upper jaw housing away from the suture holding region of the jaw housing. Having a pair of openings through the upper surface of the jaw housing allows the suture to thread out and then back in while providing a centering force vector, so that the majority of the suture is held within the jaw housing, rather than running on top of the jaw housing, although a single hole or more than two openings (holes) may be used.

Although the description above is broken into parts and includes specific examples of variations of suture passers, any of the features or elements described in any particular example or section may be incorporated into any of the other embodiments. Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A suture passer apparatus with a preloaded suture, the apparatus comprising: an elongate body extending distally and proximally; a first jaw coupled to a distal end of the elongate body; a second jaw having a channel extending proximally from a distal end region of the second jaw; a tissue penetrator configured to slide distally and proximally within the second jaw; a suture within the second jaw, the suture comprising a first bight region loaded in a suture engagement region at a distal end region of the tissue penetrator, and a second bight region loaded in a suture holding region within the second jaw; and a gate comprising a deflectable pin at a distal end region of a jaw housing, wherein the gate is configured to open distally to allow the release of the suture from the channel, and to close to prevent a portion of the suture from re-entering the channel.

2. The apparatus of claim 1, wherein the gate comprises a turnstile mechanism.

3. The apparatus of claim 1, wherein the second jaw is configured to enclose the tissue penetrator until the tissue penetrator is extended from the jaw housing.

4. The apparatus of claim 1, wherein the first jaw is configured to pivot relative to the elongate body and wherein the second jaw is configured to slide axially relative to the elongate body.

5. The apparatus of claim 1, wherein the second jaw is removable.

6. A suture passer apparatus with a preloaded suture, the apparatus comprising: an elongate body extending distally and proximally; a first jaw coupled to a distal end of the elongate body; a removable second jaw having a channel extending proximally from a distal end region of the second jaw; a tissue penetrator configured to slide distally and proximally within the second jaw; a first length of suture within the second jaw, the first length of suture comprising a first bight region loaded in a suture engagement region at a distal end region of the tissue penetrator; a second length of suture within the second jaw, the second length of suture comprising a second bight region loaded in a suture holding region within the second jaw; and a gate comprising a deflectable pin at a distal end region of a jar housing, wherein the gate is configured to open distally to allow release of the first or second length of suture from the channel, and to close to prevent a portion of the first or second length of suture from re-entering the channel.

7. The apparatus of claim 6, wherein the gate comprises a turnstile mechanism.

8. The apparatus of claim 6, wherein the second jaw is configured to enclose the tissue penetrator until the tissue penetrator is extended from the jaw housing.

9. The apparatus of claim 6, wherein the first jaw is configured to pivot relative to the elongate body and wherein the second jaw is configured to slide axially relative to the elongate body.

10. A replaceable jaw cartridge that is preloaded with suture, the jaw cartridge comprising: a jaw housing configured to releasably engage a suture passer device, the jaw housing enclosing a channel extending proximally from a distal end of the jaw housing; a tissue penetrator configured to slide distally and proximally within the jaw housing; a first length of suture within the jaw housing, the first length of suture comprising a first bight region loaded in a suture engagement region al: a distal end region of the tissue penetrator; a second length of suture within the jaw housing, the second length of suture comprising a second bight region loaded in a suture holding region within the jaw housing; and a gate comprising a deflectable pin at a distal end region of the jaw housing, wherein the gate is configured to open distally to allow release of the first or second length of suture from the channel, and to close to prevent a portion of the first or second length of suture from re-entering the channel.

11. The jaw cartridge of claim 10, wherein the gate comprises a turnstile mechanism.

12. The jaw cartridge of claim 10, wherein the jaw housing is configured to completely enclose the first length of suture, the second length of suture and tissue penetrator until the tissue penetrator is extended from the jaw housing.

13. The jaw cartridge of claim 10, wherein the jaw housing comprises a keyed connector configured for coupling with an elongate member of the suture passer device.

14. The jaw cartridge of claim 10, wherein a distal tip of the tissue penetrator is laterally offset with respect to a centerline along a length of the channel.

15. The jaw cartridge of claim 10, wherein the channel comprises a ramp adapted to guide the tissue penetrator away laterally out of the jaw housing at the distal end region.

16. The jaw cartridge of claim 10, wherein the suture holding region is positioned opposite from the suture engagement region of the tissue penetrator when the tissue penetrator is withdrawn proximally within the jaw housing.

* * * * *